United States Patent [19]

Ohnishi et al.

[11] Patent Number: 4,888,332

[45] Date of Patent: * Dec. 19, 1989

[54] CEPHALOSPORIN DERIVATIVES

[75] Inventors: Haruo Ohnishi, Funabashi; Hiroshi Kosuzume, Mishima; Masahiro Mizota, Gotenba; Yasuo Suzuki, Kawaguchi; Ei Mochida, Tokyo, all of Japan

[73] Assignee: Mochida Pharmaceutical Co., Ltd., Tokyo, Japan

[*] Notice: The portion of the term of this patent subsequent to Jun. 20, 2006 has been disclaimed.

[21] Appl. No.: 687,455

[22] Filed: Dec. 28, 1984

[30] Foreign Application Priority Data

Dec. 29, 1983 [JP] Japan .................................. 58-247251

[51] Int. Cl.$^4$ .................. C07D 501/36; A61K 31/545
[52] U.S. Cl. .................................... 514/206; 540/227; 540/222; 540/226
[58] Field of Search .................... 544/27, 90; 540/227; 514/205, 206

[56] References Cited

U.S. PATENT DOCUMENTS

| | | | |
|---|---|---|---|
| 4,103,085 | 7/1978 | Naito et al. | 544/27 |
| 4,104,469 | 8/1978 | Naito et al. | 544/27 |
| 4,151,352 | 4/1979 | Naito et al. | 544/27 |
| 4,278,793 | 7/1981 | Durckheimer et al. | 544/27 |
| 4,316,024 | 2/1982 | Iimura et al. | 548/27 |
| 4,331,666 | 5/1982 | Nannini et al. | 424/246 |
| 4,436,912 | 3/1984 | Wheeler | 548/233 |
| 4,500,526 | 2/1985 | Imae et al. | 514/226 |
| 4,526,977 | 7/1985 | Commons et al. | 548/246 |
| 4,547,494 | 10/1985 | Oine et al. | 514/204 |
| 4,576,956 | 3/1986 | Makisumi | 514/380 |
| 4,587,333 | 5/1986 | Ono et al. | 544/521 |
| 4,594,417 | 6/1986 | Yang | 544/28 |
| 4,600,773 | 7/1986 | Engle | 544/30 |
| 4,604,457 | 8/1986 | Torii et al. | 540/223 |
| 4,609,654 | 9/1986 | Labeeuw et al. | 514/206 |
| 4,621,081 | 4/1986 | O'Callaghan et al. | 514/206 |

FOREIGN PATENT DOCUMENTS

| | | |
|---|---|---|
| 75805 | 4/1983 | European Pat. Off. . |
| 0082501 | 6/1983 | European Pat. Off. . |
| 2128498 | 12/1971 | Fed. Rep. of Germany . |
| 2456109 | 12/1980 | France . |
| 1892245 | 1/1977 | New Zealand . |
| 203436 | 6/1980 | New Zealand . |
| 186968 | 4/1981 | New Zealand . |
| 188163 | 10/1981 | New Zealand . |
| 196642 | 7/1984 | New Zealand . |
| 202332 | 10/1985 | New Zealand . |
| 206704 | 4/1986 | New Zealand . |
| 1399086 | 6/1975 | United Kingdom . |
| 2017702A | 10/1979 | United Kingdom . |
| 1576625 | 10/1980 | United Kingdom . |
| 1604971 | 12/1981 | United Kingdom . |
| 893428 | 4/1982 | United Kingdom . |
| 2104888A | 3/1983 | United Kingdom . |

OTHER PUBLICATIONS

Dunn, J. Antimicrob. Chemotherapy (1982) 10, Suppl. C, pp. 1–10.
Natio, et al., Chem. Abstracts vol. 88 (1978), entry 22797.
Chemical Abstracts 102:113169e (1989).
Chemical Abstracts vol. 102, 1985 Abstract No. 24539Z.
Chemical Abstracts vol. 100, 1984 Abstract No. 22505d.
Chemical Abstracts vol. 102, 1985 Abstract No. 6056u.
Chemical abstracts vol. 103, 1985 Abstract No. 37281p.
Alpegiani et al., "Cephalosporins VI", *The Journal of Antibiotics*, vol. XXXVI, No. 8, Aug. 1983, pp. 1013–1019.

*Primary Examiner*—Nicholas S. Rizzo
*Attorney, Agent, or Firm*—Oliff & Berridge

[57] ABSTRACT

The present invention relates to novel cephalosporin derivatives, processes for preparing thereof, compositions for preventing and/or treating infectious diseases which comprise the novel cephalosporin derivatives as active components, and the intermediate compounds in the synthesis of cephalosporin derivatives and processes for producing thereof.

The novel cephalosporin derivatives according to the present invention contain condensed heterocyclic groups, particularly a triazolopyrimidine ring or a thiadiazolopyrimidine ring as substituents at the 3-position of the cephem skeleton, and a hydroxyimino, an alkyloxyimino or an acyloxyimino moiety as substituents at the 7-position of the cephem skeleton.

The compounds of the present invention containing the aforementioned substituents have a strong antibacterial activity against gram-negative bacteria and also against gram-positive bacteria including methicillin-resistant Staphylococcus aureus. These compounds are extremely useful for the treatment of infectious diseases.

94 Claims, No Drawings

CEPHALOSPORIN DERIVATIVES

BACKGROUND OF THE INVENTION

The present invention relates to novel cephalosporin derivatives, processes for producing the same and compositions containing cephalosporin derivatives for treating and/or preventing infectious diseases.

Developments of cephalosporin derivatives have been remarkable. Some cephalosporin derivatives have been developed which have excellent antibacterial activity against gram-negative bacteria. However, the antibacterial activity of these cephalosporin derivatives against gram-positive bacteria is rather poor. Several cephalosporin antibiotics have been used for the treatment of gram-positive bacteria infections and the increase of gram-positive bacteria resistant to cephalosporin antibiotics, for example, methicillin-resistant *Staphylococcus aureus* (MRSA), has become widely known year by year.

From the foregoing background, it has been desired to develop cephalosporin derivatives having a strong antibacterial activity against gram-positive bacteria while retaining a sufficient antibacterial activity against gram-negative bacteria.

SUMMARY OF THE INVENTION

An object of the present invention is to provide novel cephalosporin derivatives.

Another object of the present invention is to provide processes for producing novel cephalosporin derivatives.

A further object of the present invention is to provide compositions for preventing and/or treating infectious diseases which comprise novel cephalosporin derivatives as active components. A further object of the present invention is to provide intermediate compounds in the synthesis of cephalosporin derivatives and processes for producing such intermediate compounds.

The present invention is based on the selections of groups containing condensed heterocyclic groups, particularly a triazolopyrimidine ring or a thiadiazolopyrimidine ring, and groups containing an acyloxyimino moiety as substituents at the 3-position and 7-position of the cephem skeleton, respectively.

The compounds of the present invention containing these substituents have a wide antibacterial spectrum against gram-negative bacteria and gram-positive bacteria including methicillin-resistant *Staphylococcus aureus*. These compounds are extremely useful for the treatment of infectious diseases.

DETAILED DESCRIPTION OF THE INVENTION

As a result of extensive investigations concerning development of cephalosporin derivatives having satisfactory anti-bacterial activity against gram-negative bacteria and also having strong anti-bacterial activity against gram positive bacteria, the present inventors have found that cephalosporin derivatives represented by the general formula (I) satisfy these requirements and, have accomplished the present invention.

The present invention is directed to cephalosporin compounds represented by the general formula (I):

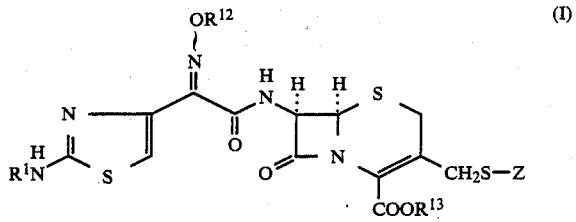

and salts, hydrates and hydrates of salt thereof; wherein $R^1$ represents a hydrogen atom or an amino-protecting group; Z represents a group represented by:

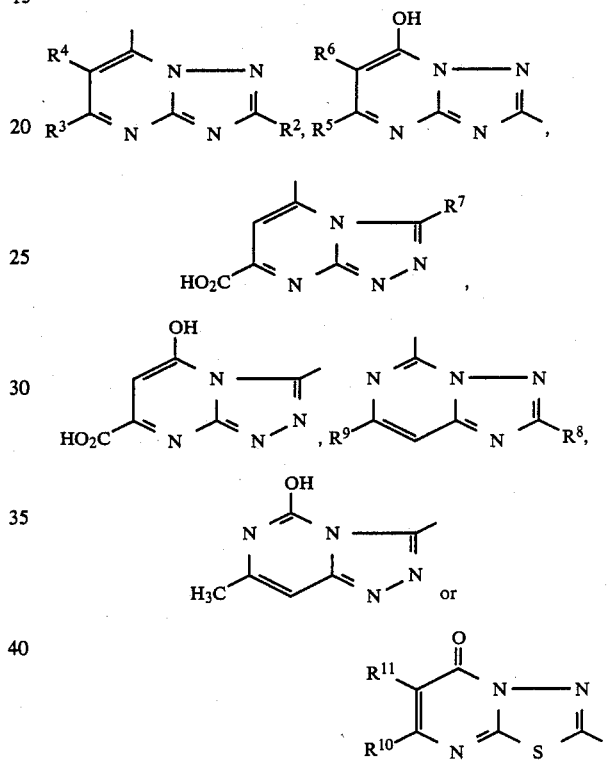

wherein $R_2$ represents a hydrogen atom, a methyl group, an amino group, a cyano group, a hydroxysulfonyl group, a carboxyl group, a carboxymethyl group, a protected carboxyl group, a methoxycarbonyl group or a hydrazinocarbonyl group, $R^3$ represents a hydrogen atom, a lower alkyl group having 1 to 3 carbon atoms, a hydroxy group, a methoxy group, a carboxyl group, a carboxymethyl group or a chlorine atom, $R^4$ represents a hydrogen atom, a methyl group or a carboxyl group, $R^5$ represents a hydrogen atom or a methyl group, $R^6$ represents a hydrogen atom, a carboxyl group, an ethoxycarbonyl group or a piperidinocarbonyl group, $R^7$ represents a hydrogen atom or a methyl group, $R^8$ represents a hydrogen atom or a carboxyl group, $R^9$ represents a methyl group, an amino group or a carboxyl group, $R^{10}$ represents a hydrogen atom or a methyl group and $R^{11}$ represents a hydrogen atom or a carboxyl group; $R^{12}$ represents a hydrogen atom, a methyl group, a hydroxyl-protecting group or an acyl group, $R^{13}$ represents a hydrogen atom or a carboxyl-protecting group and the bond represented by a wavy line represents a bond of anti-form or syn-form. The present invention is also directed to a process for preparing the above-described cephalosporin compounds. The present invention is further directed to pharmaceutical compositions for treating and/or preventing infectious diseases characterized by containing these cephalosporin derivatives as active components.

In the cephalosporin derivatives of the present invention represented by general formula (I), it is known that the aminothiazole moiety as the substituent at the 7-position thereof exhibits tautomerism as shown below:

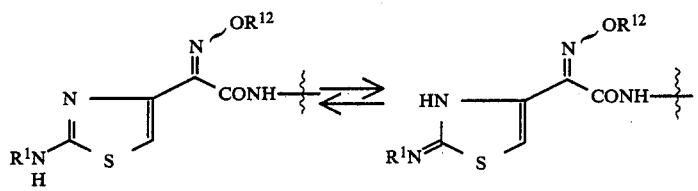

wherein $R^1$, $R^{12}$ and the wavy line have the same significance as defined above. In the present invention, the aminothiazole moiety is expressed as including both isomers since both are generally deemed to be the same substance. Accordingly, the compounds of the present invention represented by general formula (I) also include both of these tautomeric isomers.

Specific examples of salts of the compounds represented by general formula (I) include pharmacologically acceptable salts such as alkali metal salts such as a sodium salt, a potassium salt, etc.; alkaline earth metal salts such as a calcium salt, etc.; salts of organic bases such as an ammonium salt, a benzylamine salt, a diethylamine salt, etc.; salts of amino acids, such as an arginine salt, a lysine salt, etc. These salts of the compounds may be a mono-salt, a di-salt or a tri-salt. In the case of mono-salts or di-salts, the salts may be salts of the carboxyl group at the 2-position and/or salts of the carboxyl group contained in the substituents at the 3-position, of the cephem skeleton.

The compounds represented by general formula (I) may form acid addition salts with pharmacologically acceptable organic or inorganic acids. Typical examples of these salts include salts of inorganic acids such as hydrochlorides, hydrobromides, sulfates, phosphates, etc.; salts of organic acids such as acetates, citrates, maleates, tartarates, benzoates, ascorbates, ethanosulfonates, toluenesulfonates, etc. The compounds of the present invention represented by general formula (I) may be present as a syn-isomer shown below:

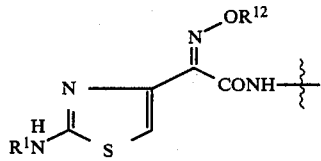

wherein $R^1$ and $R^{12}$ have the same significance as defined above; or as an anti-isomer shown below:

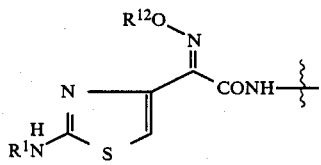

wherein $R^1$ and $R^{12}$ have the same significance as defined above; or as a mixture of these isomers. Among them, the syn-isomer is particularly preferred and, mixtures mainly composed of the syn-isomer are also preferred.

In the compounds of the present invention represented by general formula (I), the amino-protecting groups may be selected from acyl groups such as formyl, acetyl, chloroacetyl, t-butoxycarbonyl, benzyloxycarbonyl, etc.; or aralkyl groups such as benzyl, diphenylmethyl, triphenylmethyl, etc. The carboxyl-protecting groups, may be selected from alkyl esters such as methyl ester, ethyl ester, etc.; or aralkyl esters such as benzyl ester, diphenylmethyl ester, triphenylmethyl ester, etc. Specific examples of hydroxyl protecting groups include aralkyl groups such as benzyl, etc.; or alkoxyalkyl groups such as methoxymethyl, 1-methyl-1-methoxyethyl, etc. Taking into account various operations, synthesis of thus protected products, conditions for removing the protecting groups, etc. collectively, it is preferred to use a triphenylmethyl group as the amino-protecting group, diphenylmethyl ester as the carboxyl-protecting group and 1-methyl-1-methoxyethyl as the hydroxyl-protecting group, respectively.

The compounds of the present invention represented by general formula (I) can be prepared as follows. Namely;

Process A

The compounds of the present invention represented by general formula (I) may be produced by reacting compounds represented by general formula (II):

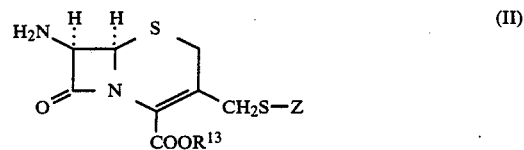

wherein $R^{13}$ and Z have the same significance as defined above, with compounds represented by general formula (III):

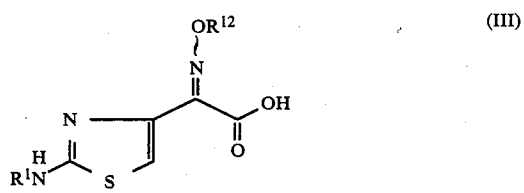

wherein $R^1$, $R^{12}$ and the wavy line have the same significance as defined above.

In this process, the compounds represented by general formula (II) may be protected, if necessary and desired, at the amino group and/or carboxyl group thereof with readily removable protecting groups. The readily removable protecting group for the amino group and/or carboxyl group may be for example, a trimethylsilyl group.

The carboxyl group may also be protected by forming salts with inorganic bases such as sodium salts or with organic bases such as triethylamine salts.

The compounds represented by general formula (II) may also be reacted with the compounds represented by general formula (III), namely acids, using suitable condensing agents, for example, N,N-dicyclohexylcarbodiimide, N-ethyl-5-phenylisoxazolium-3'-sulfonate, etc. Further, the acids may be converted into appropriate reactive derivatives followed by reacting with the compounds represented by general formula (II).

The appropriate reactive derivatives may be made of, for example, acid halides (e.g., acid chlorides), azides, acid anhydrides, particularly mixed acid anhydride with strong acids, active esters (e.g., N-hydroxysuccinimide ester) and active amides (e.g., imidazolide, triazolide).

The reaction between the compounds represented by general formula (II) and the compounds represented by general formula (III) is carried out generally in an inert solvent such as an organic solvent, e.g., dioxane, tetrahydrofuran, acetonitrile, chloroform, methylene ,chloride, ethyl acetate, dimethylformamide, etc. If necessary the reaction is carried out, in an aqueous solution, preferably in the presence of deacidifying agents. As the deacidifying agents, triethylamine, diethylaniline and the like are employed in the organic solvent system and, in the aqueous system, aqueous alkalis, preferably, sodium hydroxide, sodium hydrogen carbonate (sodium bicarbonate), potassium carbonate, etc. are employed.

The reaction may be carried out at temperatures ranging from about $-30°$ C. to room temperature, and preferably from $-10°$ C. to $10°$ C.

If necessary and desired, the protecting groups may be split off from the thus obtained cephalosporin derivatives represented by general formula (I).

The compounds represented by general formula (II) used in the process of the present invention can be prepared by reacting known 7-amino-cephalosporanic acid with 2-carboxy-7-mercapto 5-methyl-s-triazolo-[1,5-a]pyrimidine (Japanese Patent Application No. 247251 1983) or carboxyl-protected derivatives thereof, using as a solvent an organic solvent such as alcohols, dimethylformamide, acetonitrile, etc. or water. In the case that the reaction is carried out in organic solvents, it is preferred that the reaction be performed in the presence of Lewis acids such as boron trifluoride-ether complexes, etc. Further in the case that water is used as the solvent, the reaction can be carried out in the presence of an appropriate amount of aqueous alkalis such as sodium hydrogen carbonate, potassium carbonate, etc., or using buffers having a pH of 6.0 to 7.8 as the solvent. The reaction temperature may be in the range of about $40°$ C. to about $80°$ C., and preferably from $55°$ C. to $65°$ C. From the thus obtained compounds represented by general formula (II), the protecting groups can be split off, if necessary and desired.

Process B

The compounds represented by general formula (I) can be produced by reacting compounds represented by general formula (IV) that can be prepared in a conventional manner:

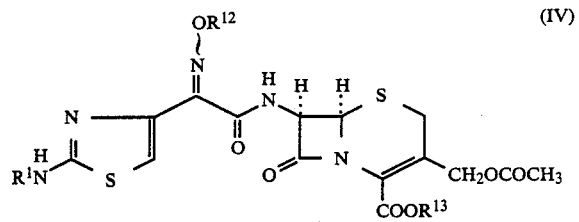

wherein $R^1$, $R^{12}$, $R^{13}$ and the wavy line have the same significance as defined hereinabove, provided that $R^{12}$ does not represent an acyl group, with thiol compounds represented by general formula (V):

$$HS-Z \qquad (V)$$

wherein Z has the same significance as defined hereinabove.

The reaction between the compounds represented by general formula (IV) and the compounds represented by general formula (V) can be carried out in organic polar solvents such as alcohol, dimethylformamide, etc. but is preferably carried out in an aqueous system. More preferably, the reaction is carried out in the presence of an appropriate amount of aqueous alkalis, e.g., sodium hydrogen carbonate or potassium carbonate, bonate, or carried out in a buffer under a pH condition of 6.0 to 7.8.

The reaction in this case can be carried out at temperatures in the range of about $40°$ C. to about $80°$ C., and preferably at from $55$ to $65°$ C.

From the thus obtained cephalosporin derivatives represented by general formula (I), the amino protecting groups thereof can be split off, if necessary and desired.

When $R^{12}$ represents an acyl group, the compounds represented by general formula (I) can be prepared as follows.

Process C

The compounds represented by general formula (I) can be produced by reacting compounds represented by general formula (VI):

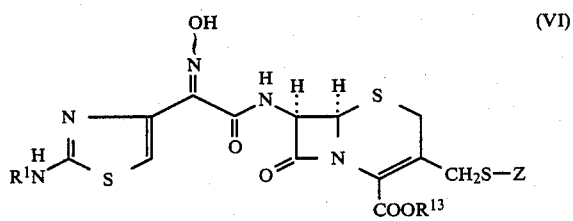

wherein $R^1$, $R^{13}$, Z and the wavy line have the same significance as defined hereinabove, with compounds represented by general formula (VII):

$$R^{12'}-OH \qquad (VII)$$

wherein $R^{12'}$ represents an acyl group.

The reaction can be carried out by reacting the compounds represented by general formula (VII), i.e., the acids, with the compounds represented by general formula (VI), using suitable condensing agents, e.g., N,N-dicyclohexylcarbodiimide, etc., or by converting the compounds represented by general formula, (VII) into appropriate reactive derivatives, e.g., acid halides, acid anhydrides, or into mixed acid anhydrides which are preferably prepared with strong acids, and then reacting the derivatives with the compounds represented by general formula (VI). In view of the reactivity, operability, etc., particularly preferred is the process in which the compounds represented by general formula (VII) are converted into the acid halides followed by reacting the acid halides with the compounds represented by general formula (VI).

The reaction between the compounds represented by general formula (VI) and the compounds represented by general formula (VII) is carried out generally in an inert solvent such as an organic solvent, e.g., dioxane, tetrahydrofuran, acetonitrile, chloroform, methylene chloride, ethyl acetate, dimethylformamide, etc., or, if desired, in water or a solvent mixture of water and organic solvents, preferably in the presence of deacidifying agents. As the deacidifying agents, triethylamine, diethylaniline and the like are employed in the organic solvents and, in the aqueous system, aqueous alkalis, preferably sodium hydroxide, sodium hydrogen carbonate, potassium carbonate and the like are employed.

The reaction can be conducted at temperatures of about $-30°$ C. to room temperature but it is preferred that the reaction be conducted at $-10°$ C. to $10°$ C.

From the thus obtained cephalosporin derivatives represented by general formula (I), the protecting groups thereof can be split off, if necessary and desired.

The compounds represented by general formula (VI) can be prepared by splitting the hydroxyl-protecting group off from the products produced in accordance with Process A.

The thiol compounds represented by general formula (V) which are intermediate compounds can be prepared as follows.

Process D

The thiol compounds can be obtained by reacting compounds represented by general formula (VIII):

X—Z  (VIII)

wherein X represents a halogen atom and Z has the same significance as defined hereinabove, with sodium hydrogen sulfide. The reaction may proceed generally in a polar solvent, e.g., alcohol or water, preferably in an aqueous system. The reaction may also be carried out at room temperature or with heating but room temperature is preferred.

Process E

The thiol compounds can also be obtained by reacting compounds represented by generally formula (IX):

HO—Z  (IX)

wherein Z has the same significance as defined hereinabove, with phosphorus pentasulfide. The reaction can be conducted generally at room temperature or with heating in a solvent such as xylene, toluene, pyridine, etc. The reaction is preferably conducted with heating, namely at about 80° to about 100° C. using pyridine as a solvent.

The 2-amino-4-thiazolyl-2-acyloxyiminoacetic acid derivatives represented by general formula (III) which are one of intermediates can be prepared as follows:

Process F

The acetic acid derivatives can be prepared by reacting known compounds represented by general formula (X):

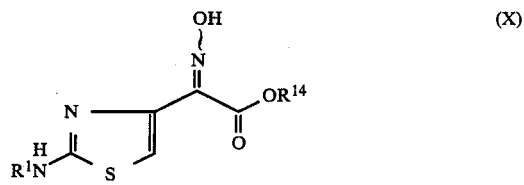

wherein the wavy line has the same significance as defined above; $R^1$ represents a hydrogen atom or an amino protecting group; and $R^{14}$ represents a hydrogen atom or a carboxyl protecting group, with compounds represented by general formula (VII):

$R^{12'}$—OH  (VII)

wherein $R^{12'}$ represents an acyl group.

The reaction can be carried out by reacting the compounds represented by general formula (VII), i.e., the acids, with the compounds represented by general formula (X), using suitable condensing agents, e.g., N,N-dicyclohexylcarbodiimide, etc., or by converting the compounds represented by general formula (VII) into appropriate reactive derivatives, e.g., acid halides, acid anhydrides, or into mixed acid anhydrides which are preferably prepared with strong acids, and then reacting the derivatives with the compounds represented by general formula (X). In view of the reactivity, operability, etc., particularly preferred is the process in which the compounds represented by general formula (VII) are converted into the acid halides followed by reacting the acid halides with the compounds represented by general formula (X).

The reaction between the compounds represented by general formula (X) and the compounds represented by general formula (VII) is carried out generally in an inert solvent such as an organic solvent, e.g., dioxane, tetrahydrofuran, acetonitrile, chloroform, methylene chloride, ethyl acetate, dimethylformamide, etc., or, if desired, in water or in a mixture of water and organic solvents, preferably in the presence of deacidifying agents. As the deacidifying agents, triethylamine, diethylaniline and the like are employed in the organic solvents and, in the aqueous system, aqueous alkalis, preferably sodium hydroxide, sodium hydrogen carbonate, potassium carbonate and the like are employed. The reaction can be conducted at temperatures ranging from about $-30°$ C. to room temperature, and preferably from $-10°$ C. to $10°$ C.

Process G

The acetic acid derivatives can be prepared by reacting compounds represented by genera formula (XI):

wherein $R^{14}$ represents a hydrogen atom or a carboxyl-protecting group, with compounds represented by general formula (VII):

$$R^{12'}-OH \quad \text{(VII)}$$

wherein $R^{12'}$ has the same significance as defined hereinabove, in the same manner as described above and then condensing the resulting product with thiourea derivatives represented by general formula (XII):

$$R^1NH-\overset{\overset{S}{\|}}{C}-NH_2 \quad \text{(XII)}$$

wherein $R^1$ has the same significance as defined hereinabove.

In this process, the condensation of the resulting product with the thiourea derivatives can be conducted generally in a solvent such as methanol, ethanol, tetrahydrofuran, dioxane, methylene chloride, ethylacetate, etc., preferably in the presence of a deacidifying agent such as triethylamine, dimethylaniline, potassium carbonate, sodium hydrogen carbonate, etc. The reaction is carried out at room temperature or under reflux.

To demonstrate the utility of the compounds of the present invention, data on antibacterial activity of representative compounds are shown below.

Compound 1: (6R,7R)-7-[2-(2-amino-4-thiazolyl)-2-(Z-methoxyimino)acetamido]-3-[(5-methyl-s-triazolo[1,5-a]pyrimidin-7-yl) oct-2-ene-2-carboxylic acid thio-methyl]-8-oxo-5-thia-1-azabicyclo[4.2.0]oct-2-ene-2-carboxylic acid Compound 2: (6R,7R)-7-[2-(2-amino-4-thiazolyl)-2-(Z-methoxyimino)acetamido]-3-[(2-carboxy-5-methyl-s-triazolo [1,5-a]pyrimidin-7-yl)thiomethyl]-8-oxo-5-thia-1-azabicyclo 4.2.0]oct-2-ene-2-carboxylic acid Compound 3: (6R,7R)-7-[2-(2-amino-4-thiazolyl)-2-(Z-methoxyimino)acetamido]-3-[(6-carboxy-s-triazolo [1,5-a]pyrimidin-7-yl)-thiomethyl]-8-oxo-5-thia-1-azabicyclo [4.2.0]oct-2-ene-2-carboxylic acid Compound 4: (6R,7R)-7-[2-(2-amino-4-thiazolyl)-2-(Z-methoxyimino)acetamido]-3-[(2-carboxymethyl-5-methyl-s-triazolo [1,5-a]-pyrimidin-7-yl)thiomethyl]-8-oxo-5-thia-1-azabicyclo [4.2.O]oct-2-ene-2-carboxylic acid Compound 5: (6R,7R)-7-[2-(2-amino-4-thiazolyl)-2-(Z-methoxyimino)acetamido]-3-](5-carboxymethyl-s-triazolo [1,5-a]pyrimidin-7-yl)thiomethyl]-8-oxo-5-thia-1-azabicyclo [4.2.0]oct-2-ene-2-carboxylic acid Compound 6: (6R,7R)-7-[2-(2-amino-4-thiazolyl)-2-(Z-methoxyimino)acetamido]-3-[(5-carboxy-s-triazolo [1,5-a]pyrimidin-7-yl)-thiomethyl]-8-oxo-5-thia-1-azabicyclo [4.2.0]oct-2-ene-2-carboxylic acid Compound 7: (6R,7R)-7-[2-(2-amino-4-thiazolyl)-2-(Z-methoxyimino)acetamido]-3-[(2,6-dicarboxy-s-triazolo [1,5-a]pyrimidin-7-yl)thiomethyl]-8-oxo-5-thia-1-azabicyclo [4.2.0]oct-2-ene-2-carboxylic acid Compound 8: (6R,7R)-7-[2-(2-amino-4-thiazolyl)-2-(Z-hydroxyimino)(acetamido]-3-[(2-carboxy-5-methyl-s-triazolo [1,5-a]pyrimidin-7-yl)thiomethyl]-8-oxo-5-thia-1-azabicyclo [4.2.O]oct-2-ene-2-carboxylic acid Compound 9: (6R,7R)-7-[2-(2-amino-4-thiazolyl)-2-[Z-(2-furancarbonyl)oxyimino]acetamido]-3-[(2-carboxy-5-methyl-s-triazolo [1,5-a]pyrimidin-7-yl)thiomethyl]-8-oxo-5-thia-1-azabicyclo[4.2.0]oct-2-ene-2-carboxylic acid Compound 10: (6R,7R)-7-[2-(2-amino-4-thiazolyl)-2-[Z-(2-thiopenecarbonyl)oxyimino]acetamido]-3-[(2-carboxy-5-methyl-s-triazolo [1,5-a]pyrimidin-7-yl)-thiomethyl]-8-oxo-5-thia-1-azabicyclo [4.2.0]-oct-2-ene-2-carboxylic acid Compound 11: (6R,7R)-7-[2-(2-amino-4-thiazolyl)-2-[Z-(3-pyridinecarbonyl)oxyimino]acetamido-3-[(2-carboxy-5-methyl-s-trizolo [1,5-a]pyrimidin-7-yl)thiomethyl]-8-oxo-5-thia-1-azabicyclo [4.2.0]oct-2-ene-2-carboxylic acid Compound 12: (6R,7R)-7-[2-(2-amino-4-thiazolyl)-2-[Z-(3,4-methylenedioxybenzoyl)oxyimino]-acetamido]-3-[(2-carboxy-5-methyl-s-triazolo [1,5-a]pyrimidin-7-yl)thiomethyl]-8-oxo-5-thia-1-azabicyclo [4.2.0]oct-2-ene-2-carboxylic acid Compound 13: (6R,7R)-7-[2-(2-amino-4-thiazolyl)-2-[Z-(3,4,5-triacetoxybenzoyl)oxyimino]acetamido]-3-[(2-carboxy-5-methyl-s-triazolo [1,5-a]pyrimidin-7-yl)-thiomethyl]-8-oxo-5-thia-1-azabicyclo [4.2.0]oct-2-ene-2-carboxylic acid Compound 14: (6R,7R)-7-[2-(2-amino-4-thiazolyl)-2-(Z-methylimino)acetamido]-3-[(2-carboxy-s-triazolo [1,5-a]pyrimidin-7-yl)-thiomethyl]8-oxo-5-thia-1-azabicyclo-[4.2.0]oct-2-ene-2-carboxylic acid Compound 15: (6R,7R)-7-[2-(2-amino-4-thiazolyl)-2-(Z-methoxyimino)acetamido]-3-[(2-carboxy-5-hydroxy-s-triazolo [1,5-a]pyrimidin-7-yl)thiomethyl]-8-oxo-5-thia-1-azabicyclo [4.2.0]oct-2-ene-2-carboxylic acid Compound 16: (6R,7R)-7-[2-(2-amino-4-thiazolyl)-2(Z-methoxyimino)acetamido]-3-[(5-methoxy-s-triazolo [1,5-a]pyrimidin-7-yl)-thiomethyl]-8-oxo-5-thia-1-azabicyclo-[4.2.0]oct-2-ene-2-carboxylic acid Compound 17: (6R,7R)-7-[2-(2-amino-4-thiazolyl)-2-(Z-methoxyimino)acetamido]-3-[(2-amino-5-a]pyrimidin-7-yl) thiomethyl]-8-oxo-5-thia-1-azabicyclo [4.2.0]oct-2-ene-2-carboxylic acid Compound 18: (6R,7R)-7-[2-(2-amino-4-thiazolyl)-2-(Z-methoxyimino)acetamido]-3-[(2-hydroxysulfonyl-5-methyl-s-triazolo [1,5-a]pyrimidin-7-yl)thiomethyl]-8-oxo-5thia-1-azabicyclo [4.2.0]oct-2-ene-2-carboxylic acid Compound 19: (6R,7R)-7-[2-(2-amino-4-thiazolyl)-2-(Z-methoxyimino)acetamido]-3-[(6-carboxy-7-hydroxy-s-triazolo [1,5-a]pyrimidin-2-yl)thiomethyl]-8-oxo-5-thia-1-azabicyclo [4.2.0]oct-2-ene-2-carboxylic acid Compound 20: (6R,7R)-7-[2-(2-amino-4-thiazolyl)-2-(Z-methoxyimino)acetamido]-3-[7-carboxy-3-methyl-s-triazolo [4,3-a]pyrimidin-5-yl)thiomethyl]-8-oxo-5-thia-1-azabicyclo [4.2.0]oct-2-ene-2-carboxylic acid Compound 21: (6R,7R)-7-[2-(2-amino-4-thiazolyl)-2-(Z-methoxyimino)acetamido]-3-[(7-carboxy-5-hydroxy-s-triazolo [4,3-a]pyrimidin-3-yl)thiomethyl]-8-oxo-5-thia-1-azabicyclo [4.2.0]oct-2-ene-2-carboxylic acid Compound 22: (6R,7R)-7-[2-(2-amino-4-thiazolyl)-2-(Z-methoxyimino)acetamido]-3-[(7-s-triazolo [1,5-c]pyrimidin-5-yl)thiomethyl]-8-oxo-5-thia-1-azabicyclo [4.2.0]oct-2-ene-2-carboxylic acid Compound 23: (6R,7R)-7-[2-(2-amino-4-thiazolyl)-2-)Z-methoxyimino)acetamido]-3-[(5-hydroxy-7-methyl-s-triazolo [4,3-c]pyrimidin-3-yl)thiomethyl]-8-oxo-5-thia-1-azabicyclo [4.2.0]oct-2-ene-2-carboxylic acid Compound 24: (6R,7R)-7-[2-(2-amino-4-thiazolyl)-2-(Z-methoxyimino)acetamido]-3-[(7-methyl-5-oxo-5H-1,3,4-thiadiazolo [3,2-a]pyrimidin-2-yl)thiomethyl]-8-oxo-5-thia-1-azabicyclo 4.2.0]oct-2-ene-2-carboxylic acid Compound 25: (6R,7R)-7-[2-(2-amino-4-thiazolyl)-2-(Z-benzoyloxyimino)acetamido]-3-[(2-carboxy-5-methyl-s-triazolo [1,5-a]pyrimidin-7-yl)thiomethyl]-8-oxo-5-thia-1-azabicyclo [4.2.0]oct-2-ene-2-carboxylic acid Compound 26: (6R,7R)-7-[2-(2-amino-4-thiazolyl)-2-[Z-(2-pyrrolecarbonyl)oxyimino]acetamido]-3-[(2-carboxy-5methyl-s-triazolo [1,5-a]pyrimidin-7-yl)thiomethyl]-8-oxo-5-thia-1-azabicyclo[4.2.0]oct-2-ene-2-carboxylic acid Compound 27: (6R,7R)-7-[2-(2-amino-4-thiazolyl)-2-[Z-(3,4-diacetoxybenzoyl)oxyimino]-acetamido]-3-[(2-carboxy-5-methyl-s-triazolo [1,5-a]pyrimidin-7-yl)thiomethyl]-8-oxo-5-thia-1-azabicyclo-[4.2.0.]oct-2-ene-2-carboxylic acid

EXPERIMENTAL EXAMPLE 1

Antibacterial activity in vitro was determined in accordance with the agar plate dilution method.

A platinum loop each of test bacteria ($10^6$ cells/ml), cultured in Mueller Hinton broth, was inoculated on Mueller Hinton agar plates which contained test compounds at various concentrations. After cultivating at 37° C. for 20 hours, the minimum inhibitory concentration (MIC μg/ml) was determined.

The results ar shown in Tables 1-a and 1-b.

TABLE 1-a

| Compound Number | (MIC μg/ml) | | | | | |
|---|---|---|---|---|---|---|
| | Staphylococcus aureus Smith | Escherichia coli 67 | Serratia marcescens IFO3759 | Klebsiella pneumoniae IFO3317 | Proteus morganii IFO3848 | Pseudomonas aeruginosa IFO3445 |
| 1 | 1.57 | <0.05 | 0.2 | <0.05 | 0.78 | 50 |
| 2 | 1.57 | <0.05 | <0.05 | <0.05 | 0.2 | 12.5 |
| 3 | 12.5 | 0.39 | 0.78 | <0.05 | 1.57 | >100 |
| 4 | 3.13 | 0.2 | 0.1 | <0.05 | 0.78 | 25 |
| 5 | 3.13 | 0.1 | 0.2 | <0.05 | 0.78 | >100 |
| 6 | 1.57 | <0.05 | 0.2 | <0.05 | 0.2 | 6.25 |
| 7 | 12.5 | <0.05 | 0.39 | <0.05 | 0.39 | >100 |
| 8 | 0.78 | 0.2 | 0.2 | <0.05 | 0.39 | >100 |
| 9 | 0.39 | <0.05 | <0.05 | <0.05 | 0.2 | 100 |
| 10 | 0.39 | 0.1 | 0.1 | <0.05 | 0.39 | 50 |
| 11 | 0.39 | <0.05 | <0.05 | <0.05 | 0.1 | >100 |
| 12 | 0.78 | 0.39 | 0.39 | 0.39 | 0.78 | 25 |
| 13 | 0.78 | 0.05 | <0.05 | <0.05 | 0.2 | 1.57 |

TABLE 1-b

| Compound Number | (MIC μg/ml) | | | | | |
|---|---|---|---|---|---|---|
| | Staphylococcus aureus Smith | Escherichia coli 67 | Serratia marcescens IFO3759 | Klebsiella pneumoniae IFO3317 | Proteus morganii IFO3848 | Pseudomonas aeruginosa IFO3445 |
| 14 | 3.13 | 0.1 | <0.05 | <0.05 | 0.2 | 50 |
| 15 | 12.5 | 0.39 | 0.1 | <0.05 | 0.78 | 12.5 |
| 16 | 1.57 | 0.1 | 0.39 | <0.05 | 3.13 | 100 |
| 17 | 1.57 | 0.1 | 0.2 | <0.05 | 0.39 | 50 |
| 18 | 0.39 | <0.05 | 0.2 | <0.05 | 0.78 | 100 |
| 19 | 6.25 | <0.05 | <0.05 | <0.05 | 0.2 | 6.25 |
| 20 | 3.13 | 0.2 | 0.2 | <0.05 | 0.78 | 12.5 |
| 21 | 25 | 0.78 | 1.57 | 0.1 | 3.13 | >100 |
| 22 | 1.57 | 0.1 | 0.39 | <0.05 | 0.78 | 50 |
| 23 | 3.13 | 0.1 | 0.39 | <0.05 | 0.78 | 50 |
| 24 | 0.78 | <0.05 | 0.2 | <0.05 | 0.39 | 50 |
| 25 | 0.39 | 0.1 | 0.1 | <0.05 | 0.39 | 50 |
| 26 | 1.57 | 0.2 | 0.2 | <0.05 | 0.78 | 25 |
| 27 | 1.57 | <0.05 | <0.05 | <0.05 | 0.2 | 0.39 |

EXPERIMENTAL EXAMPLE 2

Protection ability against systemic infection was determined as follows. An aqueous suspension of test bacteria was intraperitoneally injected into groups of 10 four week old ICR mice. One hour after the infection, test compounds were intravenously administered. The number of surviving mice was counted 1 week after injection to determine the dose at which 50% of the test animals were alive ($ED_{50}$: mg/kg).

The results are shown in Tables 2-a through 2-b.

TABLE 2-a

| Compound Number | $ED_{50}$ (mg/Kg) | | |
|---|---|---|---|
| | Escherichia coli 67 | Klebsiella pneumoniae IF03317 | Pseudomonas aeruginosa IF03445 |
| 1 | 0.7 | 0.1 | 780 |
| 2 | 0.8 | 0.1 | 360 |
| 6 | 0.8 | 0.1 | 230 |

TABLE 2-b

| Compound Number | $ED_{50}$ (mg/Kg) | | |
|---|---|---|---|
| | Escherichia coli 67 | Klebsiella pneumoniae IF03317 | Staphylococcus 242* |
| 8 | — | 7.68 | 3.55 |
| 9 | — | 7.68 | 2.11 |
| 10 | — | — | 8.01 |
| CEZ | — | — | 74 |

*Methicillin-resistant strain

Next, $LD_{50}$ of representative examples of the compounds of the present invention is shown in Table 3 wherein $LD_{50}$ was determined in accordance with the Probit method.

TABLE 3

| Compound No. | $LD_{50}$ (mg/Kg)iv |
|---|---|
| 1 | >1000 |
| 2 | >1000 |

TABLE 3-continued

| Compound No. | LD$_{50}$ (mg/Kg)iv |
| --- | --- |
| 6 | >1000 |
| 8 | >1000 |
| 9 | >1000 |
| 10 | >1000 |

The compounds of the present invention are useful for the treatment of infectious diseases caused by gram-positive bacteria such as *Staphylococcus aureus, streptococci*, etc., or by gram-negative bacteria such as *Escherichia coli, Klebsiella pneumoniae, Proteus mirabilis, Proteus morganii, Serratia marcescens, Pseudomonas aeruginosa, Citrobacter, Enterobacter, Flavobacter*, etc.

The cephalosporin derivatives provided by the present invention can be employed as pharmaceutical compositions, for example, in the form of pharmaceutical compositions containing the cephalosporin derivatives together with appropriate, pharmaceutically acceptable carriers. The pharmaceutical composition may take a solid form (for example, tablets, capsules, etc.) or a liquid form (for example, injections, etc.). The compositions may be sterilized and may contain auxiliary agents generally employed in the pharmaceutical art.

Further, it is preferred to use the compounds after they are formed into freeze-dried products or powders followed by dissolving them in a conventional solvent, e.g., water or physiological saline, for use. The compounds can be used orally or parenterally. While dose varies depending upon age and conditions of the patient, conditions and kind of diseases, etc., from about 0.1 to about 10 g, preferably from about 0.2 to about 5 g, can be used as a daily dose for an adult. Parenteral administration of the compounds provided by the present invention is particularly preferred.

Hereafter the present invention will be described with reference to the examples below, but is not deemed to be limited thereto.

EXAMPLE 1

Preparation of 2-carboxy-7-mercapto-5-methyl-s-triazolo [1,5-a]pyrimidine (Step 1)

Preparation of 7-chloro-2-methoxycarbonyl-5-methyl-s-triazolo [1,5-a]pyrimidine.

7-Hydroxy-2-methoxycarbonyl-5-methyl-s-triazolo-[1,5-a]pyrimidine (23 g) was suspended under ice cooling in 250 ml of phosphorus oxychloride, 14 ml of N,N-dimethylaniline was added dropwise to this suspension over a period of five minutes under ice cooling, the mixture was stirred at room temperature for ten minutes and then refluxed for five hours. After removing excess phosphorus oxychloride by distillation from the reddish brown solution under normal pressure, about 50 ml of a reddish brown oil was obtained. It was shaken with 300 ml of dichloromethane and 200 ml of water, the organic layer was collected, and the red aqueous layer was extracted with 200 ml of dichloromethane. The organic layers were joined together, washed with saturated sodium bicarbonate solution until the pH of the washings rose to 7-8, then with 100 ml of saturated sodium chloride solution. After drying over anhydrous magnesium sulfate, the red solution was concentrated to about 30 ml, and 30 ml of n-hexane was added to the concentrate for recrystallization, affording 18 g of the objective compound as faint yellow crystals.

(Step 2)

Preparation of 2-carboxy-7-mercapto-5-methyl-s-triazolo [1,5-a]pyrimidine.

The product obtained in Step 1 (17 g) was added at a time, in a nitrogen atmosphere, to a solution of sodium hydrosulfide (16 g) in 280 ml of water at room temperature with stirring, and the mixture was heated to 60° C. with stirring continued. The resultant yellow solution was cooled to room temperature, the insoluble matters were filtered off, the filtrate was acidified with concentrated hydrochloric acid to pH 2.0, and the crystals thus formed were collected by filtration and washed twice with 20 ml of water, affording 10 g of the objective compound as yellow crystals. M.P.: 215.4°–217.3° C.

EXAMPLE 2

Preparation of 6-carboxy-7-mercapto-s-triazolo-[1,5-a]pyrimidine (Step 1)

Preparation of 7-chloro-6-ethoxycarbonyl-s-triazolo [1,5-a]pyrimidine

A suspension of 6-ethoxycarbonyl-7-hydroxy-s-triazolo [1,5-a]pyrimidine (7 g) in phosphorus oxychloride (20 ml) was refluxed for 30 minutes, the resultant orange solution was further refluxed for one hour, and excess phosphorus oxychloride was removed by distillation under reduced pressure. Benzene (50 ml) was added to the residue, and remaining phosphorus oxychloride was completely removed by azeotropic distillation under reduced pressure. Chloroform (80 ml) was added to the residue, the insoluble matters were filtered off, and the solvent was removed in vacuo from the filtrate. Purification of the brown residue by silica gel column chromatography gave 3.9 g of the objective compound as colorless crystals.

M.P.: 130.0°–132.0° C.

NMR (DMSO-d$_6$, δ):

9.3 (1H, s), 8.6 (1H, s), 4.5 (2H, q), 1.5 (3H, t).

(Step 2)

Preparation of 6-ethoxycarbonyl-7-mercapto-s-triazolo [1,5-a]pyrimidine

The product obtained in Step 1 (3.6 g) and sodium hydrosulfide (2.5 g) were dissolved in 50 ml of water, the solution was stirred at room temperature for 20 minutes, its pH was lowered to 1.0 with 6N hydrochloric acid, and the crystals thus formed were collected by filtration, affording 3.0 g of the objective compound as yellow crystals.

NMR (DMSO-d$_6$, δ):

8.7 (1H, s), 8.4 (1H, s), 4.3 (2H, q), 1.3 (3H, t).

(Step 3)

Preparation of 6-carboxy-7-mercapto-s-triazolo[1,5-a]pyrimidine

The product obtained in Step 2 (2.4 g) was dissolved in 50 ml of aqueous solution containing 1.0 g potassium hydroxide, the solution was heated at 80° C. for one hour, the insoluble matters were filtered off, and the clear, faint yellow filtrate was washed with 30 ml ethyl acetate. The pH of the aqueous layer was lowered to 1.0 with concentrated hydrochloric acid, and the crystals thus formed were collected by filtration, affording 2.0 g of the objective compound as colorless crystals.

M.P.: 247.0°–249.0° C.

NMR (DMSO-d$_6$, δ): 9.0 (1H, s), 8.9 (1H, s).

EXAMPLE 3

Preparation of 2-carboxymethyl-7-mercapto-5-methyl-s-triazolo [1,5-a]pyrimidine (Step 1)

Preparation of 2-cyanomethyl-5-methyl-7-hydroxy-s-triazolo [1,5-a]pyrimidine,

2-Chloromethyl-5-methyl-7-hydroxy-s-triazolo[1,5-a]pyrimidine (4 g) was added to a solution of 2 g of sodium cyanide in 10 ml of dimethylformamide with stirring, and the mixture was heated at 50° C. for two hours and then at 80° C. for three hours. After cooling, 60 ml of 6N hydrochloric acid was added, the mixture was extracted with 100 ml ethyl acetate, the organic layer was concentrated under reduced pressure, and the crystals thus formed were collected and washed with an ethyl acetate/ether mixed solvent, affording 2.4 g of the objective compound.
M.P 277.5°–278.5° C.

(Step 2)

Preparation of 2-carboxymethyl-7-hydroxy-5-methyl-s-triazolo [1,5-a]pyrimidine.

The product obtained in Step 1 (2.1 g) was dissolved in 10 ml of concentrated hydrochloric acid, the solution was refluxed for 20 minutes, 200 ml of water was added, and the crystals thus separated were collected by filtration and washed with a methanol/ether mixed solvent, affording 1.5 g of the objective compound.
M.P.: 266.5°–270.0° C.

(Step 3)

Preparation of 7-hydroxy-2-methoxycarbonylmethyl-5-methyl-s-triazolo[1,5-a]pyrimidine A solution of the product obtained in Step 2 (1.5 g) in 50 ml of methanol was cooled to 0° C., 24 ml of thionyl chloride was added dropwise to this solution at that temperature, and the mixture was refluxed for 1.5 hours. After removing the solvent by distillation under reduced pressure, the residue was recrystallized from ethyl acetate/ether, giving 1.5 g of the objective compounds.
M.P.: 224.5°–226.5° C.

(Step 4)

Preparation of 7-chloro-2-methoxycarbonylmethyl-5-methyl-s-triazolo[1,5-a]pyrimidine A solution of the product obtained in Step 3 (1.5 g) in 15 ml of phosphorus oxychloride was refluxed for two hours, excess phosphorus oxychloride was distilled off, the residue was dissolved in chloroform, and the solution was washed with ice water. After removing the solvent from the organic layer under reduced pressure, the residue was purified by silica gel chromatography, affording 1 g of the objective compound.
M.P.: 111.0°–111.5° C.

(Step 5)

Preparation of 7-mercapto-2-methoxycarbonylmethyl-5-methyl-s-triazolo[1,5-a]pyrimidine The product obtained in Step 4 (2 g) and sodium hydrosulfide (1.22 g) were dissolved in 35 ml of water, the solution was stirred at room temperature for 1.5 hours under a nitrogen stream, and the insoluble matters were filtered off. The filtrate was cooled to 0° C., its pH was lowered to 1–2 with 6N hydrochloric acid, the slurry was stirred at that temperature for 30 minutes, and the crystals thus formed were collected by filtration, washed with 30 ml of water and dried, affording 1.44 g of the objective compound.
M.P.: 213.0°–214.0° C.

(Step 6)

Preparation of 2-carboxymethyl-7-mercapto-5-methyl-s-triazolo[1,5-a]pyrimidine

The product obtained in Step 5 (1.5 g) was added to a solution of 0.75 g potassium hydroxide in 10 ml of water, the mixture was stirred at room temperature for two hours, and its pH was lowered to 1–2 with 6N hydrochloric acid. The crystals thus formed were collected by filtration, washed with 50 ml of water and dried, giving 1.3 g of the objective compound.
M.P.: 253.0°–255.0° C.

EXAMPLE 4

Preparation of 5-carboxymethyl-7-mercapto-s-triazolo[1,5-a]pyrimidine (Step 1)

Preparation of 5-ethoxycarbonylmethyl-7-hydroxy-s-triazolo[1,5-a]pyrimidine

A suspension of 3-amino-s-triazole (28 g) and diethyl acetonedicarboxylate (100 g) in 100 ml of acetic acid was refluxed for six hours. After cooling to room temperature, 150 ml of concentrated hydrochloric acid was added under ice cooling, the crystals thus formed were collected by filtration, and washed twice with 100 ml of ethanol, then once with 100 ml of ether, affording 71 g of the objective compound as colorless crystals.
NMR (DMSO-$d_6$, $\delta$)
13.2 (1H, s), 8.3 (1H, s), 6.0 (1H, s), 4.2 (2H, q), 3.9 (2H, s), 1.2 (3H, t).

(Step 2)

Preparation of 7-chloro-5-ethoxycarbonylmethyl-s-triazolo[1,5-a]pyrimidine

The product obtained in Step 1 (30 g) was suspended in 300 ml of phosphorus oxychloride, 19 ml of N,N-dimethylaniline was added dropwise to this suspension over a period of five minutes, and the mixture was heated at 50° C. for three hours. Excess phosphorus oxychloride was removed from the reddish brown solution under reduced pressure and about 70 ml of a reddish brown oil was obtained. It was dissolved in 200 ml of dichloromethane, and saturated sodium bicarbonate solution was added to this solution under ice cooling to adjust the pH to 7.5. The reddish brown aqueous layer was separated, extracted thrice with 100 ml of dichloromethane, the extract was joined with the dichloromethane solution separated above, the combined organic solution was washed with 10 ml of saturated sodium chloride solution, and dried over anhydrous magnesium sulfate. The dried filtrate was concentrated to about 40 ml under reduced pressure, affording 25 g of the objective compound as yellow oil.
NMR (DMSO-$d_6$, $\delta$):
8.5 (1H, s), 7.4 (1H, s), 4.2 (2H, q), 4.0 (2H, s), 1.3 (3H, q).

(Step 3)

Preparation of 5-ethoxycarbonylmethyl-7-mercapto-s-triazolo[1,5-a]pyrimidine

The product obtained in Step 2 (24 g) was added all at once, under a nitrogen stream, to a solution of 23 g sodium hydrosulfide in 600 ml of water, the mixture was stirred at room temperature for two hours, and the insoluble matters were filtered off. The filtrate was acidified to pH 2.0 with concentrated hydrochloric acid, and the crystals thus formed were collected by filtration, washed twice with 40 ml of water and dried, affording 22 g of the objective compound as yellow crystals.

NMR (DMSO-$d_6$,$\delta$):
12.9 (1H, bs), 8.8 (1H, s), 7.1 (1H, s), 4.1 (2H, q), 3.8 (2H, s), 1.2 (3H, t).

(Step 4)

Preparation of 5-carboxymethyl-7-mercapto-s-triazolo[1,5-a]pyrimidine

The product obtained in Step 3 (20 g) was added to a solution of 10 g of potassium hydroxide in 200 ml of water, the mixture was heated at 60° C. for two hours. After cooling the resulting yellow solution, its pH was lowered to 2.0,with concentrated hydrochloric acid, and the yellow crystals thus formed were collected by filtration, washed twice with 30 ml of water and dried, giving 13 g of the objective compound as yellow crystals. M.P.: 283.0°–286° C.

EXAMPLE 5

Preparation of 5-carboxy-7-mercapto-s-triazolo[1,5-a]pyrimidine (Step 1)

Preparation of 7-chloro-5-ethoxycarbonyl-s-triazolo[1,5-a]pyrimidine

A suspension of 5-ethoxycarbonyl-7-hydroxy-s-triazolo[1,5-a]pyrimidine (6.8 g) in 40 ml of phosphorus oxychloride was heated at 60° C. with stirring, the resultant clear, orange solution was further refluxed for one hour, excess phosphorus oxychloride was distilled off, the brown residue was dissolved in 100 ml of chloroform, and the solution was slowly added to 100 ml of water with stirring. The chloroform solution was separated, dried over anhydrous sodium sulfate, the solvent was removed by distillation under reduced pressure, and the residue was purified by silica gel chromatography, affording 4.6 g of the objective compound as colorless crystals.

M.P.: 92.5°–94.0° C.
NMR (DMSO-$d_6$,$\delta$):
8.8 (1H, s), 7.9 (1H, s), 4.5 (2H, q), 1.4 (3H, t).

(Step 2)

Preparation of 5-ethoxycarbonyl-7-mercapto-s-triazolo[1,5-a]pyrimidine

The product obtained in Step 1 (4.1 g) and sodium hydrosulfide (2.6 g) were dissolved in 30 ml of water, the solution was refluxed for one hour, the reaction mixture was cooled to room temperature, its pH was lowered to 1.0 with 6N hydrochloric acid, and the colorless crystals thus formed were collected by filtration, giving 2.8 g of the objective compound.

M.P : 187.5°–189.0° C.
NMR (DMSO-$d_6$,$\delta$):
8.3 (1H, s), 7.1 (1H, s), 4.4 (2H, q), 1.4 (3H, t)

(Step 3)

Preparation of 5-carboxy-7-mercapto-s-triazolo[1,5-a]pyrimidine

The product obtained in Step 2 (2.0 g) was dissolved in a solution of 1.0 g potassium hydroxide in 80 ml of water, the mixture was heated at 80° C. for 30 minutes. After cooling the resulting orange solution to room temperature, it was washed with 50 ml of ethyl acetate, the pH of the aqueous layer was lowered to 1.0 with 6N hydrochloric acid, and the crystals thus formed were collected by filtration, washed with 50 ml of acetone, giving 1.6 g of the objective compound as orange crystals.

M.P.: 230.5°–232.0° C.
NMR (DMSO-$d_6$,$\delta$):
8.3 (1H, s), 7.1 (1H, s)

EXAMPLE 6

Preparation of 2,6-dicarboxy-7-mercapto-s-triazolo[1,5-a]pyrimidine (Step 1)

Preparation of 6-ethoxycarbonyl-7-hydroxy-2-methoxycarbonyl-s-triazolo[1,5-a]pyrimidine A mixture of methyl 3-amino-s-triazolocarboxylate (18 g), diethyl ethoxymethylenemalonate (27 g) and 50 ml of acetic acid was refluxed for three hours. The crystals formed upon cooling with ice were collected by filtration, and recrystallized from 50 ml of acetic acid, affording 40 g of the objective compound as colorless crystals.

NMR (DMSO-$d_6$,$\delta$):
8.2 (1H, s), 4.3 (2H, q), 3.9 (3H, s), 1.3 (3H, t).

(Step 2)

Preparation of 7-chloro-6-ethoxycarbonyl-2-methoxycarbonyl-s-triazolo[1,5-a]pyrimidine The product obtained in Step 1 (12 g) was suspended in 100 ml of phosphorus oxychloride, 5.9 g of N,N-dimethylaniline was added dropwise to this suspension at 0° C. with stirring over a period of ten minutes, and the mixture was stirred at room temperature for 30 minutes and then refluxed for four hours. Removing excess phosphorus oxychloride by distillation under normal pressure gave about 50 ml of a reddish brown oil. It was dissolved in 300 ml of dichloromethane, the solution was washed with 500 ml of saturated sodium bicarbonate solution, then with 80 ml of saturated sodium chloride solution, and the organic layer was dried over anhydrous magnesium sulfate. The dried reddish yellow filtrate was concentrated to about 30 ml, and crystallized from 20 ml of n-hexane, affording 8.5 g of the objective compound as faint yellow crystals.

M.P.: 149.0°–151.8° C.
NMR (DMSO-$d_6$,$\delta$):
8.7 (1H, s), 4.3 (2H, q), 3.4 (3H, s), 1.3 (3H, t).

(Step 3)

Preparation of 2,6-dicarboxy-7-mercapto-s-triazolo[1,5-a]pyrimidine

The product obtained in Step 2 was added at a all at once, under a nitrogen stream, to a solution of 5 g of sodium hydrosulfide in 150 ml of water, the mixture was stirred at room temperature for three hours, and 4 g of potassium hydroxide was added to the yellow slurry. This mixture was heated at 60° C. for three hours, and the insoluble matters were filtered off after cooling to room temperature. The orange filtrate was acidified to pH 2.0 with concentrated hydrochloric acid, the crystals thus formed were collected by filtration, washed twice with 10 ml of water and dried, affording 4.0 g of the objective compound as yellow crystals.

M.P.: 292.4°–294.8° C. (dec)

EXAMPLE 7

Preparation of (6R,7R)-7-[2-(2-amino-4-thiazolyl)-2-(Z-methoxyimino)acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid (Compound 2)

(Step 1)

Preparation of (6R,7R)-3-acetoxymethyl-7-[2-(2-chloroacetamido-4-thiazolyl)-2-(Z-methoxyimino)acetamido]-8-oxo-5-thia-1-azabicyclo[4.2.0]oct-2-ene-2-carboxylic acid Triethylamine (14 ml) was added to a solution of 23 g of 2-(2-chloroacetamido-4-thiazolyl)-2-(Z-methoxyimino)acetic acid in 100 ml of dichloromethane, and 17.3 g of phosphorus pentachloride was then added dropwise at 0° C. over a period of ten minutes. After stirring the mixture at 0° C. for ten minutes and then at room temperature for one hour, dichloromethane was removed by distillation under reduced pressure, the residue was washed twice with 30 ml of n-hexane to remove excess phosphorus pentachloride, the brown solid left was dissolved in 100 ml of tetrahydrofuran, and the phosphorus pentachloride still left was removed by filtration. This acid chloride solution in tetrahydrofuran was added dropwise under ice cooling over a period of 20 minutes to an ice-cooled solution of 20.3 g of 7-aminocephalosporanic acid and 19 g of bis(trimethylsilyl)acetamide in 150 ml of dry dichloromethane, and the mixture was stirred at room temperature for two hours. After removing the solvent by distillation under reduced pressure, the brown residue was added to a mixture of 250 ml of ethyl acetate and 80 ml of water, and the pH was adjusted to 7.5 with sodium bicarbonate, followed by washing with ethyl acetate. The aqueous layer was collected, its pH was lowered to 2.0 with 1N hydrochloric acid, the crystals thus formed were collected by filtration, washed twice with 50 ml of water and then once with 50 ml of 50% aqueous acetone, and thoroughly dried, giving 32 g of the objective compound as colorless crystals.

IR (KBr, cm-1):
1780, 1550, 1235, 1040.

NMR (DMSO-$d_6$, $\delta$):
9.5 (1H, d, 8 Hz), 8.1 (1H, s), 6.8 (1H, s), 4.7 (2H, s), 3.9 (3H, s), 2.0 (3H, s).

(Step 2)

Preparation of (6R,7R)-3-acetoxymethyl-7-[2-(2-amino-4-thiazolyl)-2-(Z-methoxyimino)acetamido]-8-oxo-5-thia-1-azabicyclo[4.2.0]oct-2-ene-2-carboxylic acid The product obtained in Step 1 (10.2 g) was dissolved in 80 ml of dimethylacetamide, 2.8 g of thiourea was added to this solution at room temperature in small portions over a period of ten minutes, and the mixture was stirred at room temperature for an additional three hours. After concentration of the reaction mixture under reduced pressure, 200 ml of ethyl acetate and 80 ml of water were added to the brown residue, the pH was adjusted to 7.8 with sodium bicarbonate, and the aqueous layer was washed with ethyl acetate until no thiourea could be detected in the aqueous layer. The pH of aqueous layer was lowered to 2.0, the crystals thus formed were collected by filtration, washed twice with 30 ml of water and then once with 10 ml of 50% aqueous acetone, and dried, giving 5.5 g of the objective compound as colorless crystals.

IR (KBr, cm-1):
1770, 1735, 1530, 1240, 1040.

NMR (DMSO-$d_6$, $\delta$):
9.5 (1H, d, 7 Hz), 6.7 (1H, s), 3.8 (3H, s), 2.0 (3H, s).

(Step 3)

Preparation of (6R,7R)-7-[2-(2-amino-4-thiazolyl)-2-(Z-methoxyimino)acetamido]-3-[(2-carboxy-5-methyl-s-triazolo[1,5-a]pyrimidin-7-yl)thiomethyl]-8-oxo-5-thia-1-azabicyclo-[4.2.0]oct-2-ene-2-carboxylic acid A suspension of the product obtained in Example 1 (2.1 g) and sodium bicarbonate (2.5 g) in 100 ml of 0.1 M phosphate buffer (pH 6.4) was heated with stirring, and the product obtained in Step 2 (4.6 g) was added to this suspension over a period of 20 minutes. The mixture was then heated to 60° C., and stirred at this temperature for five hours while maintaining the pH between 6.8 and 7.2. At the end of reaction, the resulting solution was allowed to cool to room temperature, washed twice with 100 ml of ethyl acetate, and the pH of the brown aqueous layer was lowered to 2.0 with 1N hydrochloric acid. The formed crystals were collected by filtration, washed twice with 30 ml of water, then once with 15 ml of 50% aqueous acetone, giving the objective compound as colorless crystals.

IR (KBr, cm-1): 1770, 1625, 1510, 1040.

NMR (DMSO-$d_6$, $\delta$):
9.6 (1H, d, 8 Hz), 7.4 (1H, s), 6.7 (1H, s), 5.8 (1H, dd, 8 Hz, 5 Hz), 5.2 (1H, d, 5 Hz), 4.5 (2H, ABq), 3.8 (3H, s), 3.7 (2H, ABq), 2.6 (3H, s).

EXAMPLE 8

Preparation of (6R,7R)-7-[2-(2-amino-4-thiazolyl)-2-(Z-methoxyimino)acetamido]-3-[(5-methyl-s-triazolo[1,5-a]pyrimidin-7-yl)thiomethyl]-8-oxo-5-thia- -azabicyclo[4.2.0]oct-2-ene-2-carboxylic acid (Compound 1)

(Step 1)

Preparation of (6R,7R)-7-amino-3-[(5-methyl-s-triazolo[1,5-a]pyrimidin-7-yl)thiomethyl]-8-oxo-5-thia-1-azabicyclo[4.2.0]oct-2-ene-2-carboxylic acid A suspension of 7-mercapto-5-methyl-s-triazolo[1,5-a]pyrimidine (6 g) and sodium bicarbonate (6.2 g) in 130 ml of 0.1M phosphate buffer (pH 6.4) was heated at 40° C. with stirring, 7-aminocephalosporanic acid (10 g) was added to this hot solution over a period of 30 minutes, and the suspension was heated to 60° C. with continued stirring. The pH of the resulting clear, brown solution was adjusted to 6.8-7.2, and heating was continued for an additional six hours. After allowing it to cool to room temperature, the brown solution was washed twice with 100 ml of ethyl acetate, the aqueous layer was separated, and its pH was adjusted to 2.0 with 1N hydrochloric acid. The formed crystals were collected by filtration, washed twice with 50 ml of water, and dissolved in 80 ml of acetonitrile by heating to 35° C. After adding 2 g of activated charcoal, the hot solution was allowed to stand for one hour, the charcoal was filtered off, and the filtrate was concentrated to about 20 ml at a temperature below 30° C. The formed colorless crystals were collected by filtration, giving 9.8 g of the objective compound.

IR (KBr, cm-1): 1795, 1520, 1410, 1350.

NMR (DMSO-$d_6$, $\delta$):
8.7 (1H, s), 7.4 (1H, s), 2.6 (3H, s).

(Step 2)

Preparation of (6R,7R)-7-[2-(2-chloroacetamido-4-thiazolyl)-2-(Z-methoxyimino)acetamido]-3-[(5-methyl-s-triazolo[1,5-a]pyrimidin-7-yl)thiomethyl]-8-oxo-5-thia-1-azabicyclo[4.2.0]oct-2-ene-2-carboxylic acid Using 2-(2-chloroacetamido-4-thiazolyl)-2-(Z-methoxyimino)acetic acid (6.6 g), triethylamine (4.2 ml,, phosphorus pentachloride (5.5 g), dichloromethane (40 ml), n-hexane (60 ml) and anhydrous tetrahydrofuran (50 ml), a 50ml solution of the corresponding acid chloride was prepared by a method similar to Step 1 of Example 7. This chloride solution was added dropwise to a solution of the product obtained in Step 1 (9 g) and bis(trimethylsilyl)acetamide (14 g) in 100 ml anhydrous dichloromethane at 0° C. with stirring over a period of 20 minutes, and the mixture was stirred at 0° C. for an additional 20 minutes and then at room temperature for two hours. After removing the solvent by distillation under reduced pressure, the brown residue was shaken with a mixture of ethyl acetate (200 ml) and water (80ml), the pH was adjusted to 7.5 with sodium bicarbonate, and the aqueous layer was then separated and washed with ethyl acetate. The pH of the aqueous layer was adjusted to 2.0 with 1N hydrochloric acid, the formed crystals were collected by filtration, and washed twice with 30 ml of water and then once with 20 ml of 50% aqueous acetone, affording 7.5 g of the objective compound as colorless crystals.

IR (KBr, cm-1): 1785, 1690, 1040.
NMR (DMSO-$d_6$,$\delta$):
9.6 (1H, d), 8.5 (1H, s), 8.0 (1H, s), 7.3 (1H, s), 6.7 (1H, s), 4.4 (2H, s), 3.8 (3H, s), 2.6 (3H, s).

(Step 3)

Preparation of (6R,7R)-7-[2-(2-amino-4-thiazolyl)-2-(Z-methoxyimino)acetamido]-3-[(5-methyl-s-triazolo[1,5-a]pyrimidin-7-yl)thiomethyl]-8-oxo-5-thia-1-azabicyclo[4.2.0.]oct-2-ene-2-carboxylic acid The product obtained in Step 2 (5 g) was dissolved in 150 ml dimethylacetamide, 11.9 g thiourea was added to this solution at room temperature with stirring over a period of 20 minutes, and the mixture was stirred at room temperature for three hours. After removing the solvent by distillation at a temperature below 20° C. under a pressure of 1 mmHg, the residue was added to a mixture of ethyl acetate (200 ml) and water (80 ml), and the pH was adjusted to 7.8 with sodium bicarbonate. The aqueous layer was washed with ethyl acetate until no thiourea could be detected. The pH was lowered to 2.0 with 1N hydrochloric acid, the formed crystals were collected by filtration, and washed twice with 20 ml of water, then once with 10 ml of 50% aqueous acetone, affording 3 g of the objective compound as colorless crystals.

IR (KBr, cm-1): 1775, 1630, 1520, 1040.
NMR (DMSO-$d_6$,$\delta$): 9.5 (1H, d, 7 Hz), 8.6 (1H, s), 7.3 (1H, s), 6.7 (1H, s), 3.8 (3H, s), 2.6 (3H, s).

EXAMPLE 9

Preparation of (6R,7R)-7-[2-(2-amino-4-thiazolyl)-2-(Z-methoxyimino)acetamido]-3-[(6-carboxy-s-triazolo[1,5-a]pyrimidin-7-yl)thiomethyl]-8-oxo-5-thia-1-azabicyclo[4.2.0]oct-2-ene-2-carboxylic acid (Compound 3)

A suspension of the product obtained in Example 2 (3 g) and sodium bicarbonate (4.5 g) in 160 ml of 0.1M phosphate buffer (pH 6.4) was heated to 40° C. with stirring, and the product obtained in Step 2 of Example 7 (8.8 g) was added to this hot suspension over a period of 20 minutes. The mixture was then heated to 60° C., and stirred at this temperature for six hours while maintaining the pH between 6.8 and 7.2. At the end of reaction, the resulting solution was allowed to cool to room temperature, was washed with 200 ml of ethyl acetate, and the pH of the aqueous layer was adjusted to 2.0 with 1N hydrochloric acid. The formed crystals were collected by filtration, and washed twice with 50 ml of water and then once with 30 ml of 50% aqueous acetone, giving 4.9 g of the objective compound as colorless crystals.

IR (KBr, cm-1): 1770, 1530, 1040.
NMR (DMSO-$d_6$,$\delta$):
9.5 (1H, d, 7 Hz), 9.0 (1H, s), 8.7 (1H, s), 6.8 (1H, s), 3.8 (3H, s).

EXAMPLE 10

Preparation of (6R,7R)-7-[2-(2-amino-4-thiazolyl)-2-(Z-methoxyimino)acetamido]-3-[(5-carboxymethyl-s-triazolo[1,5-a]pyrimidin-7-yl)thiomethyl]-8-oxo-5-thia-1-azabicyclo[4.2.0]oct-2-ene-2-carboxylic acid (Compound 5)

Starting from the product obtained in Example 4 (2.1 ) and the product obtained in Step 2 of Example 7 (4.6 g), 5 g of the objective compound was obtained as colorless crystals in a manner similar to Example 9.

IR (KBr, cm-1): 1770, 1520, 1360, 1040.
NMR (DMSO-$d_6$,$\delta$):
9.6 (1H, d, 7 Hz), 8.5 (1H, s), 7.2 (1H, s), 6.8 (1H, s), 3.8 (5H, s).

EXAMPLE 11

Preparation of (6R,7R)-7-[2-(2-amino-4-thiazolyl)-2-(Z-methoxyimino)acetamido]-3-[(2-carboxymethyl-5-methyl-s-triazolo[1,5-a]pyrimidin-7-yl)thiomethyl]-8-oxo-5-thia-1-azabicyclo[4.2.0]oct-2-ene-2-carboxylic acid (Compound 4)

Starting from the product obtained in Example 3 (2.2 g) and the product obtained in Step 2 of Example 7 (4.6 g), 5 g of the objective compound was obtained as colorless crystals in a manner similar to Example 9.

IR (KBr, cm-1): 1770, 1520, 1040.
NMR (DMSO-$d_6$,$\delta$):
9.6 (1H, d, 7 Hz), 7.2 (1H, s), 6.7 (1H, s), 3.8 (5H, s), 2.5 (3H, s).

EXAMPLE 12

Preparation of (6R,7R)-7-[2-(2-amino-4-thiazolyl)-2-(Z-methoxyimino)-acetamido]-3-[(5-carboxy-s-triazolo[1,5-a]pyrimidin-7-yl)thiomethyl]-8-oxo-5-thia-1-azabicyclo[4.2.0]oct-2-ene-2-carboxylic acid (Compound 6)

Starting from the product obtained in Example 5 (1.6 g) and the product obtained in Step 2 of Example 7 (4.4 g), 3.8 g of the objective compound was obtained as colorless crystals in a manner similar to Example 9.

IR (KBr, cm-1): 1770, 1540, 1360, 1190, 1040.
NMR (DMSO-$d_6$,$\delta$):
9.6 (1H, d, 8 Hz), 8.6 (1H, s), 7.6 (1H, s), 6.8 (1H, s), 3.9 (3H, s).

EXAMPLE 13

Preparation of (6R,7R)-7-[2-(2-amino-4-thiazolyl)-2-(-Z-methoxyimino)-acetamido]-3-[(2,6-dicarboxy-s-triazolo[1,5-a]pyrimidin-7-yl)thiomethyl]-8-oxo-5-thia- 1-azabicyclo[4.2.0]oct-2-ene-2-carboxylic acid (Compound 7)

Starting from the product obtained in Example 6 (1.2 g) and the product obtained in Step 2 of Example 7 (2.3 g), 2 g of the objective compound was obtained as colorless crystals in a manner similar to Example 9.

IR (KBr, cm-1):
1770, 1630, 1040.
NMR (DMSO-$d_6,\delta$):
9.6 (1H, d, 7 Hz), 9.1 (1H, s), 6.7(1H, s), 3.8 (3H, s).

EXAMPLE 14

Preparation of (6R,7R)-7-amino-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid To a suspension of 7-aminocephalosporanic acid (153 g) and the product obtained in Example 1 (118 g) in 850 ml acetonitrile, was added boron tifluoride etherate (240 g) at room temperature over a period of minutes, and the resultant suspension was heated at 45°–55° C. with stirring. The mixture turned into a dark yellow solution in about 20 minutes. After heating at that temperature for two hours, the reaction mixture was cooled on ice, 900 ml of water was added over a period of 10 minutes. The solution became gradually turbid, and crystals began to separate out. Collecting them by filtration, followed by washing thrice with 150 ml of water, then thrice with 200 ml of acetone, 190 g of the objective compound was obtained as colorless crystals.

IR (KBr, cm$^{-1}$):
1792, 1610, 1595, 1410, 1240, 1060, 770.
NMR (DMSO-$d_6,\delta$):
7.4 (1H, s), 5.0 (1H, d, 5 Hz), 4.9 (1H, d, 5 Hz), 4.4 (2H, bs), 3.7 (2H, ABq), 2.6 (3H, s).

EXAMPLE 15

Preparation of (6R,7R)-7-amino-3-[(2-diphenylmethyloxycarbonyl-5-methyl-s-triazolo[1,5-a]-pyrimidin-7-yl)thiomethyl]-8-oxo-5-thia-1-azabicyclo[4.2.0]oct-2-ene-2-carboxylic acid diphenylmethyl ester The product obtained in Example 14 (190 g) was suspended in a mixture of acetone (2 liters) and methanol (300 ml). To this suspension a purple solution of diphenyldiazomethane (220 g) in 500 ml of dichloromethane was added dropwise over a period of one hour. The reaction proceeded with effervescence and evolution of heat. After all the diphenyldiazomethane solution was added, the mixture was stirred at room temperature for 20 hours, the insoluble matters were filtered off, and the solvent was removed by distillation from the filtrate under reduced pressure, leaving 380 g of purplish red oil. Ether (800 ml) was added, and the formed crystals were collected by filtration and washed with ether, affording 225 g of the objective compound as colorless crystals.

IR (KBr, cm$^{-1}$):
1795, 1730, 1590, 1510, 1450, 1365, 1295, 1225, 1210, 1170, 1000, 915, 765, 700.
NMR (DMSO-$d_6,\delta$):
7.5–7.1 (22H, m), 6.9 (1H, s), 5.0 (1H, d, 5 Hz) 4.9 (1H, d, 5 Hz), 4.3 (2H, bs), 3.7 (2H, ABq) 2.6 (3H, s).

EXAMPLE 16

Preparation of (6R,7R)-7-[2-(2-triphenylmethylamino-4-thiazolyl)-2-(Z-1-methoxy-1-methylethyloxyimino)acetamido]-3-[(2-diphenylmethyloxycarbonyl-5-methyl-s-triazolo[1,5-a]pyrimidin-7-yl)thiomethyl]-8-oxo-5-thia-1-azabicyclo[4.2.0]oct-2-ene-2-carboxylic acid diphenylmethyl ester.

The product obtained in Example 15 (165 g) and 2-(2-triphenylmethylamino-4-thiazolyl)-2-(Z-(1-methoxy-1-methylethyloxyimino)acetic acid (220 g) were dissolved in anhydrous dichloromethane (2.5 liters) with stirring, the faint yellow solution was cooled to −15° C., and a solution of dicyclohexylcarbodiimide (90 g) in anhydrous dichloromethane (500 ml) was added dropwise over a period of 30 minutes. The mixture was stirred at 0° C. for three hours and then at room temperature for three hours. The insoluble matters were filtered off, and the reddish brown filtrate was concentrated under reduced pressure, leaving a reddish brown oil. Ethyl acetate (1 liter) was added, the insoluble matters were filtered off, and the filtrate was washed with 100 ml of 0.3N aqueous citric acid, 150 ml of saturated sodium bicarbonate solution and saturated sodium chloride solution in that order, and dried over anhydrous magnesium sulfate. The dried solution was concentrated in vacuo. The brown, viscous oil left (520 g) was purified by silica gel column chromatography using ethyl acetate/n-hexane as eluent, yielding 240 g of the objective compound as brown crystals.

IR (KBr, cm$^{-1}$):
1790, 1735, 1595, 1505, 1445, 1375, 1225, 1205, 1180, 1070, 1000, 950, 895, 750, 700.
NMR (DMSO-$d_6,\delta$):
9.5 (1H, d, 8 Hz), 8.8 (1H, s), 7.5–7.2 (37H, m), 7.0 (1H, s), 6.8 (1H, s), 5.9 (1H, dd, 8 Hz, 5 Hz), 5.3 (1H, d, 5 Hz), 4.4 (2H, bs), 3.7 (2H, ABq), 3.1 (3H, s), 2.6 (3H, s), 1.4 (6H, s).

EXAMPLE 17

Preparation of (6R,7R)-7-[2-(2-triphenylmethylamino-4-thiazolyl)-2-(Z-hydroxyimino)acetamido]3-[(2-diphenylmethyloxycarbonyl-5-methyl-s-triazolo[1,5-a]pyrimidin-7-yl)thiomethyl]-8-oxo-5-thia-1-azabicyclo[4.2.0]oct-2-ene-2-carboxylic acid diphenylmethyl ester.

To an ice-cooled solution of the product obtained in Example 16 (220 g) in 1.2 liters of acetone was added 250 ml of 1N hydrochloric acid over a period of ten minutes, the resulting red solution was stirred at room temperature for two hours, and then concentrated to 400–500 ml under reduced pressure at a bath temperature below 20° C. Ethyl acetate (800 ml) was added to the concentrate, and the solution was washed with 200 ml of saturated sodium chloride solution and dried over anhydrous sodium sulfate. The dried solution was concentrated in vacuo, and the red viscous product left (190 g) was treated with 500 ml ether, giving 175 g of the objective compound as yellow crystals.

IR (KBr, cm$^{-1}$):
3380, 2940, 1790, 1735, 1595, 1520, 1505, 1500, 1480, 1225, 1205, 1180, 1000, 900, 760, 740, 700.
NMR (DMSO-$d_6,\delta$):
11.3 (1H, s), 9.6 (1H, d, 8 Hz), 8.7 (1H, s), 7.5–7.1 (37H, m), 6.9 (1H, s), 6.6 (1H, s), 5.9 (1H, dd, 8 Hz, 5 Hz), 5.2 (1H, d, 5 Hz), 4.3 (2H, bs), 3.8 (2H, ABq), 2.6 (3H, s).

EXAMPLE 18

Preparation of (6R,7R)-7-[2-(2-amino-4-thiazolyl)-2-(Z-hydroxyimino)acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid (Compound 8)

The product obtained in Example 17 (2.4 g) was suspended under ice cooling in 4 ml anisole, and 40 ml of trifluoroacetic acid containing 2 ml of water was added dropwise to this suspension over a period of ten minutes, and the mixture was allowed to stand until room temperature was reached. After removing the solvent by distillation under reduced pressure, 300 ml ether was added to the residue, and the formed crystals were collected by filtration and washed with 50% aqueous acetone, affording 0.9 g of the objective compound as light brown crystals.

IR (KBr, cm$^{-1}$):
1772, 1650, 1600, 1550, 1510, 1410, 1255.

NMR (DMSO-$d_6$, $\delta$):
11.3 (1H, s), 9.5 (1H, d, 8 Hz), 7.4 (1H, s), 7.1 (2H, s), 6.7 (1H, s), 5.8 (1H, dd), 5.2 (1H, d), 4.4 (2H, bs), 3.7 (2H, ABq), 2.6 (3H, s).

EXAMPLE 19

Preparation of (6R,7R)-7-[2-(2-triphenylmethylamino-4-thiazolyl)-2-[Z-(2-furancarbonyl)oxyimino]acetamido]-3-[(2-diphenylmethyloxycarbonyl-5-methyl-s-triazolo[1,5-a]pyrimidin-7-yl)thiomethyl]-8-oxo-5-thia-1-azabicyclo[4.2.0]oct-2-ene-2-carboxylic acid diphenylmethyl ester To an ice-cooled solution of the product obtained in Example 17 (0.5 g) in dry dichloromethane (12 ml) was added potassium carbonate (0.072 g) all at once, followed by dropwise addition of a solution of 2-furoyl chloride (0.067 g) in dry dichloromethane (7 ml) over a period of five minutes. The mixture was stirred under ice cooling for 40 minutes and then at room temperature for an additional 40 minutes. After filtering off the insoluble matters, the filtrate was concentrated under reduced pressure, and the yellow residue was purified by silica gel column chromatography, giving 0.42 g of the objective compound as faint yellow crystals.

IR (KBr, cm$^{-1}$):
1790, 1740, 1690, 1595, 1510, 1470, 1450, 1380, 1290, 1205, 1085, 1060, 900, 760, 745, 700.

NMR (DMSO-$d_6$, $\delta$):
10.1 (1H, d, 8 Hz), 9.2 (1H, s), 8.0 (1H, d, 2 Hz), 7.6-7.2 (39H, m), 7.0 (1H, s), 6.7 (1H, dd, 4 Hz, 2 Hz), 6.0 (1H, dd, 8 Hz, 5 Hz), 5.3 (1H, d, 5 Hz), 4.4 (2H, bs), 3.8 (2H, ABq), 2.6 (3H, s).

EXAMPLE 20

Preparation of (6R,7R)-7-[2-(2-amino-4-thiazolyl)-2-[Z-(2-furancarbonyl)oxyimino]acetamido]-3-[(2-carboxy-5-methyl-s-triazolo[1,5-a]pyrimidin-7-yl)thiomethyl]-8-oxo-5-thia-1-azabicyclo-[4.2.0]oct-2-ene-2-carboxylic acid (Compound 9)

To an ice-cooled solution of the product obtained in Example 19 (0.4 g) in dichloroethane (2 ml) were added 0.5 ml of anisole and then 0.3 ml of trifluoroacetic acid. The mixture was stirred at room temperature for two hours, the solvent was removed by distillation under reduced pressure, and the residue was crystallized using 10 ml of ether, affording 0.18 g of the objective compound as faint yellow crystals.

IR (KBr, cm$^{-1}$):
1775, 1735, 1600, 1510, 1470, 1395, 1290, 1070, 775, 750.

NMR (DMSO-$d_6$, $\delta$):
10.0 (1H, d, 8 Hz), 8.1 (1H, d, 2 Hz), 7.4 (1H, s), 7.4-7.2 (3H, m), 7.1 (1H, s), 6.7 (1H, dd, 4 Hz, 2 Hz), 6.0 (1H, dd, 8 Hz, 5 Hz), 5.3 (1H, d, 5 Hz), 4.5 (2H, bs), 3.6 (2H, ABq, 18 Hz), 2.6 (3H, s).

EXAMPLE 21

Preparation of (6R,7R)-7-[2-(2-triphenylmethylamino-4-thiazolyl)-2-[Z-(2-thiophenecarbonyl)oxyimino]acetamido]-3-[(2-diphenylmethyloxycarbonyl-5-methyl-s-triazolo[1,5-a]pyrimidin-7-yl)thiomethyl]-8-oxo-5-thia-1-azabicyclo[4.2.0]oct-2-ene-2-carboxylic acid diphenylmethyl ester.

Potassium carbonate (219 mg) was suspended in a solution of the product obtained in Example 17 (1.5 g) in dry dichloromethane (36 ml), and the air in the system was replaced with nitrogen. After cooling on ice water, a solution of 2-thiophenecarbonyl chloride (234 mg) in dry dichloromethane (20 ml) was added dropwise, the mixture was allowed to stand until room temperature was reached, and dichloromethane (40 ml) was added after two hours. The mixture was washed with water and saturated sodium chloride solution. The organic layer was dried over anhydrous sodium sulfate, and the solvent was removed by distillation under reduced pressure. The residue was crystallized from ether, and the crystals were washed twice with ether, giving 1.4 g of the objective compound as faint yellow crystals.

IR (KBr, cm$^{-1}$):
1792, 1740, 1595, 1510, 1450, 1415, 1250, 1205, 1060, 1010, 740, 700.

NMR (DMSO-$d_6$, $\delta$):
10.0 (1H, d, 8 Hz), 9.1 (1H, s), 8.0 (2H, m), 7.5-7.0 (40H, m), 6.0 (1H, dd, 8 Hz, 5 Hz), 5.3 (1H, d, 5 Hz), 4.4 (2H, bs), 3.8 (2H, ABq), 2.5 (3H, s).

EXAMPLE 22

Preparation of (6R,7R)-7-[2-(2-amino-4-thiazolyl)-2-[Z-(2-thiophenecarbonyl)oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid (Compound 10)

The product obtained in Example 21 (1.0 g) was dissolved under ice cooling in anisole (2 ml), then trifluoroacetic acid (8.8 ml) containing 0.8 ml of water was added dropwise to this solution over a period of ten minutes, and the mixture was allowed to stand until room temperature was reached. After 1.5 hours, the solvent was removed by distillation under reduced pressure. Ether was added to the residue to form crystals. The crystals were collected by filtration and washed with dichloromethane, ethyl acetate and ether in that order, affording 590 mg of the objective compound as faint yellow crystals.

IR (KBr, cm$^{-1}$):
1775, 1734, 1600, 1515, 1415, 1250, 1205, 1065, 1015, 740.

NMR (DMSO-$d_6$, $\delta$):
10.0 (1H, d, 8 Hz), 8.3-7.9 (2H, dd), 7.4 (1H, s), 7.3 (1H, d), 7.1 (1H, s), 6.0 (1H, dd, 8 Hz, 5 Hz), 5.3 (1H, d, 5 Hz), 4.5 (2H, bs), 3.7 (2H, ABq), 2.6 (3H, s).

EXAMPLE 23

Preparation of (6R,7R)-7-[2-(2-triphenylmethylamino-4-thiazolyl)-2-[Z-(3-pyridinecarbonyl)oxyimino]acetamido]-3-[(2-diphenylmethyloxycarbonyl-5-methyl-s-triazolo[1,5-a]pyrimidin-7-yl)thiomethyl]-8-oxo-5-thia-1-azabicyclo[4.2.0]oct-2-ene-2-carboxylic acid diphenylmethyl ester Potassium carbonate (180 mg) was added to a solution of the product obtained in Example 17 (1.0 g) in dry dichloromethane (20 ml). After cooling on ice water, a solution of 3-pyridinecarbonyl chloride (180 mg) in 5 ml of dry dichloromethane was added dropwise, the mixture was stirred at room temperature for two hours, and then washed with water and saturated sodium chloride solution. The organic layer was dried over anhydrous sodium sulfate, the solvent was removed by distillation under reduced pressure, the residue was purified by silica gel column chromatography, giving 700 mg of the objective compound as faint yellow crystals.

IR (KBr, cm$^{-1}$):
1790, 1744, 1595, 1510, 1205, 760, 740, 700.

NMR (DMSO-d$_6$,$\delta$):
10.7 (1H, d,), 9.1 (2H, m), 8.8 (1H, dd), 8.3 (1H, dd), 7.7-6.8 (40H, m), 5.8 (1H, dd,), 5.2 (1H, d,), 4.3 (2H, bs), 3.6 (2H, ABq), 2.5 (3H, s).

EXAMPLE 24

Preparation of (6R,7R)-7-[2-(2-amino-4-thiazolyl)-2-[Z-(3-pyridinecarbonyl)oxyimino]acetamido]3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid (Compound 11)

The product obtained in Example 23 (500 mg) was dissolved in dichloroethane (2 ml), then anisole (0.7 ml) and trifluoroacetic acid (1.7 ml) were dropwise added to this solution under ice cooling, and the mixture was allowed to stand. After one hour, the reaction mixture was poured into ether, and the formed crystals were collected by filtration and washed with ether, affording 200 mg of the objective compound as faint yellow crystals.

IR (KBr, cm$^{-1}$): 1773, 1675, 1595, 1510, 1270.

NMR (DMSO-d$_6$, $\delta$):
10.1 (1H, d, 9 Hz), 9.1 (1H, d), 8.8 (1H, d), 8.3 (1H, d), 7.6 (1H, dd), 7.4 (1H, s), 7.1 (1H, s), 6.0 (1H, dd, 9 Hz, 5 Hz), 5.2 (1H, d, 5 Hz), 4.4 (2H, bs), 3.7 (2H, ABq, 18 Hz), 2.6 (3H, s).

EXAMPLE 25

Preparation of (6R,7R)-7-[2-(2-triphenylmethylamino-4-thiazolyl)-2-[Z-(3,4-methylenedioxybenzoyl)oxyimino]acetamido]-3-[(2-diphenylmethyloxycarbonyl-5-methyl-s-triazolo[1,5-a]pyrimidin-7-yl)thiomethyl]-8-oxo-5-thia-1-azabicyclo[4.2.0]oct-2-ene-2-carboxylic acid diphenylmethyl ester.

Potassium carbonate was added to a solution of the product obtained in Example 17 (2 g) in 30 ml dichloromethane. After cooling with ice water, a solution of 3,4-methylenedioxybenzoyl chloride (520 mg) in 10 ml of dichloromethane was added dropwise over a period of ten minutes. The mixture was stirred under ice cooling for 45 minutes, then at room temperature for one hour, and mixed with 40 ml of dichloromethane. The mixture was washed with 10 ml of water and 20 ml of saturated sodium chloride solution. The organic layer was dried over anhydrous sodium sulfate, and the solvent was removed by distillation under reduced pressure. The residue (2.3 g) was purified by silica gel column chromatography using ethyl acetate/n-hexane as eluent, giving 2.1 g of the objective compound as faint yellow crystals.

IR (KBr, cm$^{-1}$):
1791, 1745, 1600, 1505, 1440, 1260, 1030, 750, 700.

NMR (DMSO-d$_6$, $\delta$):
9.9 (1H, d, 8 Hz), 9.1 (1H, s), 7.5-7.0 (42H, m), 6.1 (2H, s,), 5.9 (1H, dd, 8 Hz, 5 Hz), 5.2 (1H, d, 5 Hz), 4.4 (2H, bs), 3.8 (2H, bs), 2.5 (3H, s).

EXAMPLE 26

Preparation of (6R,7R)-7-[2-(2-amino-4-thiazolyl)-2-[Z-(3,4-methylenedioxybenzoyl)oxyimino)]-acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid (Compound 12)

The product obtained in Example 25 (2.1 g) was dissolved in dichloroethane (2 ml), then 12 ml of anisole and 2.4 ml of trifluoroacetic acid were dropwise added to this solution under ice cooling, and the reddish yellow solution was stirred for two hours under ice cooling. The trifluoroacetic acid was removed under reduced pressure, and the residue was subjected to azeotropic distillation with 5 ml of anhydrous benzene to give a dark red oil (18 ml). The oil was then treated with 30 ml of ether, and faint yellow crystals (1 g) were obtained. The crystals were purified by silica gel column chromatography using ether containing 1% methanol as eluent, affording 0.7 g of the objective compound as colorless crystals.

IR (KBr, cm$^{-1}$):
3400, 1774, 1739, 1580, 1500, 1250, 1030, 730.

NMR (DMSO-d$_6$, $\delta$):
10.1 (1H, d, 8 Hz), 7.6 (1H, d, 9 Hz), 7.4 (1H, s), 7.2 (1H, m), 7.1 (1H, s), 7.0 (1H, d, 9 Hz), 6.1 (2H, s), 6.0 (1H, dd, 8 Hz, 5 Hz), 5.2 (1H, d, 5 Hz), 4.5 (2H, bs), 3.8 (2H, bs), 2.6 (3H, s).

EXAMPLE 27

Preparation of 2-(2-triphenylmethylamino-4-thiazolyl)-2-[Z-(3,4-methylenedioxybenzoyl)oxyimino]acetic acid Triethylamine (6.7 ml) was added with stirring to an ice-cooled suspension of 10 g of 2-(2-triphenylmethylamino-4-thiazolyl)-2-(Z-hydroxyimino)acetic acid in 140 ml of anhydrous dichloromethane. The suspension turned to a clear, faint yellow solution after ten minutes. A solution of 3,4-methylenedioxybenzoyl chloride (3.4 g) in 25 ml of dichloromethane was dropwise added and the mixture was stirred at room temperature for one hour. The insoluble crystals were removed by filtration and the filtrate was washed twice with 20 ml of 1N hydrochloric acid and 30 ml of saturated sodium chloride solution each, and dried over anhydrous sodium sulfate. The dried filtrate was concentrated under reduced pressure, and the viscous brown residue (14.2 g) was purified by silica gel column chromatography using chloroform/methanol (20-10:1) as eluent, affording 2.3 g of the objective compound as light brown crystals.

NMR (DMSO-d$_6$, $\delta$):
9.0 (1H, s), 7.7-7.2 (19H, m), 6.2 (2H, s).

EXAMPLE 28

Preparation of (6R,7R)-7-[2-(2-triphenylmethylamino-4-thiazolyl)-2-[Z-(3,4-methylenedioxybenzoyl)oxyimino]acetamido]-3-[(2-diphenylmethyloxycarbonyl-5-methyl-s-triazolo[1,5-a]pyrimidin-7-yl)thiomethyl]-8-oxo-5-thia-1-azabicyclo[4.2.0]oct-2-ene-2-carboxylic acid diphenylmethyl ester.

(Step 1)

Preparation of 2-[(2-triphenylmethylamino)-4-thiazolyl]-2-[Z-(3,4-methylenedioxybenzoyl)oxyimino]acetic acid chloride To an ice-cooled solution of the product obtained in Example 27 (2.3 g) in 30 ml of anhydrous tetrahydrofuran was added with stirring 0.55 ml of triethylamine, followed by addition of 0.83 g of phosphorus pentachloride ten minutes later. The mixture was stirred at room temperature for one hour and the solvent was removed from the resulting brown solution by distillation under reduced pressure. The residue was washed twice with 30 ml of n-hexane. The washed solid was dissolved in 30 ml of anhydrous tetrahydrofuran, and the insoluble matters were filtered off. The brown solution thus obtained was submitted to the next step without further purification.

(Step 2)

Preparation of (6R,7R)-7-[2-(2-triphenylmethylamino-4-thiazolyl)-2-[Z-(3,4-methylenedioxybenzoyl)oxyimino]acetamido]-3-[(2-diphenylmethyloxycarbonyl-5-methyl-s-triazolo[1,5-a]pyrimidin-7-yl)thiomethyl]-8-oxo-5-thia-1-azabicyclo[4.2.0]oct-2-ene-2-carboxylic acid diphenylmethyl ester.

Triethylamine (0.55 ml) was added to an ice-cooled suspension of the product obtained in Example 15 (3 g) in 20 ml of anhydrous tetrahydrofuran with stirring, giving a clear, light brown solution. To this solution was dropwise added the tetrahydrofuran solution of the product obtained in Step 1, the pH was adjusted to 7.5 to 8.0 with dicyclohexylamine, and the mixture was stirred at room temperature for three hours. After filtering off the insoluble matters, the filtrate was concentrated under reduced pressure, and the spongy residue was purified by silica gel column chromatography using chloroform as eluent, affording 0.5 g of the objective compound as brown crystals.

IR (KBr, cm$^{-1}$):
1791, 1745, 1600, 1505, 1440, 1260, 1030, 750, 700.
NMR (DMSO-d$_6$, δ):
9.9 (1H, d, 8 Hz), 9.1 (1H, s), 7.5–7.0 (42H, m), 6.1 (2H, s), 5.9 (1H, dd, 8 Hz, 5 Hz), 5.2 (1H, d, 5 Hz), 4.4–4.3 (2H, bs), 3.8 (2H, s), 2.5 (3H, s). The result is in good agreement with that of Example 25.

EXAMPLE 29

Preparation of 2-(2-triphenylmethylamino-4-thiazolyl)-2-[Z-(2-furancarbonyl)oxyimino]acetic acid Triethylamine (8.7 ml) was added to an ice-cooled suspension of 2-(2-triphenylmethylamino-4-thiazolyl)-2-(Z-hydroxyimino)acetic 2-(Z-hydroxyimino)acetic acid (13 g) in 250 ml of anhydrous dichloromethane with stirring. The suspension turned to a clear, faint yellow solution. A solution of 2-furoyl chloride (3.3 g) in 20 ml of anhydrous dichloromethane was dropwise added under ice cooling, the resulting light brown solution was stirred at room temperature for one hour, the mixture was poured into 130 ml of ice-cooled 0.5N hydrochloric acid, and the formed crystals were collected by filtration and washed thrice with 30 ml dichloromethane, affording 5.2 g of the objective compound as colorless crystals.

IR (KBr, cm$^{-1}$): 3400, 3000, 1752, 1595, 1576, 1533, 1287, 1065, 701.
NMR (DMSO-d$_6$, δ): 9.1 (1H, s), 7.7 (1H, d), 7.3 (15H, s), 7.0 (1H, d), 6.9 (1H, s), 6.5 (1H, dd).

EXAMPLE 30

Preparation of (6R,7R)-7-[2-(2-triphenylmethylamino-4-thiazolyl)-2-[Z-(2-furancarbonyl)oxyimino]acetamido]-3-[(2-diphenylmethyloxycarbonyl-5-methyl-s-triazolo[1,5-a]pyrimidin-7-yl)thiomethyl]-8-oxo-5-thia-1-azabicyclo[4.2.0]oct-2 ene-2-carboxylic acid diphenylmethyl ester.

The product obtained in Example 29 (3.1 g) and the product obtained in Example 15 (4.3 g) were dissolved in anhydrous dichloromethane (200 ml) with stirring, the faint yellow solution was cooled to −30° C., and a solution of dicyclohexylcarbodiimide (1.2 g) in anhydrous dichloromethane (30 ml) was dropwise added over a period of five minutes. The resulting faint yellow solution was allowed to stand at 0° C. for nine hours, the colorless crystals separated were removed by filtration, and the filtrate was washed with 50 ml of 1N aqueous citric acid, 50 ml of saturated sodium bicarbonate solution and 80 ml of saturated sodium chloride solution in that order and dried over anhydrous sodium sulfate. The dried filtrate was concentrated in vacuo, the yellow, viscous residue (6.8 g) was purified by silica gel column chromatography using ethyl acetate/n-hexane as eluent, yielding 5.3 g of the objective compound as faint yellow crystals.

IR (KBr, cm$^{-1}$): 3380, 3050, 3020, 1790, 1740, 1690, 1595, 1510, 1470, 1450, 1380, 1290, 1205, 1085, 1060, 900, 760, 745, 700.
NMR (DMSO-d$_6$, δ): 10.1 (1H, d, 8 Hz), 9.2 (1H, s), 8.0 (1H, d,
2 Hz), 7.6–7.2 (39H, m), 7.0 (1H, s), 6.7 (1H, dd, 2 Hz, 4 Hz), 6.0 (1H, dd, 5 Hz, 8 Hz), 5.3 (1H, d, 5 Hz), 4.4 (2H, bs), 3.8 (2H, ABq ), 2.6 (3H, s).

These analytical results are in good agreement with those of Example 19.

EXAMPLE 31

Preparation of (6R,7R)-7-[2-(2-triphenylmethylamino-4-thiazolyl)-2-(Z-cyanomethylthioacetyloxyimino)acetamido]-3-[(2-diphenylmethyloxycarbonyl-5-methyl-s-triazolo[1,5-a]pyrimidin-7-yl)thiomethyl]-8-oxo-5-thia-1-azabicyclo[4.2.0]oct-2-ene-2-carboxylic acid diphenylmethyl ester.

To an ice-cooled solution of the product obtained in Example 17 (500 mg) in 15 ml of anhydrous dichloromethane was dropwise added a solution of cyanomethylthioacetyl chloride (77 mg) in 5 ml dichloromethane, and the mixture was stirred under ice cooling for 20 minutes. After dilution with dichloromethane, the reaction mixture was washed with water and saturated sodium chloride solution, the organic layer was dried over anhydrous sodium sulfate, the solvent was removed by distillation under reduced pressure, and the residue was treated with ether, affording 510 mg of the objective compound as light brown crystals.

IR (KBr, cm$^{-1}$):
1785, 1740, 1689, 1595, 1508, 1200, 700.
NMR (DMSO-d$_6$, δ): 9.9 (1H, d, 8 Hz), 9.0 (1H, s), 7.5–7.1 (38H, m), 7.0 (1H, s), 5.8 (1H, dd, 8 Hz, 5 Hz), 5.3 (1H, d, 5 Hz), 4.3 (2H, s), 3.8 (2H, s), 3.7 (2H, s), 3.4 (2H, ABq), 2.6 (3H, s).

EXAMPLE 32

Preparation of (6R,7R)-7-[2-(2-amino-4-thiazolyl)-2--(Z-cyanomethylthioacetyloxyimino)acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid.

The product obtained in Example 31 (500 mg) was dissolved in dichloroethane, 0.4 ml of anisole, then 0.9 ml of trifluoroacetic acid was added dropwise to this solution under ice cooling, and the reaction mixture was stirred at room temperature for 90 minutes. After concentration under reduced pressure, ether was added to the residue, and the formed crystals were collected by filtration and washed with ether/chloroform, affording 300 mg of the objective compound as yellow crystals.

IR (KBr, cm$^{-1}$): 2245, 1774, 1680, 1595, 1510, 1405, 1245, 1200.

NMR (DMSO-d$_6$, δ): 10.0 (1H, d), 7.4 (1H, s), 6.7 (1H, s), 5.8 (1H, dd), 5.2 (1H, d), 4.4 (2H, bs), 3.7 - 3.4 (6H, m), 2.6 (3H, s).

EXAMPLE 33

Preparation of (6R,7R)-7-[2-(2-triphenylmethyl amino-4-thiazolyl)-2-[Z-(thiophene-2-acetyl)oxyimino]acetamido]-3-[(2-diphenylmethyloxycarbonyl5-methyl-s-triazolo[1,5-a]pyrimidin-7-yl)thiomethyl]-8-oxo-5-thia-1-azabicyclo[4.2.0]oct-2-ene-2-carboxylic acid diphenylmethyl ester.

Starting from the product obtained in Example 17 (1.0 g) and thiophene-2-acetic acid chloride (138 mg), and using potassium carbonate (146 mg) and dichloromethane (30 ml), 0.87 g of the objective compound was obtained as faint yellow crystals in a manner similar to Example 21.

IR (KBr, cm$^{-1}$): 1790, 1735, 1690, 1475, 1290, 1195, 900, 760, 745,700.

NMR (DMSO-d$_6$, δ): 9.9 (1H, d, 8 Hz), 9.1 (1H, s), 6.9–7.5 (42H, m), 6.0 (1H, dd, 8 Hz, 5 Hz), 5.2 (1H, d, 5 Hz), 4.4 (2H, bs), 4.1 (2H, s), 3.8 (2H, ABq), 2.7 (3H, s).

EXAMPLE 34

Preparation of (6R,7R)-7-[2-(2-amino-4-thiazolyl)-2-[Z-(thiophene-2-acetyl)oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid.

Starting from the product obtained in Example 33 (0.8 g) and using anisole (1.6 ml) and trifluoroacetic acid (8 ml), 0.4 g of the objective compound was obtained as faint yellow crystals in a manner similar to Example 22.

IR (KBr, cm$^{-1}$): 1790, 1720, 1590, 1510, 1450, 1385, 1300, 1060, 760, 745, 700.

NMR (DMSO-d$_6$, δ): 9.9 (1H, d, 8 Hz), 7.5–6.9 (7H, m), 5.9 (1H, dd, 5 Hz, 8 Hz), 5.2 (1H, d, 5 Hz), 4.5 (2H, bs), 4.1 (2H, s), 3.8 (2H, ABq), 2.7 (3H, s).

EXAMPLE 35

Preparation of (6R,7R)-7-[2-(2-triphenylmethylamino-4-thiazolyl)-2-[Z-(furan-2-propenoyl)oxyimino)acetamido]acetamido]-3-[(2-diphenylmethyloxycarbonyl5-methyl-s-triazolo[1,5-a]pyrimidin-7-yl)thiomethyl]-8-oxo-5-thia-1-azabicyclo[4.2.0]oct-2-ene-2-carboxylic acid diphenylmethyl ester Starting from the product obtained in Example 17 (1.0 g) and furan-2-propenoyl chloride (130 mg) and using potassium carbonate (146 mg) and dichloromethane (30 ml), 0.8 g of the objective compound was obtained as brown crystals in a manner similar to Example 21.

IR (KBr, cm$^{-1}$): 790, 1730, 1510, 1295, 900, 760, 745, 700.

NMR (DMSO-d$_6$, δ): 10.0 (1H, d, 8 Hz), 9.3 (1H, s), 7.9 (1H,d, 2 Hz), 7.6–7.2 (39H, m), 7.1 (1H, s), 7.0 (1H, d, 4 Hz), 6.7 (1H, dd, 4 Hz, 2 Hz), 6.4 (1H, d, 16 Hz), 6.0 (1H, dd, 8 Hz, 5 Hz), 5.3 (1H, d, 5 Hz), 4.4 (2H, bs), 3.8 (2H, ABq), 2.6 (3H, s).

EXAMPLE 36

Preparation of (6R,7R)-7-[2-(2-amino-4-thiazolyl)-2-[Z-(furan-2-propenoyl)oxyimino]acetamido]-3-[(2-carboxy-5-methyl-s-triazolo[1,5-a]pyrimidin- 7-yl)thiomethyl]-8-oxo-5-thia-1-azabicyclo[4.2.0]oct-2-ene-2-carboxylic acid.

Starting from the product obtained in Example 35 (700 mg) and using anisole (1. ml) and trifluoroacetic acid (7 ml), 0.4 g of the objective compound was obtained as light brown crystals in a manner similar to Example 22.

IR (KBr, cm$^{-1}$): 1775, 1720, 1600, 1390, 1290, 1070, 775, 750.

NMR (DMSO-d$_6$, δ): 9.9 (1H, d, 8 Hz), 7.9 (1H, d, 2 Hz), 7.6 (1H, d, 16 Hz), 7.4 (1H, s), 7.3 (2H, bs), 7.1 (1H, s), 7.0 (1H, d, 4 Hz), 6.7 (1H, dd, 4 Hz, 2 Hz), 6.4 (1H, d,16 Hz), 5.9 (1H, dd, 8 Hz, 5 Hz), 5.2 (1H, d, 5 Hz), 4.5 (2H, bs), 3.6 (2H, ABq), 2.7 (3H, s).

EXAMPLE 37

Preparation of (6R,7R)-7-[2-(2-amino-4-thiazolyl)-2-(Z-methoxyimino)acetamido]-3-[(2-carboxy-5-isopropyl-s-triazolo[1,5-a]pyrimidin-7-yl)thiomethyl]-8-oxo-5-thia-1-azabicyclo[4.2.0]oct-2-ene-2-carboxlic acid

(Step 1)

Preparation of 7-hydroxy-5-isopropyl-2-methoxycarbonyl-s-triazolo[1,5-a]pyrimidine A mixture of 3-amino-5-methoxycarbonyl-s-triazole (60 g) and ethyl 3-oxo-4-methylvalerate (65 g) in 600 ml of acetic acid was refluxed for five hours, the reaction mixture was cooled to room temperature, its pH was lowered to 1 to 2 with concentrated hydrochloric acid, and the separated crystals were recrystallized from ethanol, affording 54 g of the objective compound as colorless crystals.

M.P.: 198.2°–200.7° C.

(Step 2)

Preparation of 7-choro-5-isopropyl-2-methoxycarbonyl-s-triazolo[1,5-a]pyrimidine To a suspension of the product obtained in Step 1 (50 g) in 700 ml of phosphorus oxychloride 31 g of N,N-dimethylaniline was dropwise added at room temperature over a period of 20 minutes. The mixture was refluxed for one hour, excess phosphorus oxychloride was removed by distillation under normal pressure, and the reddish brown residue was dissolved in 2 liters of chloroform. This solution was slowly poured into 1.5 liters of ice-cooled saturated sodium bicarbonate solution, the chloroform layer was collected after shaking, and the aqueous layer was again extracted with fresh chloroform. The organic layers were joined together, washed with 800 ml of saturated sodium chloride solution and dried over anhydrous magnesium sulfate. The dried solution was concentrated under reduced pressure to about 100 ml, and 200 ml n-hexane was added to this concentrate, giving 47 g of the objective compound as colorless crystals.

(Step 3)

Preparation of 5-isopropyl-7-mercapto-2-methoxycarbonyl-s-triazolo[1,5-a]pyrimidine The product obtained in Step 2 (40 g) was added at 0° C. to a solution of sodium hydrosulfide (40 g) in one liter of water with stirring under a nitrogen stream. The mixture was stirred at 0° C. for one hour, then at room temperature for three hours, and the resulting yellow solution was washed with 200 ml of ethyl acetate. The aqueous layer was acidified with concentrated hydrochloric acid to pH 2.0, and the formed crystals were collected by filtration and washed with 100 ml of ethanol, affording 36 g of the objective compound as faint yellow crystals.

M.P.: 179.5°–181.4° C.

(Step 4)

Preparation of (6R,7R)-7-[2-(2-amino-4-thiazolyl)- 2-(Z-methoxyimino)acetamido]-3-[(2-carboxy-5-isopropyl-s-triazolo[1,5-a]pyrimidin-7-yl)thiomethyl]-8-oxo-5-thia-1-azabicyclo[4.2.0]oct-2-ene-2-carboxylic acid.

Sodium bicarbonate (6.9 g) and the product obtained in Step 3 (10 g) were dissolved in 290 ml of 0.1M phosphate buffer (pH 6.4) at room temperature. To this solution 19 g of the product obtained in Step 2 of Example 7 was added to 40° C. over a period of 20 minutes. The mixture was then stirred at 60° C. for six hours while maintaining the pH between 6.8 and 7.2. After cooling to room temperature, the reaction mixture was washed with 80 ml of ethyl acetate, the aqueous layer was acidified with 1N hydrochloric acid to pH 2.0, and the formed crystals were collected by filtration and washed with 30 ml of 50% aqueous acetone, affording 14 g of the objective compound as faint yellow crystals.

IR (KBr, cm$^{-1}$): 1765, 1040.

NMR (DMSO-d$_6$, δ): 9.6 (1H, d, 8 Hz), 7.6 (1H, s), 7.2 (2H, bs), 6.6 (1H, s), 5.7 (1H, dd, 8 Hz, 5 Hz), 5.1 (1H, d, 5 Hz), 4.5 (2H, bs), 3.8 (3H, s), 3.6 (3H, m), 1.3 (6H, d, 7 Hz).

EXAMPLE 38

Preparation of (6R,7R)-7-[2-(2-amino-4-thiazolyl)-2-(Z-methoxyimino)acetamido]-3-[(2-carboxy-s-tiazolo[1,5-a]pyrimidin-7-yl)thiomethyl]-8-oxo-5-thia-1-azabicyclo[4.2.0]oct-2-ene-2-carboxylicacid (Compound 14)

(Step 1)

Preparation of 7-hydroxy-2-methoxycarbonyl-s-triazolo[1,5-a]pyrimidine

A mixture of 2-amino-5-methoxycarbonyl-s-triazole (50 g) and ethyl β-ethoxyacrylate (75 g) in 500 ml of acetic acid was refluxed for three hours, the reaction mixture was cooled to room temperature, and the formed crystals were collected by filtration and washed with 80 ml of ether, affording 36.5 g of the objective compound as colorless crystals.

(Step 2)

Preparation of 7-chloro-2-methoxycarbonyl-s-triazolo[1,5-a]pyrimidine

To a suspension of the product obtained in Step 1 (35 g) in 400 ml phosphorus oxychloride 24 g of N,N-dimethylaniline was dropwise added at room temperature. The mixture was refluxed for two hours, excess phosphorus oxychloride was removed by distillation under normal pressure, and the reddish brown oil left was dissolved in 1.5 liters of chloroform. This solution was slowly poured into 800 ml of ice-cooled saturated sodium bicarbonate solution, the chloroform layer was collected after thorough mixing, and the aqueous layer was again extracted with one liter of fresh chloroform. The organic layers were joined together, washed with 500 ml of saturated sodium chloride solution, and dried over anhydrous magnesium sulfate. The dried solution was concentrated under reduced pressure to about 100 ml, and 200 ml of n-hexane was added to this concentrate, giving 20 g of the objective compound as faint yellow crystals.

(Step 3)

Preparation of 7-mercapto-2-methoxycarbonyl-s-triazolo[1,5-a]pyrimidine

The product obtained in Step 2 was added all at once at 0° C. to a solution of sodium hydrosulfide (20 g) in 450 ml of water with stirring under a nitrogen stream. The mixture was stirred at 0° C. for one hour, then for two hours at room temperature, and the resulting yellow solution was washed with 100 ml of ethyl acetate. The aqueous layer was acidified with concentrated hydrochloric acid to pH 2.0, and the formed crystals were collected by filtration and washed with 200 ml of ethanol, affording 18 g of the objective compound as faint yellow crystals.

M.P.: 205.8°–206.4° C.

(Step 4)

Preparation of (6R,7R)-7-[2-(2-amino-4-thiazolyl)-2--(Z-methoxyimino)acetamido]-3-[(2-carboxy-s-triazolo[1,5-a]pyrimidin-7-yl)thiomethyl]-8-oxo-5-thia-1-azabicyclo[4.2.0]oct-2-ene-2-carboxylic acid Sodium bicarbonate (7 g) and the product obtained in Step 3 (8.8 g) were dissolved in 300 ml of 0.1M phosphate buffer (pH 6.4) at room temperature. To this solution was added the product obtained in Step 2 of Example 7 (20 g). The reaction mixture was worked up in the same manner as Step 4 of Example 37, affording 14 g of the objective compound as colorless crystals.

IR (KBr, cm$^{-1}$): 1770, 1045.

NMR (DMSO-d$_6$, δ): 9.6 (1H, d, 8 Hz), 8.8 (1H, d), 7.5 (1H, d), 7.3 (2H, bs), 6.7 (1H, s), 5.8 (1H, dd, 8 Hz, 5 Hz), 5.2 (1H, d, 5 Hz), 4.4 (2H, bs), 3.8 (3H, s), 3.6 (2H, bs).

EXAMPLE 39

Preparation of (6R,7R)-7-[2-(2-amino-4-thiazolyl)-2-(Z-methoxyimino)acetamido]-3-[(2-carboxy5,6-dimethyl-s-triazolo[1,5-a]pyrimidin-7-yl)thiomethyl]-8-oxo-5-thia-1-azabicyclo[4.2.0]oct-2-ene-2-carboxylic acid (Step 1)

Preparation of 5,6-dimethyl-7-hydroxy-2-methoxycarbonyl-s-triazolo[1,5-a]pyrimidine A mixture of 3-amino-5-methoxycarbonyl-s-triazole (60 g) and ethyl 2-methyl-3-oxo-butylate (93 g) in 300 ml of acetic acid was refluxed for three hours. The original suspension became clear after heating one hour, and colorless crystals began to form upon further heating. After cooling to room temperature, the crystals were collected by filtration and washed with 300 ml of methanol, affording 55 g of the objective compound as colorless crystals.

M.P.: 231°–232.5° C.

(Step 2)

Preparation of 7-chloro-5,6-dimethyl-2-methoxycarbonyl-s-triazolo[1,5-a]pyrimidine To a suspension of the product obtained in Step 1 (50 g) in 500 ml of phosphorus oxychloride N,N-dimethylaniline (30 g) was dropwise added at room temperature, the mixture was refluxed for two hours, excess phosphorus oxychloride was removed by distillation under normal pressure, and the black oil left was dissolved in 200 ml of chloroform. This solution was slowly poured into 200 ml of ice-cooled saturated sodium bicarbonate solution, the chloroform layer was collected after thorough mixing, and the aqueous layer was again extracted with 200 ml of fresh chloroform. The combined organic layers were washed with 100 ml of saturated sodium chloride solution and dried over anhydrous sodium sulfate. The dried solution was concentrated under reduced pressure to about 50 ml, and 100 ml of n-hexane was added to this concentrate, giving 49 g of the objective compound as colorless crystals.

M.P.: 190.5°–192.3° C.

(Step 3)

Preparation of 5,6-dimethyl-7-mercapto-2-methoxycarbonyl-s-triazolo[1,5-a]pyrimidine The product obtained in Step 2 was added all at once at 0° C. to a solution of sodium hydrosulfide (40 g) in 800 ml of water with stirring under a nitrogen stream, the mixture was stirred at 0° C. for 30 minutes and then at room temperature for 1.5 hours, its pH was lowered to 2.0 with concentrated hydrochloric acid. The formed crystals were collected by filtration and washed with 300 ml of water and 200 ml of ethanol, affording 36 g of the objective compound as yellow crystals.

M.P.: 205.8°–207.1° C.

(Step 4)

Preparation of (6R,7R)-7-[2-(2-amino-4-thiazolyl)-2-(Z-methoxyimino)acetamido]-3-[(2-carboxy-5,6-dimethyl-s-triazolo[1,5-a]pyrimidin-7-yl)thiomethyl]-8-oxo-5-thia-1-azabicyclo[4.2.0]oct-2-ene-2-carboxylic acid Sodium bicarbonate (7 g) and the product obtained in Step 3 (10 g) were dissolved in 300 ml of 0.1M phosphate buffer (pH 6.4) at room temperature. To this solution the product obtained in Step 2 of Example 7 (20 g) was added at 40° C. over a period of 30 minutes. The mixture was stirred at 60° C. for six hours while maintaining the pH between 6.8 and 7.2. After cooling to room temperature, the reaction mixture was washed with 100 ml of ethyl acetate, the aqueous layer was acidified with 1N hydrochloric acid to pH 2.0, and the formed crystals were collected by filtration and washed with 50 ml of 50% aqueous acetone, affording 15 g of the objective compound as colorless crystals.

IR (KBr, cm$^{-1}$): 1770, 1640, 1530, 1040.

NMR (DMSO-d$_6$, δ): 9.6 (1H, d, 8 Hz), 6.7 (1H, s), 3.8 (3H, s), 2.6 (3H, s), 2.5 (3H, s).

EXAMPLE 40

Preparation of (6R,7R)-7-[2-(2-amino-4-thiazolyl)-2-(Z-methoxyimino)acetamido]-3-[(5-carboxy-2-methyl-s-triazolo[1,5-a]pyrimidin-7-yl)thiomethyl]-8-oxo-5-thia-1-azabicyclo[4.2.0]oct-2ene-2-carboxylic acid (Step 1)

Preparation of 5-ethoxycarbonyl-7-hydroxy-3-methyl-s-triazolo[1,5-a]pyrimidine

A mixture of 3-amino-5-methyl-s-triazole (30 g) and diethyl acetylenecarboxylate (54 g) in 250 ml ethanol was refluxed for three hours. After cooling to room temperature, the formed crystals were collected by filtration and washed with methanol, affording 45 g of the objective compound as faint yellow crystals.

M.P.: 254.6°–256.0° C.

(Step 2)

Preparation of 7-chloro-5-ethoxycarbonyl-2-methyl-s-triazolo[1,5-a]pyrimidine

To a suspension of the product obtained in Step 1 (23 g) in 300 ml of phosphorus oxychloride N,N-dimethylaniline (19 ml) was dropwise added at room temperature. The mixture was stirred at 80° C. for one hour, excess phosphorus oxychloride was removed by distillation under normal pressure, and the reddish brown oil left was shaken with 500 ml of chloroform and 200 ml of water. The pH was adjusted to 7 to 8 with saturated sodium bicarbonate solution, and the chloroform layer was collected. The aqueous layer was again extracted with 300 ml of fresh chloroform. The organic layers were joined together, dried and concentrated under reduced pressure to about 50 ml, then 100 ml of n-hexane was added to this concentrate, giving 18 g of the objective compound as faint yellow crystals.

M.P.: 133.7°–135.6° C.

(Step 3)

Preparation of 5-ethoxycarbonyl-7-mercapto-2-methyl-s-triazolo[1,5-a]pyrimidine

The product obtained in Step 2 (15 g) was added all at once at room temperature to a solution of sodium hydrosulfide (15 g) in 300 ml of water with stirring under a nitrogen stream, and the reaction mixture was worked up in the same manner as Step 3 of Example 37, affording 11 g of the objective compound as yellow crystals.

M.P.: 233.7°–235.8° C.

(Step 4) ps Preparation of (6R,7R)-7-[2-(2-amino-4-thiazolyl)-2-(Z-methoxyimino)acetamido]-3-[(5-carboxy-2-methyl-s-triazolo[1,5-a]pyrimidin-7-yl)thiomethyl]-8-oxo-5-thia-1-azabicyclo[4.2.0]oct-2-ene-2-carboxylic acid Sodium bicarbonate (6.0 g) and the product obtained in Step 3 (8 g) were dissolved in 250 ml of 0.1M phosphate buffer (pH 6.4) at room temperature. To this solution the product obtained in Step 2 of Example 7 (15 g) was added at 40° C. The reaction mixture was worked up in the manner similar to Step 4 of Example 37, affording 10.5 g of the objective compound as colorless crystals.

IR (KBr, cm$^{-1}$): 1770, 1540, 1360, 1190, 1040.

NMR (DMSO-d$_6$, δ): 9.6 (1H, d, 8 Hz), 8.6 (1H, s), 7.6 (1H, s), 6.8 (1H, s), 3.9 (3H, s).

EXAMPLE 41

Preparation of (6R,7R)-7-[2-(2-amino-4-thiazolyl)-2-(Z-methoxyimino)acetamido]-3-[(2-hydrazinocarbonyl-5-methyl-s-triazolo[1,5-a]pyrimidin-7-yl)thiomethyl]-8-oxo-5-thia-1-azabicyclo[4.2.0]oct-2-ene-2-carboxylic acid (Step 1)

Preparation of 2-hydrazinocarbonyl-7-mercapto-5-methyl-s-triazolo[1,5-a]pyrimidine To a suspension of 2-methoxycarbonyl-7-mercapto5-methyl-s-triazolo[1,5-a]pyrimidine (10 g) in 200 ml of methanol was dropwise added hydrazine hydrate (110 ml). The mixture was stirred at room temperature for two hours, the insoluble matters were filtered off, and the solvent was removed by distillation from the filtrate. Water (100 ml) was added to the residue and the pH was adjusted to 4.0 with 1N hydrochloric acid. The formed crystals were collected by filtration and washed with 100 ml of water, then with 100 ml of methanol, affording 7.2 g of the objective compound as yellow crystals.

M.P.: 221.0°–222.2° C.

(Step 2)

Preparation of (6R,7R)-7-[2-(2-amino-4-thiazolyl)-2-(Z-methoxyimino)acetamido]-3-[(2-hydrazinocarbonyl-5-methyl-s-triazolo[1,5-a]pyrimidin-7-yl)thiomethyl]-8-oxo-5-thia-1-azabicyclo[4.2.0]oct-2-ene-2-carboxylic acid Starting from the product obtained in Step 1 (7 g) and the product obtained in Step 2 of Example 7 (20 g), 11.5 g of the objective compound was obtained as colorless crystals in a manner similar to Step 4 of Example 37.

IR (KBr, cm$^{-1}$): 1770, 1640, 1530, 1040.
NMR (DMSO-d$_6$, δ): 9.6 (1H, d, 8 Hz), 6.9 (1H, s), 6.7 (1H,s), 3.8 (3H, s), 2.3 (3H, s).

EXAMPLE 42

Preparation of (6R,7R)-7-[2-(2-amino-4-thiazolyl)-2-(Z-methoxyimino)acetamido]-3-[(2-carboxy-5-hydroxy-s-triazolo[1,5-a]pyrimidin-7-yl)thiomethyl]-8-oxo-5-thia-1-azabicyclo[4.2.0]oct-2-ene-2-carboxylic acid (Compound 15)

(Step 1)

Preparation of 5-hydroxy-2-methoxycarbonyl-7-methylthio-s-triazolo[1,5-a]pyrimidine A suspension of ethyl 2-methylthiocarbonylacetate (37.6 g) an 3-amino-5-methoxycarbonyl-s-triazole (20 g) in dimethylformamide (200 ml) was refluxed for one hour. After removing the solvent by distillation under reduced pressure, ether was added to the residue, and the formed crystals were purified by silica gel chromatography, giving 11.7 g of the objective compound.

(Step 2)

Preparation of (6R,7R)-7-[2-(2-amino-4-thiazolyl)-2-(Z-methoxyimino)acetamido]-3-[(2-carboxy-5-hydroxy-s-triazolo[1,5-a]pyrimidin-7-yl)thiomethyl]-8-oxo-5-thia-1-azabicyclo[4.2.0]oct-2-ene-2-carboxylic acid The product obtained in Step 1 (2.1 g) was suspended in 0.1 M phosphate buffer (75 ml), and sodium bicarbonate (2.65 g) was added to this suspension to turn it into a solution. The solution was heated to 40° C., the product obtained in Step 2 of Example 7 (5 g) was added, and the reaction mixture was worked up in the manner similar to Step 4 of Example 37, affording 1.8 g of the objective compound.

IR (KBr, cm$^{-1}$): 1770, 1640, 1530, 1380, 1040, 750.
NMR (DMSO-d$_6$, δ): 9.8 (1H, d, 8 Hz), 7.4 (2H, bs), 6.9 (1H, s), 5.9 (1H, dd, 8 Hz, 5 Hz), 5.3 (1H, d, 5 Hz), 3.9 (3H, s).

EXAMPLE 43

Preparation of (6R,7R)-7-[2-(2-amino-4-thiazolyl)-2-(Z-methoxyimino)acetamido]-3-[(5-chloro-s-triazolo[1,5-a]pyrimidin-7-yl)thiomethyl]-8-oxo-5-thia-1-azabicyclo[4.2.0]oct-2-ene-2-carboxylic acid (Step 1)

Preparation of 5-chloro-7-mercapto-s-triazolo[1,5-a]pyrimidine

Thiourea (1.7 g) was added all at once to a solution of 4.2 g of 5,7-dichloro-s-triazolo[1,5-a]pyrimidine in 140 ml anhydrous ethanol at room temperature, the mixture was refluxed for 30 minutes, the crystals formed upon ice cooling were filtered off, and the filtrate was concentrated under reduced pressure. The residue was dissolved in 18 ml of 1N sodium hydroxide solution. The resulting solution was washed with 20 ml of ethyl acetate. The pH was adjusted to 1.0 with concentrated hydrochloric acid to give crystals. The crystals were collected by filtration and washed with 20 ml of water and then with 20 ml of methanol, affording 1.2 g of the objective compound as faint yellow crystals.

M.P.: >300° C.

(Step 2)

Preparation of (6R,7R)-7-[2-(2-amino-4-thiazolyl)-2-(Z-methoxyimino)acetamido]-3-[(5-chloro-s-triazolo[1,5-a]pyrimidin-7-yl)thiomethyl]-8-oxo5-thia-1-azabicyclo[4.2.0]oct-2-ene-2-carboxylic acid The product obtained in Step 1 (0.33 g) was suspended in 15 ml of 0.1M phosphate buffer, and 0.53 g of sodium bicarbonate and 1.0 g of the product obtained in Step 2 of Example 7 were added. The mixture was heated at 60° C. for five hours while maintaining the pH in the range of 6.8 to 7.2, and was worked up in the same manner as Step 4 of Example 37, affording 0.36 g of the objective compound.

IR (KBr, cm$^{-1}$): 1775, 1670, 1630, 1540, 1490, 1185, 1050, 875. NMR (DMSO-d$_6$, ppm): 9.7 (1H, d, 8 Hz), 8.9 (1H, s), 7.3 (2H, bs), 7.0 (1H, s), 6.8 (1H, s), 5.8 (1H, dd, 8 Hz, 5 Hz), 5.2 (1H, d, 5 Hz), 3.9 (3H, s). Example 44

Preparation of (6R,7R)-7-[2-(2-amino-4-thiazolyl)-2-(Z-methoxyimino)acetamido]-3-[(2-amino-5-methyl-s-triazolo[1,5-a]pyrimidin-7-yl)thiomethyl]-8-oxo-5-thia-1-azabicyclo[4.2.0]oct-2-ene-2-carboxylic acid (Compound 17)

(Step 1)

Preparation of 2-amino-7-chloro-5-methyl -s-triazolo[1,5-a]pyrimidine

2-Amino-7-hydroxy-5-methyl-s-triazolo[1,5-a]pyrimidine (20 g) was suspended in 120 ml of phosphorus oxychloride under ice cooling, and the suspension was refluxed for two hours. Excess phosphorus oxychloride was removed by distillation under normal pressure. The 40 ml of reddish brown oil left was shaken with 300 ml of dichloromethane and 200 ml of water and the organic layer was collected. The aqueous layer was again extracted with 200 ml of fresh dichloromethane, and the combined organic extract was treated with saturated sodium bicarbonate solution until the pH of washings rose to 7 to 8, then washed with 100 ml of saturated sodium chloride solution. After drying over anhydrous magnesium sulfate, the dried solution was concentrated under reduced pressure to about 30 ml, and the concentrate was crystallized using 80 ml of n-hexane, affording 17 g of the objective compound as faint yellow crystals.

(Step 2)

Preparation of 2-amino-7-mercapto-5-methyl-s-triazolo[1,5-a]pyrimidine

The product obtained in Step 1 (15 g) was added all at once at room temperature to a solution of 12 g of sodium hydrosulfide in 300 ml of water with stirring under a nitrogen stream. The mixture was stirred at room temperature for one hour, the insoluble matters were removed by filtration, the pH was adjusted to 1.0 with concentrated hydrochloric acid, and the formed crystals were collected by filtration and washed twice with 20 ml water, affording 11 g of the objective compound as yellow crystals. M.P.: >300° C.

(Step 3)

Preparation of (6R,7R)-7-[2-(2-amino-4-thiazolyl)-2-(Z-methoxyimino)acetamido]-3-[(2-amino-5-methyl-s-triazolo[1,5-a]pyrimidin-7-yl)thiomethyl]-8-oxo-5-thia-1-azabicyclo[4.2.0]oct-2-ene-2-carboxylic acid Sodium bicarbonate (8 g) and the product obtained in Stp 2 (6 g) were suspended in 240 ml of 0.1M phosphate buffer (pH 6.4). To this suspension the product obtained in Step 2 of Example 7 (15 g) was added at 40° C. The mixture was heated to 60° C. and the resulting clear, brown solution was stirred at that temperature for six hours while maintaining the pH between 6.8 and 7.2. After cooling to room temperature, the reaction mixture was washed twice with 100 ml of ethyl acetate, the aqueous layer was acidified with 1N hydrochloric acid to pH 2.0, and the formed crystals were collected by filtration and washed twice with 50 ml of 50% aqueous acetone, affording 11 g of the objective compound as colorless crystals.

IR (KBr, cm$^{-1}$): 1770, 1620, 1530, 1040.

NMR (DMSO-d$_6$, δ): 9.6 (1H, d, 8 Hz), 7.2 (1H, s), 6.7 (1H, s), 3.8 (3H, s), 2.6 (3H, s).

EXAMPLE 45

Preparation of (6R,7R)-7-[2-(2-amino-4-thiazolyl)-2-(Z-methoxyimino)-acetamido]-3-[(2-hydroxysulfonyl-5-methyl-s-triazolo[1,5-a]pyrimidin-7-yl)thiomethyl]-8-oxo-5-thia-1-azabicyclo[4.2.0]oct-2-ene-2-carboxylic acid (Compound 18)

(Step 1)

Preparation of 7-hydroxy-5-methyl-s-triazolo[1,5-a]pyrimidine-2-sulfonic acid

To a solution of 5.0 g 7-hydroxy-2-mercapto-5-methyl-s-triazolo-[1,5-a]pyrimidine and 2.2 g sodium hydroxide in 40 ml of water was added 63 ml of 30% hydrogen peroxide solution under ice cooling over a period of 15 minutes. The mixture was then heated at 85° C. for four hours with stirring, and the pH was lowered to 1.0 with concentrated hydrochloric acid. After concentrating to about 30 ml under reduced pressure, the separated crystals were collected by filtration and washed with 30 ml acetone, affording 5.5 g of the objective compound as colorless crystals.

M.P.: >300° C.

(Step 2)

Preparation of 7-chloro-2-chlorosulfonyl-5-methyl-s-triazolo[1,5-a]pyrimidine

To a suspension of the product obtained in Step 1 (10.0 g) in 40 ml of phosphorus oxychloride was dropwise added 5.5 ml of N,N-dimethylaniline under ice cooling over a period of 10 minutes. The mixture was stirred at room temperature for ten minutes and then refluxed for one hour. Excess phosphorus oxychloride was distilled away under reduced pressure, and the remaining bluish purple oil was shaken with 200 ml of chloroform and 150 ml of water. The chloroform layer was collected, and the aqueous layer was again extracted with 200 ml of fresh chloroform. The chloroform solutions were joined and washed twice with 200 ml of saturated sodium bicarbonate solution, once with 100 ml of saturated sodium chloride solution and dried over anhydrous sodium sulfate. The chloroform solution was concentrated under reduced pressure to about 20 ml, and 50 ml of n-hexane was added to this concentrate to give 6.2 g of the objective compound as faint green crystals.

M.P.: 270.0°-275.0° C.

(Step 3)

Preparation of 7-chloro-2-ethoxysulfonyl-5-methyl-s-triazolo[1,5-a]pyrimidine

To a suspension of the product obtained in Step 2 (3.5 g) was dropwise added 8.6 ml of 1M sodium ethoxide ethanol solution with vigorous stirring under ice cooling over a period of ten minutes. The mixture was stirred at room temperature for one hour, and the resulting yellow solution was concentrated under reduced pressure. The remaining yellow oil was shaken with 100 ml of chloroform and 50 ml of water. The chloroform layer was separated and the aqueous layer was again extracted with 100 ml of fresh chloroform. The chloroform layers were joined and washed with 100 ml of saturated sodium chloride solution and dried over anhydrous sodium sulfate. The chloroform solution was concentrated under reduced pressure, and 20 ml of n-hexane was added to the concentrate to give 1.8 g of the objective compound as faint yellow crystals.

M.P.: 166.0°-169.0° C.

(Step 4)

Preparation of 7-mercapto-5-methyl-s-triazolo[1,5-a]pyrimidine-2-sulfonic acid

The product obtained in Step 3 (6 g) was added to a solution of 8.1 g sodium hydrosulfide in 100ml of water all at once with stirring under a nitrogen at room temperature. The mixture was heated at 60° C. for four hours with stirring and cooled to room temperature. The resultant yellow solution was washed twice with 100 ml of ethyl acetate. The pH of the aqueous layer was lowered to 1.0 with concentrated hydrochloric acid for crystallization. The crystals were collected by filtration and washed with 20 ml of water; 3.2 g of the objective compound was obtained as yellow crystals.

M.P.: 254.0°-256.0° C.

(Step 5)

Preparation of (6R,7R)-7-[2-(2-amino-4-thiazolyl)-2(Z-methoxyimino)-acetamido]-3-[(2-hydroxysulfonyl-5-methyl-s-triazolo[1,5-a]pyrimidin-7-yl)thiomethyl]-8-oxo-5-thia-1-azabicyclo[4.2.0]oct-2-ene-2-carboxylic acid Sodium bicarbonate (0.3 g) and the product obtained in Step 2 of Example 7 (0.86 g) were added to a solution of the product obtained in Step 4 (0.44 g) in 10 ml of 0.1M phosphate buffer (pH 6.4) and heated at 60° C. for four hours, maintaining the pH in the range of 6.8 to 7.2. The solution was then worked up in the same manner as Step 4 of Example 37, affording 0.32 g of the objective compound.

IR (KBr, cm$^{-1}$): 1775, 1675, 1625, 1590, 1510, 1370, 1330, 1255.

NMR (DMSO-d$_6$, δ): 9.7 (1H, d, 8 Hz), 7.5 (1H, s), 7.3 (2H, bs) 6.8 (1H, s), 5.9 (1H, dd, 8 Hz, 5 Hz), 5.3 (1H, d, 5 Hz), 4.0 (3H, s), 2.3 (3H, s).

EXAMPLE 46

Preparation of (6R,7R)-7-[2-(2-amino-4-thiazolyl)-2-(Z-methoxyimino)acetamido]-3-[(5-methoxy-s-triazolo[1,5-a]pyrimidin-7-yl)thiomethyl]-8-oxo5-thia-1-azabicyclo[4.2.0]oct-2-ene-2-carboxylic acid (Compound 16)

(Step 1)

Preparation of 7-mercapto-5-methoxy-s-triazolo[1,5-a]pyrimidine

To a sodium methoxide solution, prepared from 1.4 g of sodium and 50 ml of methanol, was added all at once the product obtained in Step 1 of Example 43 (4.6 g under ice cooling. The mixture was refluxed for one hour, the solution was concentrated under reduced pressure, and the remaining yellow oil was dissolved in 50 ml water. The pH was adjusted to 1.0 with 1N hydrochloric acid, and the formed crystals were collected by filtration and washed with 30 ml ethanol, giving 1.7 g of the objective compound as faint yellow crystals.
M.P.: 182.1°–°183.2° C.

(Step 2)

Preparation of (6R,7R)-7-[2-(2-amino-4-thiazolyl)-2-(Z-methoxyimino)acetamido]-3-[(5-methoxy-s-triazolo[1,5-a]pyrimidin-7-yl)thiomethyl]-8-oxo- 5-thia-1-azabicyclo[4.2.0]oct-2-ene-2-carboxylic acid The product obtained in Step 1 (0.3 g) and the product obtained in Step 2 of Example 7 (0.95 g) were dissolved in a solution of 0.4 g sodium bicarbonate in ml of 0.1M phosphate buffer, and the mixture was worked up in the manner similar to Step 4 of Example 37, affording 0.32 g of the objective compound.
(KBr, cm$^{-1}$): 1770, 1660, 1640, 1530, 1385, 1020.
NMR (DMSO-$d_6$, $\delta$): 9.5 (1H, d, 8 Hz), 8.6 (1H, s), 7.1 (2H, bs), 6.8 (1H, s), 5.6 (1H, dd, 8 Hz, 5 Hz), 5.1 (1H, d, 5 Hz) 3.8 (3H, s), 3.1 (3H, s).

EXAMPLE 47

Preparation of (6R,7R)-7-[2-(2-amino-4-thiazolyl)-2-(Z-methoxyimino)acetamido]-3-[(7-hydroxy5-methyl-s-triazolo[1,5-a]pyrimidin-2-yl)thiomethyl]-8-oxo-5-thia-1-azabicyclo[4.2.0]oct-2-ene-2-carboxylic acid ( Step 1)

Preparation of 7-hydroxy-2-mercapto-5-methyl-s-triazolo[1,5-a]pyrimidine

A mixture of 3-amino-5-mercapto-s-triazole(10 g), ethyl acetoacetate(34 g), piperidine(10 ml) and ethanol(300 ml) was refluxed for four hours. After removing the solvent by distillation under reduced pressure, 150 ml water was added, the mixture was neutralized to pH 7.0 with hydrochloric acid and cooled, giving 5.9 g of the objective compound.

(Step 2)

Preparation of (6R,7R)-7-[2-(2-amino-4-thiazolyl)-2-(Z-methoxyimino)acetamido]-3-[(7-hydroxy-5-methyl-s-triazolo[1,5-a]pyrimidin-2-yl)thiomethyl]-8-oxo-5-thia-1-azabicyclo[4.2.0]oct-2-ene-2-carboxylic acid Starting from the product obtained in Step 1 (5.5 g) and the product obtained in Step 2 of Example 7 (15 g) and using 7.6 g of sodium bicarbonate and 240 ml of 0.1M phosphate buffer (pH 6.4), 12.3 g of the objective compound was obtained in a manner similar to Step 4 of Example 37.
IR (KBr, cm$^{-1}$): 1760, 1680, 1620, 1575, 1513, 1395, 1030.
NMR (DMSO-$d_6$, $\delta$): 9.6 (1H, d, 8 Hz), 8.3 (1H, s), 7.2 (2H, bs), 6.7 (1H, s), 5.7 (1H, dd, 8 Hz, 5 Hz), 5.1 (1H, d, 5 Hz), 3.8 (3H, s), 2.3 (3H, s)

EXAMPLE 48

Preparation of (6R,7R)-7-[2-(2-amino-4-thiazolyl)-2-Z-methoxyimino)acetamido]-3-[(6-ethoxycarbonyl-7-hydroxy-s-triazolo[1,5-a]pyrimidin-2-yl)thiomethyl]-8-oxo-5-thia-1-azabicyclo[4.2.0]oct-2-ene-2-carboxylic acid (Step 1)

Preparation of 6-ethoxycarbonyl-7-hydroxy-2-mercapto-s-triazolo[1,5-a]pyrimidine A mixture of 15 g 3-amino-5-mercapto-s-triazole, 28 g diethyl ethoxymethylenemalonate and 70 ml acetic acid was refluxed for 18 hours. After removing the solvent by distillation, the remaining brown oil was allowed to cool to room temperature, and the pH was adjusted to 10 with sodium hydroxide solution. After washing with 100 ml ethyl acetate, the brown aqueous solution was neutralized to pH 7.5 with 6N hydrochloric acid, and again washed with 100 ml ethyl acetate. The pH of the aqueous layer was lowered to 3.0 with 6N hydrochloric acid, and the separated crude product (12 g) was collected by filtration and recrystallized from 30 ml methanol, giving 9 g of the objective compound as colorless crystals.

(Step 2)

Preparation of (6R,7R)-7-[2-(2-amino-4-thiazolyl)-2-(Z-methoxyimino)acetamido]-3-[(6-ethoxycarbonyl -7-hydroxy-s-triazolo[1,5-a]pyrimidin-2-yl)thiomethyl]-8-oxo-5-thia-1-azabicyclo[4.2.0]oct-2-ene-2-carboxylic acid A solution of the product obtained in Step 1 (4.2 g) and sodium bicarbonate (4.4 g) in 160 ml of 0.1M phosphate buffer (pH 6.4) was heated at 40° C. with stirring. The product obtained in Step 2 of Example 7 (10 g) was added over a period of 30 minutes, and the resulting faint yellow solution was heated at 60° C. for two hours while maintaining the pH at 6.8 to 7.2. After cooling to room temperature, the brown solution was washed with 100 ml ethyl acetate, the pH was adjusted to 4.0 with 6N hydrochloric acid, and the aqueous solution was again washed with 100 ml ethyl acetate. The pH was then lowered to 2.0 with 6N hydrochloric acid, and the formed crystals were collected and washed with 10 ml of 50% aqueous acetone, affording 5.2 g of the objective compound as brown crystals.
IR (KBr, cm$^{-1}$): 3300, 1770, 1630, 1590, 1290, 1170, 1040.
NMR (DMSO-$d_6$, $\delta$): 9.4 (1H, d, 8 Hz), 8.6 (1H, s), 7.2 (1H, bs), 6.7 (1H, s), 5.7 (1H, dd, 8 Hz, 5 Hz), 5.1 (1H, d, 5 Hz), 4.2 (2H, q, 7 Hz), 3.8 (3H,s), 1.3 (3H, t, 7 Hz).

EXAMPLE 49

Preparation of (6R,7R)-7-[2-(2-amino-4-thiazolyl)-2-(Z-methoxyimino)acetamido]-3-[(6-carboxy7-hydroxy-s-triazolo[1,5-a]pyrimidin-2-yl)thiomethyl]-8-oxo-5-thia-1-azabicyclo[4.2.0]oct-2-ene-2-carboxylic acid (Compound 19) ( Step 1)

Preparation of 6-carboxy-7-hydroxy-2-mercapto-s-triazolo[1,5-a]pyrimidine

The product obtained in Step 1 of Example 48 (2.5 g) was added to a solution of 1.3 g sodium hydroxide dissolved in 20 ml of water and stirred at room temperature for four hours. The pH of the solution was adjusted to 1–2 with 6N hydrochloric acid. The formed crystals were collected by filtration, washed with 30 ml of water and dried, affording 2.2 g of the objective compound.

(Step 2)

Preparation of (6R,7R)-7-[2-(2-amino-4-thiazolyl)-2-(Z-methoxyimino)acetamido]-3-[(6-carboxy-7-hydroxy-s-triazolo[1,5-a]pyrimidin-2-yl)thiomethyl]-8-oxo-5-thia-1-azabicyclo[4.2.0]oct-2-ene-2-carboxylic acid A suspension containing the product obtained in Step 1 (1.05 g) and sodium bicarbonate (0.7 g) in 30 ml of 0.1M phosphate buffer (pH 6.4) was heated at 40° C. with stirring. The product obtained in Step 2 of Example 7 (2.0 g) was slowly added to the suspension and the resulting mixture was stirred at 60° C. for six hours while maintaining the pH in the range of 6.5 to 7.5. After cooling to room temperature, the reaction mixture was washed with 50 ml of ethyl acetate, the pH was adjusted to 2.0 with 1N hydrochloric acid, and the formed crystals were collected and washed twice with 30 ml of water and once with 30 ml of 50% aqueous acetone, affording 1.2 g of the objective compound. IR (KBr, cm$^{-1}$): 1785, 1720, 1675, 1625, 1540, 1235, 1170, 1040

NMR (DMSO-d$_6$, δ): 9.6 (1H, d, 8 Hz), 8.6 (1H, s), 6.8 (1H, s), 5.7 (1H, dd, 8 Hz, 5 Hz), 5.2 (1H, d, 5 Hz), 4.3 (2H, m), 3.8 (3H, s), 3.7 (2H, ABq)

EXAMPLE 50

Preparation of (6R,7R)-7-[2-(2-amino-4-thiazolyl)-2-(Z-methoxyimino)acetamido]-3-[(7-hydroxy-6-piperidinocarbonyl-s-triazolo[1,5-a]pyrimidin-2-yl)thiomethyl]-8-oxo-5-thia-1-azabicyclo[4.2.0]oct-2-ene-2-carboxylic acid (Step 1)

Preparation of 7-hydroxy-2-mercapto-6-piperidinocarbonyl-s-triazolo[1,5-a]pyrimidine To a solution of 7.3 g of 2-amino-5-mercapto-s-triazole and 27.0 g of diethyl ethoxymethylenemalonate in 250 ml of ethanol was slowly added 8.0 g of piperidine, the mixture was refluxed for seven hours and then allowed to stand overnight at room temperature. The formed crystals were collected by filtration and washed with 100 ml of ethanol, affording 10.2 g of the objective compound as colorless crystals.

(Step 2)

Preparation of (6R,7R)-7-[2-(2-amino-4-thiazolyl)-2-(Z-methoxyimino)acetamido]-3-[(7-hydroxy-6-piperidinocarbonyl-s-triazolo[1,5-a]pyrimidin2-yl)thiomethyl]-8-oxo-5-thia-1-azabicyclo[4.2.0]oct-2-ene-2-carboxylic acid A solution of the product obtained in Step 1 (0.58 g) and sodium bicarbonate (0.44 g) in 15 ml of 0.1M phosphate buffer (pH 6.4) and 5 ml of acetone was heated at 40° C. with stirring. The product obtained in Step 2 of Example 7 (1.0 g) was slowly added, and the resulting solution was heated at 60° C. for six hours while maintaining the pH between 6.5 and 7.5. After cooling to room temperature, the solution was washed with 15 ml of ethyl acetate, the pH was adjusted to 2.0 with 1N hydrochloric acid, and the formed crystals were collected and washed twice with 10 ml of water and once with 10 ml of 50% aqueous acetone, affording 0.65 g of the objective compound. IR (KBr, cm$^{-1}$): 1765, 1610, 1530, 1440, 1035, 850, 800.

NMR (DMSO-d$_6$, δ): 9.6 (1H, d, 8 Hz), 7.4 (1H, s), 7.2 (2H, bs), 5.7 (1H, dd, 8 Hz, 5 Hz), 5.1 (1H, d, 5 Hz), 3.8 (3H, s), 2.3 (3H, s).

EXAMPLE 51

Preparation of (6R,7R)-7-[2-(2-amino-4-thiazolyl)-2-(Z-methoxyimino)acetamido]-3-[(7-carboxy-s-triazolo[4,3-a]pyrimidin-5-yl)thiomethyl]-8-oxo-5-thia-1-azabicyclo[4.2.0]oct-2-ene-2-carboxylic acid (Step 1)

Preparation of 5-chloro-7-ethoxycarbonyl-s-tri azolo[4,3-a]pyrimidine

7-Ethoxycarbonyl-5-hydroxy-s-triazolo[4,3-a]pyrimidine (10 g) was added to 50 ml of phosphorus oxychloride at room temperature, the mixture was heated at 60° C. for one hour, and excess phosphorus oxychloride was removed by distillation under reduced pressure. The remaining dark red oil was shaken with 200 ml of chloroform and 100 ml of water, and the aqueous layer was again extracted with 100 ml of fresh chloroform. The chloroform layers were joined together and washed with 80 ml of saturated sodium bicarbonate solution and 100 ml of saturated sodium chloride solution and dried over anhydrous sodium sulfate. The dried solution was concentrated under reduced pressure to about 50 ml, and the residue was recrystallized from 100 ml of n-hexane. The crystals were collected by filtration, affording 6.2 g of the objective compound as faint yellow crystals.

(Step 2)

Preparation of 7-ethoxycarbonyl-5-mercapto-s-triazolo[4,3-a]pyrimidine

The product obtained in Step 1 (6 g) was added all at once under ice cooling to a solution of sodium hydrosulfide (5.5 g) in 100 ml of water, with stirring in nitrogen, and the mixture was stirred at room temperature for two hours. After filtering off the insoluble matters, the yellow filtrate was acidified to pH 2.0 with 6N hydrochloric acid, and the formed crystals were collected by filtration, washed with 20 ml of water and air-dried, affording 4.5 g of the objective compound as faint yellow crystals.

(Step 3)

Preparation of (6R,7R)-7-[2-(2-amino-4-thiazolyl)-2--(Z-methoxyimino)acetamido]-3-[(7-carboxy-s-triazolo[4,3-a]pyrimidin-5-yl)thiomethyl]-8-oxo-5-thia-1-azabicyclo[4.2.0]oct-2-ene-2-carboxylic acid A solution of the product obtained in Step 2 (3.8 g) and sodium bicarbonate (4.4 g) in 160 ml of 0.1M phosphate buffer (pH 6.4) was heated at 40° C. with stirring. The product obtained in Step 2 of Example 7 (10 g) was added over a period of 30 minutes, and the mixture was heated at 60° C. for five hours while maintaining the pH between 6.8 to 7.2. After cooling to room temperature, the brown solution was washed with 100 ml of ethyl acetate, the pH was adjusted to 4.0 with 6N hydrochloric acid, and the aqueous solution was again washed with 100 ml of ethyl acetate. The pH was then adjusted to 3.0 with 6N hydrochloric acid, and the formed crystals were collected and washed with 10 ml of 50% aqueous acetone, affording 4.3 g of the objective compound as light brown crystals.

IR (KBr, cm$^{-1}$): 3300, 1770, 1610, 1530, 1360, 1035, 740.

NMR (DMSO-d$_6$, δ): 9.6 (1H, d, 8 Hz), 8.6 (1H, s), 7.4 (1H, s), 7.2 (2H, bs), 6.7 (1H, s), 5.8 (1H, dd, 8 Hz, 5 Hz), 5.2 (1H, d, 5 Hz), 4.5 (2H, bs), 3.7 (2H, bs), 3.8 (3H, s).

EXAMPLE 52

Preparation of (6R,7R)-7-[2-(2-amino-4-thiazolyl)-2-Z-methoxyimino)acetamido]-3-[(7-carboxy-3-methyl-s-triazolo[4,3-a]pyrimidin-5-yl)thiomethyl]-8-oxo-5-thia-1-azabicyclo[4.2.0]oct-2-ene-2-carboxylic acid (Compound 20)

(Step 1)

Preparation of 7-ethoxycarbonyl-5-hydroxy-3-methyl-s-triazolo[4,3-a]pyrimidine

A suspension of 14.7 g of 3-amino-5-methyl-s-triazole and 26.8 g of ethyl acetylenedicarboxylate in 120 ml of ethanol was refluxed for three hours, the reaction mixture was allowed to stand at room temperature for one hour, and the formed crystals were collected by filtration. The filtrate was concentrated and the residue was recrystallized from dichloromethane, and the crystals were joined with those obtained above. Purification by silica gel chromatography gave 10.8 g of the objective compound as colorless crystals.

M.P.: 201.1°–203.2° C.

(Step 2)

Preparation of 5-chloro-7-ethoxycarbonyl-3-methyl-s-triazolo[4,3-a]pyrimidine

To a suspension of the product obtained in Step 1 (4.3 g) in 50 ml of phosphorus oxychloride was dropwise added 2.6 g of N,N-dimethylaniline at room temperature. The mixture was heated at 80° C. for one hour, excess phosphorus oxychloride was removed by distillation under reduced pressure, and the remaining reddish brown oil was shaken with 300 ml dichloromethane and 300 ml of water. The pH was adjusted to 7 to 8 with saturated sodium bicarbonate solution, the dichloromethane layer was collected, and the aqueous layer was again extracted with 200 ml of fresh dichloromethane. The chloroform layers were joined together, washed with saturated sodium chloride solution and dried over anhydrous magnesium sulfate. The dried filtrate was concentrated under reduced pressure, and the oily product left was purified by silica gel chromatography, giving 4.2 g of the objective compound as faint yellow crystals.

M.P.: 107.7°–109.7° C.

(Step 3)

Preparation of 7-ethoxycarbonyl-5-mercapto-3-methyl-s-triazolo[4,3-a]pyrimidine

The product obtained in Step 2 (4.0 g) was added at a time under ice cooling to a solution of 4.0 g of sodium hydrosulfide in 100 ml of water with stirring in nitrogen, and the mixture was stirred at room temperature overnight. The resulting solution was acidified to pH 1.0 with 6N hydrochloric acid, and the separated crystals were collected by filtration and recrystallized from ethanol, affording 3.2 g of the objective compound as orange crystals.

M.P.: 206.1°–207.5° C.

(Step 4)

Preparation of (6R,7R)-7-[2-(2-amino-4-thiazolyl)-2-(Z-methoxyimino)acetamido]-3-[(7-carboxy-3-methyl-s-triazolo[4,3-a]pyrimidin-5-yl)thiomethyl]-8-oxo-5-thia-1-azabicyclo[4.2.0]oct-2-ene-2-carboxylic acid A solution of the product obtained in Step 3 (1.0 g and sodium bicarbonate (0.7 g) in 30 ml of 0.1M phosphate buffer (pH 6.4) was heated at 40° C. with stirring. The product obtained in Step 2 of Example 7 (2.0 g) was added, and the mixture was heated at 60° C. for six hours while maintaining the pH between 6.8 and 7.2. After cooling to room temperature, the resulting solution was washed with 50 ml of ethyl acetate and the pH was adjusted to 2.6 with 1N hydrochloric acid. The formed crystals were collected by filtration and washed with 30 ml of water and with 30 ml of methanol in that order, affording 1.3 g of the objective compound as faint yellow crystals.

IR (KBr, cm$^{-1}$): 1770, 1600, 1360, 1040.

NMR (DMSO-d$_6$, δ): 9.6 (1H, d, 8 Hz), 7.4 (1H, s), 6.7 (1H, s) 3.8 (3H, s), 2.5 (3H, s).

EXAMPLE 53

Preparation of (6R,7R)-7-[2-(2-amino-4-thiazolyl)-2-(Z-methoxyimino)acetamido]-3-[(7-carboxy-5-hydroxy-s-triazolo[4,3-a]pyrimidin-3-yl)thiomethyl]-8-oxo-5-thia-1-azabicyclo[4.2.0]oct-2-ene-2-carboxylic acid (Compound 21)

(Step 1)

Preparation of 5-hydroxy-3-mercapto-7-methoxycarbonyl-s-triazolo[4,3-a]pyrimidine A mixture of 15.1 g of 3-amino-5-mercapto-s-triazole, 18.9 g of dimethyl acetylenedicarboxylate and 100 ml of ethanol was refluxed for 90 minutes. The objective compound (29 g) was obtained by collecting the crystals separated out upon cooling the reaction mixture.

(Step 2)

Preparation of 7-carboxy-5-hydroxy-3-mercapto-s-triazolo[4,3-a]pyrimidine

The product obtained in Step 1 (4.5 g) was added to a solution of 1.7 g potassium hydroxide in 50 ml water, and the mixture was refluxed for two hours. After cooling to room temperature, the solution was washed with 50 ml of ethyl acetate, the pH was adjusted to 1.0 with hydrochloric acid, and the formed crystals were collected by filtration, affording 3.9 g of the objective compound.

(Step 3)

Preparation of (6R,7R)-7-[2-(2-amino-4-thiazolyl)-2-(Z-methoxyimino)acetamido]-3-[(7-carboxy-5-hydroxy-s-triazolo[4,3-a]pyrimidin-3-yl)thiomethyl]-8-oxo-5-thia-1-azabicyclo[4.2.0]oct-2-ene-2-carboxylic acid Starting from the product obtained in Step 2 (6.7 g) and the product obtained in Step 2 of Example 7 (15 g) and using 240 ml of 0.1M phosphate buffer (pH 6.4) and 8.0 g of sodium bicarbonate, 3 g of the objective compound was obtained in a manner similar to Step 4 of Example 37.

IR (KBr, cm$^{-1}$): 1775, 1675, 1530, 1360, 1040.

NMR (DMSO-d$_6$, δ): 9.7 (1H, d, 8 Hz), 7.2 (2H, bs), 7.1 (1H, s), 6.7 (1H, s), 6.0–5.7 (1H, m), 5.3–4.9 (1H, m).

EXAMPLE 54

Preparation of (6R,7R)-7-[2-(2-amino-4-thiazolyl)-2-(Z-methoxyimino)acetamido]-3-[(7-carboxy-s-triazolo[1,5-c]pyrimidin-5-yl)thiomethyl]-8-oxo-5-thia-1-azabicyclo[4.2.0]oct-2-ene-2-carboxylic acid

(Step 1)

Preparation of 2-thiomethyl-4-carboxy-6-chloropyrimidine

S-methylthioorotic acid (13.0 g) was dropwise added to 80 ml of phosphorus oxychloride under ice cooling, the mixture was stirred at room temperature and then refluxed for two hours, and excess phosphorus oxychloride was removed by distillation under reduced pressure. The remaining red oil was shaken with 200 ml of ethyl acetate and 150 ml of water, the organic layer was separated and the aqueous layer was again extracted with 200 ml of fresh ethyl acetate. The organic layers were joined together and washed twice with 200 ml of saturated sodium bicarbonate solution, then with saturated sodium chloride solution, and dried over anhydrous sodium sulfate. The filtrate was concentrated under reduced pressure to about 20 ml and the residue was recrystallized from 50 ml of n-hexane, and the formed crystals were collected by filtration, affording 12.3 g of the objective compound as faint yellow crystals.

(Step 2)

Preparation of 4-carboxy-6-hydrazino-2-thiomethyl pyrimidine

A mixture of the product obtained in Step 1 (4.0 g) and hydrazine monohydrate was stirred at room temperature for one hour, the resulting solution was concentrated under reduced pressure, and the formed crystals were collected by filtration and washed with 50 ml of ethanol, then with 50 ml of ether, giving the objective compound as colorless crystals.

(Step 3)

Preparation of 7-carboxy-5-thiomethyl-s-triazolo[1,5-c]pyrimidine

A mixture of the product obtained in Step 2 (2.0 g) and formic acid (40 ml) was refluxed for 3.5 hours, the reaction mixture was allowed to stand at room temperature for 2 hours, and the formed crystals were collected by filtration. The resulting crystals were dissolved in 40 ml of acetic acid and the mixture was refluxed for 5 hours. After concentration under reduced pressure, the residue was dissolved in a small amount of saturated sodium bicarbonate solution and the solution was neutralized with 1N hydrochloric acid. The formed crystals were collected by filtration and washed with 30 ml of ethanol, then with 30 ml of ether, giving 1.1 g of the objective compound as colorless crystals.

(Step 4)

Preparation of 7-carboxy-5-mercapto-s-triazolo [1,5-c]pyrimidine

A mixture of the product obtained in Step 3 (0.86 g), sodium hydrosulfide (1.31 g) and glycerol (5 ml) was stirred at 130° C. for one hour. After cooling to room temperature, the resulting yellow solution was poured into 40 ml of water, then acidified to pH 2 to 3 with 1N hydrochloric acid. The formed crystals were collected by filtration and washed with 5 ml of water, then with 5 ml of ethanol, affording 0.7 g of the objective compound as faint yellow crystals.

(Step 5)

Preparation of (6R,7R)-7-[2-(2-amino-4-thiazolyl)-2-(Z-methoxyimino)acetamido]-3-[(7-carboxy-s-triazolo[1,5-c]pyrimidin-5-yl)thiomethyl]-8-oxo-5-thia-1-azabicyclo[4.2.0]oct-2-ene-2-carboxylic acid A mixture of the product obtained in Step 4 (0.34 g), sodium bicarbonate (0.53 g) and 0.1M phosphate buffer (15 ml) was heated at 40° C. with stirring. The product in Step 2 of Example 7 (1.0 g) was added over a period of 30 minutes, and the mixture was heated at 60° C. for five hours while maintaining the pH between 6.8 and 7.2. After cooling to room temperature, the resulting brown solution was washed with 10 ml of ethyl acetate and the pH was adjusted to 2.0 with 1N hydrochloric acid, and the formed crystals were collected and washed with 5 ml of methanol, affording 0.5 g of the objective compound as light brown crystals.

IR (KBr, cm$^{-1}$): 1770, 1630, 1525, 1470, 1400, 1040.

NMR (DMSO-d$_6$, δ): 9.6 (1H, d, 8 Hz), 8.8 (1H, s), 8.2 (1H, s), 7.2 (2H, bs), 6.7 (1H, s), 5.8 (1H, dd, 8 Hz, 5 Hz), 5.1 (1H, d, 5 Hz), 4.3 (2H, bs), 3.8 (3H, s).

EXAMPLE 55

Preparation of (6R,7R)-7-[2-(2-amino-4-thiazolyl)-2-(Z-methoxyimino)acetamido]-3-[(7-amino-s-triazolo[1,5-c]pyrimidin-5-yl)thiomethyl]-8-oxo-5-thia-1-azabicyclo[4.2.0]oct-2-ene-2-carboxylic acid (Compound 22)

(Step 1)

Preparation of 7-amino-5-mercapto-s-triazolo[1,5-c]pyrimidine

A mixture of 1,4,6-triamino-2(1H)-pyrimidinethione (2.0 g) and 40 ml of formic acid was refluxed for seven hours. After concentrating under reduced pressure, 80 ml of water was added to the residue, the mixture was refluxed for one hour, and the crystals formed upon cooling were collected by filtration and washed with methanol, giving 1.6 g of the objective compound as faint yellow crystals.

(Step 2)

Preparation of (6R,7R)-7-[2-(2-amino-4-thiazolyl)-2-(Z-methoxyimino)acetamido]-3[(7-amino-striazolo[1,5-c]pyrimidin-5-yl)thiomethyl]-8-oxo-5-thia-1-azabicyclo[4.2.0]oct-2-ene-2-carboxylic acid A mixture of the product obtained in Step 1 (0.35 g), sodium bicarbonate (0.35 g) and 0.1M phosphate buffer (15 ml) was heated at 40° C. with stirring. The product obtained in Step 2 of Example 7 (1.0 g) was added over a period of 30 minutes, and the mixture was heated at 60° C. for five hours while maintaining the pH between 6.8 and 7.2. After cooling to room temperature, the resulting brown solution was washed with 10 ml of ethyl acetate, the pH was adjusted to 3.0 with 1N hydrochloric acid, and the separated crystals were collected and washed with 10 ml of 60% aqueous acetone, 5 ml of water and 5 ml of acetone in that order, affording 0.3 g of the objective compound as faint yellow crystals.

IR (KBr, cm$^{-1}$): 1770, 1680, 1620, 1540, 1380, 1350, 1040.

NMR (DMSO-d$_6$, δ): 9.6 (1H, d, 8 Hz), 8.2 (1H, s), 7.2 (2H, bs), 6.7 (1H, s), 5.8 (1H, dd, 8 Hz, 5 Hz), 5.2 (1H, d, 5 Hz), 3.8 (3H, s).

EXAMPLE 56

Preparation of (6R,7R)-7-[2-(2-amino-4-thiazolyl)-2-(Z-methoxyimino)acetamido]-3-[(7-methyl-s-triazolo[1,5-c]pyrimidin-5-yl)thiomethyl]-8-oxo-5-thia-1-azabicyclo[4.2.0]oct-2-ene-2-carboxylic acid (Step 1)

Preparation of 5-mercapto-7-methyl-s-triazolo[1,5-c]pyrimidine

A mixture of 4-hydrazino-2-mercapto-6-methyl-pyrimidine (2.0 g) and 30 ml of formic acid was refluxed for three hours. After concentrating under reduced pressure, the residue was recrystallized from ether, and the crystals were collected by filtration, giving 1.85 g of the objective compound as faint yellow crystals.

(Step 2)

Preparation of (6R,7R)-7-[2-(2-amino-4-thiazolyl)-2-(Z-methoxyimino)acetamido]-3-[(7-methyl-s-triazolo[1,5-c]pyrimidin-5-yl)thiomethyl]-8-oxo-5-thia-1-azabicyclo[4.2.0]oct-2-ene-2-carboxylic acid A mixture of the product obtained in Step 1 (0.29 g), sodium bicarbonate (0.53 g) and 0.1M phosphate buffer (15 ml) was heated at 40° C. with stirring. The product obtained in Step 2 of Example 7 (1.0 g) was added over a period of 30 minutes, and the mixture was heated at 60° C. for five hours while maintaining the pH between 6.8 and 7.2. After cooling to room temperature, the resulting solution was washed with 10 ml of ethyl acetate and the pH was adjusted to 2.0 with 1N hydrochloric acid, and the formed crystals were collected and washed with 10 ml of methanol, affording 0.51 g of the objective compound as light brown crystals.

IR (KBr, cm$^{-1}$): 1770, 1655, 1615, 1530, 1470, 1385, 1040.

NMR (DMSO-d$_6$, δ): 9.6 (1H, d, 8 Hz), 8.6 (1H, s), 7.5 (1H, s), 7.2 (2H, bs), 6.7 (1H, s), 5.8 (1H, dd, 8 Hz, 5 Hz), 5.1 (1H, d, 5 Hz), 3.8 (3H, s), 2.5 (3H, s).

EXAMPLE 57

Preparation of (6R,7R)-7-[2-(2-amino-4-thiazolyl-2-(Z-methoxyimino)acetamido]-3-[(2-carboxy-7-methyl-s-triazolo[1,5-c]pyrimidin-5-yl)thiomethyl]-8-oxo-5-thia-1-azabicyclo[4.2.0]oct-2-ene-2-carboxylic acid (Step 1)

Preparation of 4-hydrazino-2-mercapto-6-methylpyrimidine

Hydrazine monohydrate (6.4 ml) was added dropwise to a suspension of 2,4-dimercapto-6-methylpyrimidine (7.0 g) in 100 ml of ethanol at room temperature, the mixture was refluxed for two hours, and the crystals formed upon cooling were collected by filtration and washed with 100 ml of ethanol, giving 6.4 g of the objective compound as yellow crystals.

(Step 2)

Preparation of 4-ethyloxalylhydrazino-2-mercapto-6-methylpyrimidine

Ethyloxalyl chloride (2.15 ml) was added dropwise to an ice-cooled suspension of the product obtained in Step 1 (3.0 g) in 50 ml of pyridine over a period of minutes, and the mixture was stirred under ice cooling for one hour. The temperature was allowed to rise slowly to room temperature, and stirring was continued for an additional one hour. The formed crystals were collected by filtration and washed with 50 ml of ethanol, affording 4.0 g of the objective compound as colorless crystals.

(Step 3)

Preparation of 2-ethoxycarbonyl-5-mercapto-7-methyl-s-triazolo[1,5-c]pyrimidine

A mixture of the product obtained in Step 2 (2.4 g) and 10 ml of acetic acid was refluxed for six hours. After cooling to room temperature, the insoluble matters were filtered off and the filtrate was concentrated in vacuo. The residue was dissolved in a small amount of methanol, and ether was added to cause crystallization, giving 1.6 g of the objective compound as faint yellow crystals.

(Step 4)

Preparation of (6R,7R)-7-[2-(2-amino-4-thiazolyl)-2-(Z-methoxyimino)acetamido]-3-[(2-carboxy-7-methyl-s-triazolo[1,5-c]pyrimidin-5-yl)thiomethyl]-8-oxo-5-thia-1-azabicyclo[4.2.0]oct-2-ene-2-carboxylic acid A mixture of the product obtained in Step 3 (0.42 g), sodium bicarbonate (0.53 g) and 0.1M phosphate buffer (15 ml) was heated at 40° C. with stirring. The product obtained in Step 2 of Example 7 (1.0 g) was added over a period of 30 minutes, and the mixture was heated at 60° C. for six hours while maintaining the pH at 6.8 to 7.2. After cooling to room temperature, the resulting solution was washed with 10 ml of ethyl acetate and the pH was adjusted to 2.0 with 1N hydrochloric acid. The formed crystals were collected and recrystallized from methanol/ether, affording 0.41 g of the objective compound as faint yellow crystals.

IR (KBr, cm$^{-1}$): 1770, 1735, 1670, 1640, 1535, 1370, 1255, 1040.

NMR (DMSO-d$_6$, δ): 9.6 (1H, d, 8 Hz), 7.5 (1H, s), 7.2 (2H, bs), 6.7 (1H, s), 5.8 (1H, dd, 8 Hz, 5 Hz), 5.1 (1H, d, 5 Hz) 3.8 (3H, s), 2.6 (3H, s).

EXAMPLE 58

Preparation of (6R,7R)-7-[2-(2-amino-4-thiazolyl)-2-(Z-methoxyimino)acetamido]-3-[(5-hydroxy-7-methyl-s-triazolo[4,3-c]pyrimidin-3-yl)-thiomethyl]-8-oxo-5-thia-1-azabicyclo[4.2.0]oct-2-ene-2-carboxylic acid (Compound 23)

(Step 1)

Preparation of 2-hydroxy-4-mercapto-6-methylpyrimidine

6-Methyluracil (25.0 g) was suspended in 1 liter of distilled pyridine with stirring and heated at 50° C. into solution. Phosphorus pentasulfide (12.6 g) was then added, and the mixture was refluxed for 20 hours. The solution was concentrated under reduced pressure, then the residue was refluxed with 500 ml of ethanol for one hour. Insoluble materials were removed by filtration and the filtrate was concentrated under reduced pressure. The residue was recrystallized from ethanol, affording 5.5 g of the objective compound as colorless crystals.

(Step 2)

Preparation of 4-hydrazino-2-hydroxy-6-methylpyrimidine

The product obtained in Step 1 (3.0 g) was suspended in 30 ml of ethanol at room temperature. Hydrazine monohydrate (3.17 g) was added dropwise to this suspension and the mixture was refluxed for two hours. After cooling to room temperature, the formed crystals were collected by filtration and washed with 20 ml of ethanol, giving 2.6 g of the objective compound as red crystals.

(Step 3)

Preparation of 5-hydroxy-3-mercapto-7-methyl-s-triazolo[4,3-c]pyrimidine

The product obtained in Step 2 (1.0 g) was added to a solution of 0.29 g of sodium hydroxide in 20 ml of 80% ethanol, 1.31 g of carbon disulfide was further added, and the mixture was refluxed for 24 hours. After concentrating under reduced pressure, the residue was dissolved in 10 ml of water and the pH was adjusted to 2.0 with 1N hydrochloric acid. The formed crystals were collected by filtration and washed with 10 ml of water and 10 ml of ethanol, affording 0.7 g of the objective compound as pink crystals.

(Step 4)

Preparation of (6R,7R)-7-[2-(2-amino-4-thiazolyl)-2-(Z-methoxyimino)acetamido]-3-[(5-hydroxy-7-methyl-s-triazolo[4,3-c]pyrimidin-3-yl)-thiomethyl]-8-oxo-5-thia-1-azabicyclo[4.2.0]oct-2-ene-2-carboxylic acid A mixture of the product obtained in Step 3 (0.38 g), sodium bicarbonate (0.53 g) and 0.1M phosphate buffer (15 ml) was heated at 40° C. with stirring. The product obtained in Step 2 of Example 7 (1.0 g) was added over a period of 30 minutes, and the mixture was further heated at 60° C. for six hours while maintaining the pH at 6.8 to 7.2. After cooling to room temperature, the resulting brown solution was washed with 20 ml of ethyl acetate and the pH was adjusted to 2.0 with 1N hydrochloric acid. The formed crystals were collected and washed with 10 ml of 60% aqueous acetone, 10 ml of water and 10 ml of acetone in that order, affording 0.3 g of the objective compound as yellow crystals.

IR (KBr, cm$^{-1}$): 1770, 1735, 1670, 1640, 1535, 1370, 1255, 1040, 760.

NMR (DMSO-d$_6$, δ): 12.0 (1H, s), 9.6 (1H, d, 8 Hz), 7.2 (2H, bs), 6.7 (1H, s), 6.5 (1H, s), 5.8 (1H, dd, 8 Hz, 5 Hz), 5.2 (1H, d, 5 Hz), 3.8 (3H, s), 2.5 (3H, s).

EXAMPLE 59

Preparation of (6R,7R)-7-[2-(2-amino-4-thiazolyl)-2--(Z-methoxyimino)acetamido]-3-[(7-methyl-5-oxo-5H-1,3,4-thiadiazolo[3,2-a]pyrimidin-2-yl)thiomethyl]8-oxo-5-thia-1-azabicyclo[4.2.0]oct-2-ene-2-carboxylic acid (Compound 24)

(Step 1)

Preparation of 2-mercapto-7-methyl-5-oxo-5H-1,3,4-thiadiazolo[3,2-a]pyrimidine

To a solution of 2-amino-5-mercapto-1,3,4-thiadiazole (4.0 g) and ethyl acetoacetate (4.3 g) in 50 ml ethanol, piperidine (2.55 g) was slowly added. The mixture was refluxed for seven hours and then allowed to stand overnight at room temperature. The formed crystals were collected by filtration and dissolved in 100 ml of water. The pH was adjusted to 2.0, and the formed crystals were collected and washed with 20 ml of water, affording 3.8 g of the objective compound as colorless crystals.

(Step 2)

Preparation of (6R,7R)-7-[2-(2-amino-4-thiazolyl)-2--(Z-methoxyimino)acetamido]-3-[(7-methyl-5-oxo-5H-1,3,4-thiadiazolo[3,2-a]pyrimidin-2-yl)thiomethyl]-8-oxo-5-thia-1-azabicyclo[4.2.0]oct-2-ene-2-carboxylic acid A mixture of the product obtained in Step 1 (0.42 g), sodium bicarbonate (0.53 g) and 0.1M phosphate buffer (20 ml, pH 6.4) was heated at 40° C. with stirring. The product obtained in Step 2 of Example 7 (1.0 g) was slowly added and the mixture was heated at 60° C. for six hours while maintaining the pH at 6.5 to 7.5. After cooling to room temperature, the resulting solution was washed with 30 ml of ethyl acetate and the pH was adjusted to 2.0 with 1N hydrochloric acid. The formed crystals were collected and washed twice with 10 ml of water and once with 10 ml of 50% aqueous acetone, affording 0.68 g of the objective compound as faint yellow crystals.

IR (KBr, cm$^{-1}$): 1760, 1660, 1620, 1570, 1390, 1030.

NMR (DMSO-d$_6$, δ): 9.6 (1H, d, 8 Hz), 7.4 (1H, s), 7.2 (2H, bs), 6.7 (1H, s), 5.8 (1H, dd, 8 Hz, 5 Hz), 5.1 (1H, d, 5 Hz) 4.2 (1H, d), 3.8 (3H, s), 2.3 (3H, s)

EXAMPLE 60

Preparation of (6R,7R)-7-[2-(2-amino-4-thiazolyl)-2-(Z-methoxyimino)acetamido]-3-[(6-carboxy-5-oxo-5H-b 1,3,4-thiadiazolo[3,2-a]pyrimidin-2-yl)thiomethyl]-8-oxo-5-thia-1-azabicyclo[4.2.0]oct-2-ene-2-carboxylic acid

(Step 1)

Preparation of 6-ethoxycarbonyl-2-mercapto-5-oxo-5H-1,3,4-thiadiazolo[3,2-a]pyrimidine A mixture of 2-amino-5-mercapto-1,3,4-thiadiazole (6.7 g), diethyl ethoxymethylenemalonate (16.2 g) and dimethylformamide (80 ml) was refluxed for 16 hours. After removing the solvent by distillation under reduced pressure, the residue was recrystallized from methanol, giving 10.3 g of the objective compound as colorless crystals.

(Step 2)

Preparation of 6-carboxy-2-mercapto-5-oxo-5H-1,3,4-thiadiazolo[3,2-a]pyrimidine

The product obtained in Step 1 (9.1 g) was added to a solution of 4.0 g of potassium hydroxide in 200 ml of water, and the mixture was heated at 60° C. for 30 minutes. After cooling to room temperature, the solution was washed with 200 ml of ethyl acetate and the pH was adjusted to 1.0 with hydrochloric acid. The formed crystals were collected by filtration and washed with ether, affording 6.5 g of the objective compound.

(Step 3)

Preparation of (6R,7R)-7-[2-(2-amino-4-thiazolyl)-2-(-Z-methoxyimino)acetamido]-3-[(6-carboxy-5-oxo-5H-1,3,4-thiadiazolo[3,2-a]pyrimidin-2-yl)thiomethyl]-8-oxo-5-thia-1-azabicyclo[4.2.0]oct-2-ene-2-carboxylic acid Starting from the product obtained in Step 2 (7.2 g) and the product obtained in Step 2 of Example 7 (15 g) in 240 ml of 0.1M phosphate buffer (pH 6.4) and 8.0 g of sodium bicarbonate, 4.8 g of the objective compound was obtained in a manner similar to Step 4 of Example 37.

IR (KBr, cm$^{-1}$): 1775, 1670, 1530, 1360, 1040.

NMR (DMSO-d$_6$, δ): 9.7 (1H, d, 8 Hz), 8.6 (1H, s), 7.3 (2H, bs), 6.7 (1H, s), 5.9 (1H, dd, 8 Hz, 5 Hz), 5.2 (1H, d, 5 Hz), 4.4 (2H, bs), 3.8 (3H, s), 3.6 (2H, bs)

EXAMPLE 61

Preparation of (6R,7R)-7-[2-(2-triphenylmethylamino-4-thiazolyl)-2-(Z-benzoyloxyimino)acetamido]-3-[(2-diphenylmethyloxycarbonyl-5-methyl-s-triazolo[1,5-a]pyrimidin-7-yl)thiomethyl]-8-oxo-5-thia-1-azabicyclo[4.2.0]oct-2-ene-2-carboxylic acid diphenylmethyl ester To an ice-cooled solution of the product obtained in Example 17 (0.5 g) in 12 ml of anhydrous dichloromethane, was added anhydrous potassium carbonate (0.07 g) with stirring, and the mixture was stirred under cooling with ice. A solution of benzoyl chloride (0.07 g) in dichloromethane (7 ml) was added over a period of 10 minutes and the mixture was stirred for one hour under ice cooling. The insoluble matters were filtered off and washed twice with 2 ml of dichloromethane, and the washings were joined with the filtrate. After concentrating the dichloromethane solution under reduced pressure, the brown residue (0.5 g) was crystallized with 10 ml of ether, affording 0.25 g of the objective compound as faint yellow crystals.

IR (KBr, cm$^{-1}$): 1791, 1743, 1596, 1525, 1521, 1507, 1498, 1450, 1242, 1202, 1182.

NMR (DMSO-d$_6$, δ): 10.0 (1H, d, 8 Hz), 9.0 (1H, s), 8.1–8.0 (2H, m) 7.5–7.1 (42H, m), 6.0 (1H, dd, 8 Hz, 5 Hz), 5.3 (1H, d, 5 Hz), 4.3 (2H, bs), 3.7 (2H, bs), 2.5(3H, s).

EXAMPLE 62

Preparation of (6R,7R)-7-[2-(2-triphenylmethylamino--4-thiazolyl)-2-(Z-benzoyloxyimino)acetamido]-3-[2-diphenylmethyloxycarbonyl-5-methyl-s-triazolo[1,5-a]pyrimidin-7-yl)thiomethyl]-8-oxo-5-thia-1-azabicyclo[4.2.0]oct-2-ene-2-carboxylic acid diphenylmethyl ester Triethylamine (32 μl) was added to a solution of benzoic acid (23 mg) in anhydrous dichloromethane (5 ml), and the resulting faint yellow solution was cooled to −10° C. Ethyl chloroformate (18 μl) was added to this solution and the mixture was stirred at that temperature for two hours. The resulting slurry was cooled to −40° C., and a solution of the product obtained in Example 17 (0.2 g) in 5 ml of dichloromethane was added. The mixture was stirred at that temperature for 20 minutes and at −10° C. for 20 minutes, and the temperature was allowed to rise to 0° C. over a period of 30 minutes. After removing the solvent by distillation under reduced pressure, 100 ml of ethyl acetate was added to the brown residue (0.25 g). The mixture was washed with 30 ml of 1N hydrochloric acid, 30 ml of saturated sodium bicarbonate solution and 50 ml of saturated sodium chloride solution in that order, and then dried over anhydrous sodium sulfate. Then the dried solution was concentrated under reduced pressure, and the brown residue (0.25 g) was purified by silica gel column chromatography using n-hexane/ethyl acetate as the eluent.

IR (KBr, cm$^{-1}$): 1791, 1743, 1596, 1525, 1521, 1507, 1498, 1450, 1242, 1202, 1182.

NMR (DMSO-d$_6$, δ): 10.0 (1H, d, 8 Hz), 9.0 (1H, s), 8.1–8.0 (2H, m) 7.5–7.1 (42H, m), 6.0 (1H, dd, 8 Hz, 5 Hz), 5.3 (1H, d, 5 Hz), 4.3 (2H, bs), 3.7 (2H, bs), 2.5 (3H, s).

These analytical results are in exact agreement with those obtained in Example 61.

EXAMPLE 63

Preparation of (6R,7R)-7-[2-(2-amino-4-thiazolyl)-2-(Z-benzoyloxyimino)acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid (Compound 25)

To an ice-cooled solution of the product obtained in Example 61(0.2 g) in anhydrous dichloroethane was added 0.11 ml of anisole and 0.22 ml of trifluoroacetic acid with stirring. The mixture was stirred under cooling with ice for 1.5 hours and then at room temperature for two hours. After concentrating the resulting solution under reduced pressure, 10 ml of ether was added to the reddish brown residue. The formed crystals were collected by filtration, affording 0.1 g of the objective compound as faint yellow crystals.

IR (KBr, cm$^{-1}$): 1778, 1735, 1619, 1598, 1200, 1020.

NMR (DMSO-d$_6$, δ): 10.0 (1H, d, 8 Hz), 8.2–8.0 (2H, m), 7.6 (5H, m), 7.40 (1H, s), 7.1 (1H, s), 5.9 (1H, dd, 5 Hz, 8 Hz), 5.3 (1H, d, 5 Hz), 4.4 (2H, bs), 4.1 (2H, bs), 2.6 (3H, s).

EXAMPLE 64

Preparation of 2-(2-triphenylmethylamino-4-thiazolyl)-2-(Z-benzoyloxyimino)acetic acid.

2-(2-Triphenylmethylamino-4-thiazolyl)-2-(Z-hydroxyimino)acetic acid (10 g) was suspended in 140 ml of anhydrous dichloromethane, and 6.7 ml of triethylamine was added to this suspension under ice cooling with stirring. To the resulting solution was added a solution of benzoyl chloride (3.2 g) in dichloromethane (20 ml). The mixture was stirred at room temperature for one hour, the insoluble matters were filtered off, and the filtrate was washed twice with 20ml 1N hydrochloric acid and 30 ml of saturated sodium chloride solution each and dried over anhydrous sodium sulfate. The dried filtrate was concentrated under reduced pressure, and the brown viscous residue (12 g) was purified by silica gel column chromatography using chloroform containing 10 to 15% methanol as eluent, giving 3 g of the objective compound as light brown crystals.

NMR (DMSO-d$_6$, δ): 9.0 (1H, s), 7.6–7.2 (21H, m).

EXAMPLE 65

Preparation of (6R,7R)-7-[2-(2-triphenylmethylamino--4-thiazolyl)-2-(Z-benzoyloxyimino)acetamido]-3-[(2-diphenylmethyloxycarbonyl-5-methyl-s-triazolo[1,5-a]pyrimidin-7-yl)thiomethyl]-8-oxo-5-thia-1-azabicyclo[4.2.0]oct-2-ene-2-carboxylic acid diphenylmethyl ester The product obtained in Example 64 (3 g) and the product obtained in Example 15 (4.3 g) were dissolved in anhydrous dichloromethane (200 ml). The faint yellow solution was cooled to −30° C. with stirring, and a solution of dicyclohexylcarbodiimide (1.2 g) in anhydrous dichloromethane (30 ml) was added by dropwise over a period of five minutes. The mixture was allowed to stand at 0° C. for nine hours, the insoluble matters were filtered off, and the filtrate was washed with 50 ml of 1N aqueous citric acid, 50 ml of saturated sodium bicarbonate solution and 80 ml of saturated sodium chloride solution in that order, and dried over anhydrous sodium sulfate. The dried filtrate was concentrated in vacuo, and the yellow viscous residue left (6.8 g) was purified by silica gel column chromatography using ethyl acetate hexane as eluent, yielding 5 g of the objective compound as faint yellow crystals.

IR (KBr, cm$^{-1}$): 1791, 1743, 1596, 1525, 1521, 1507, 1498, 1450, 1242, 1202, 1182.

NMR (DMSO-d$_6$, δ): 10.0 (1H, d, 8 Hz), 9.0 (1H, s), 8.1–8.0 (2H, m), 7.5–7.1 (42H, m), 6.0 (1H, dd, 8 Hz, 5 Hz), 5.3 (1H, d, 5 Hz), 4.3 (2H, bs), 3.7 (2H, bs), 2.5 (3H, s).

These analytical results are in exact agreement with those obtained in Example 62.

EXAMPLE 66

Preparation of (6R,7R)-7-[2-(2-triphenylmethyl amino-4-thiazolyl)-2-[Z-(2-pyrrolecarbonyl)oxyimino]acetamido]-3-[(2-diphenylmethyloxycarbonyl-5-methyl-s-triazolo[1,5-a]pyrimidin-7-yl)thiomethyl]-8-oxo-5-thia-1-azabicyclo[4.2.0]oct-2-ene-2-carboxylic acid diphenylmethyl ester.

Potassium carbonate (0.1 g) was added all at once to an ice-cooled solution of the product obtained in Example 17 (0.7 g) in 17 ml of anhydrous dichloromethane. A solution of 0.078 g of pyrrole-2-carboxylic acid chloride in 10 ml of dichloromethane was added by dropwise over a period of five minutes, and the mixture was stirred under ice cooling for 40 minutes and then at room temperature for three hours. After filtering off the insoluble matters, the filtrate was concentrated under reduced pressure, and the yellow residue was purified by silica gel column chromatography, giving 0.3 g of the objective compound as faint yellow crystals.

IR (KBr, cm$^{-1}$): 1786, 1739, 1595, 1526, 1449, 1375, 1058, 745.

(DMSO-d$_6$, δ): 12.0 (1H, brs), 9.8 (1H, d, 8 Hz), 9.0 (1H, s), 7.8–6.9 (41H, m), 6.2 (1H, m), 6.0 (1H, dd, 8 Hz, 5 Hz), 5.3 (1H, d, 5 Hz), 4.2 (2H, bs), 3.7 (2H, bs), 2.5 (3H, s).

EXAMPLE 67

Preparation of (6R,7R)-7-[2-(2-amino-4-thiazolyl)-2-[Z-(2-pyrrolecarbonyl)oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid (Compound 26)

The product obtained in Example 66 (0.3 g) was dissolved in 2.5 ml of dichloroethane. Then 0.16 ml of anisole and 0.32 ml of trifluoroacetic acid were added dropwise to the solution in this order under ice cooling, and the resulting yellow solution was stirred at room temperature for five hours. After concentrating under reduced pressure, the residue was subjected to crystallization with 30 ml of ether, affording 0.1 g of the objective compound as faint yellow crystals.

IR (KBr, cm$^{-1}$): 1774, 1733, 1700, 1637, 1112, 1063, 935, 748.

NMR (DMSO-d$_6$, δ): 12.0 (1H, s), 10.0 (1H, d, 8 Hz), 7.4 (1H, s), 7.3–7.0 (4H, m), 7.1 (1H, s), 6.2 (1H, m), 6.0 (1H, dd, 8 Hz, 5 Hz), 5.3 (1H, d, 5 Hz), 4.5 (2H, bs), 3.7 (2H, bs), 2.6 (3H, s).

EXAMPLE 68

Preparation of (6R,7R)-3-acetoxymethyl-7-[2-amino-4-thiazolyl-2-[Z-(3,4-methylenedioxybenzoyl)oxyimino]acetamido]-8-oxo-5-thia-1-azabicyclo[4.2.0]oct-2-ene-2-carboxylic acid (Step 1)

Preparation of (6R,7R)-3-acetoxymethyl-7-[2-(2-triphenylmethylamino-4-thiazolyl)-2-[Z-(3,4-methylenedioxybenzoyl)oxyimino]acetamido]-8-oxo-5-thia-1-azabicyclo[4.2 0]oct-2-ene-2-carboxylic acid diphenylmethyl ester The product obtained in Example 27 (8.0 g) and (6R,7R)-3-acetoxymethyl-7-amino-8-oxo-5-thia-1-azabicyclo[4.2.0]oct-2-ene-2-carboxylic acid diphenylmethyl ester (6.7 g) were dissolved in anhydrous dichloromethane (150 ml), the faint yellow solution was cooled on ice, and dicyclohexylcarbodiimide (3.2 g) was added. The mixture was stirred under ice cooling for one hour and then at room temperature for nine hours, the insoluble matters were filtered off, and the filtrate was washed with 100 ml of 1N aqueous citric acid, 100 ml of saturated sodium bicarbonate solution and 100 ml of saturated sodium chloride solution in that order, and dried over anhydrous sodium sulfate. The dried filtrate was concentrated in vacuo, and the yellow viscous residue (14.0 g) was purified by silica gel column chromatography using ethyl acetate/n-hexane as eluent, yielding 11.5 g of the objective compound as faint yellow crystals.

IR (KBr, cm$^{-1}$): 1780, 1730, 1520, 1260, 1030, 750, 700.

NMR (DMSO-d$_6$, δ): 10.6 (1H, d, 8 Hz), 9.0 (1H, s), 7.8–7.0 (30H, m), 6.1 (2H, s), 5.8 (1H, dd, 8 Hz, 5 Hz), 5.2 (1H, d, 5 Hz), 4.8 (2H, ABq), 3.6 (2H, bs), 2.0 (3H, s).

(Step 2)

Preparation of (6R,7R)-3-acetoxymethyl-7-[2-amino-4-thiazolyl-2-[Z-(3,4-methylenedioxybenzoyl)oxyimino]acetamido]-8-oxo-5-thia-1-azabicyclo[4.2.0]oct-2-ene-2-carboxylic acid Removal of the protecting groups from the compound obtained in Step 1 (11.5 g) in a manner similar to Example 26 gave 6.1 g of the objective compound as faint yellow crystals.

IR (KBr, cm$^{-1}$): 1780, 1740, 1450, 1265, 1040, 760.

NMR (DMSO-d$_6$, δ): 10.1 (1H, d, 8 Hz), 7.7 (1H, dd, 8 Hz, 1 Hz), 7.4 (1H, d, 1 Hz), 7.3 (2H, bs), 7.1 (1H, s), 7.0 (1H, d, 8 Hz), 6.1 (2H, s), 5.8 (1H, dd, 8 Hz, 5 Hz), 5.2 (1H, d, 5 Hz), 4.8 (2H, ABq), 3.6 (2H, bs), 2.0 (3H, s).

EXAMPLE 69

Preparation of (6R,7R)-7-[2-(2-amino-4-thiazolyl)-2-[Z-(3,4-methylenedioxybenzoyl)oxyimino]acetamido]-3 [(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid To a solution of the compound obtained in Example 1 (1.5 g) and sodium bicarbonate (2.2 g) in 70 ml of 0.1M phosphate buffer (pH 6.4) was added 5.0 g of the product obtained in Example 68, and the mixture was heated at 60° C. for six hours with stirring. After cooling to room temperature, the reaction mixture was washed with 50 ml of ethyl acetate, the aqueous layer was acidified to pH 3.0 with 6N hydrochloric acid, and the formed crystals were collected and washed twice with 50 ml each of methanol and aqueous acetone, affording 1.5 g of the objective compound as faint yellow crystals.

IR (KBr, cm$^{-1}$): 3400, 1774, 1739, 1580, 1500, 1250, 1030, 730.

NMR (DMSO-d$_6$, δ): 10.1 (1H, d, 8 Hz), 7.6 (1H, d, 9 Hz), 7.4 (1H, s), 7.4–7.2 (1H, m), 7.1 (1H, s), 7.0 (1H, d, 9 Hz), 6.1 (2H, s), 6.0 (1H, dd, 8 Hz, 5 Hz), 5.2 (1H, d, 5 Hz), 4.5 (2H, bs), 3.8 (2H, bs), 2.6 (3H, s).

EXAMPLE 70

Preparation of (6R,7R)-7-[2-(2-triphenylmethylamino-4-thiazolyl)-2-[Z-(3,4-diacetoxybenzoyl)oxyimino]acetamido]-3-[(2-diphenylmethyloxycarbonyl-5-methyl-s-triazolo[1,5-a]pyrimidin-7-yl)thiomethyl]-8-oxo-5-thia-1-azabicyclo[4.2.0]oct-2-ene-2-carboxylic acid diphenylmethyl ester.

Potassium carbonate (0.43 g) was added all at once to an ice-cooled solution of the product obtained in Example 17 (3.0 g) in 60 ml of anhydrous dichloromethane. A solution of 0.79 g of 3,4-diacetoxybenzoyl chloride in 40 ml of dichloromethane was added dropwise over a period of 15 minutes, and the mixture was stirred under ice cooling for one hour and then at room temperature for one hour. After filtering off the insoluble matters, the filtrate was washed with 20 ml of water and 10 ml of saturated sodium chloride solution. The organic layer was dried over anhydrous sodium sulfate, and the solvent was removed by distillation under reduced pressure, and the residue was treated with ether. The formed crystals were washed twice with ether, giving 3.2 g of the objective compound as yellow crystals.

IR (KBr, cm$^{-1}$): 1779, 1744, 1498, 1279, 1201, 1187, 700.

NMR (DMSO-d$_6$, δ): 10.0 (1H, d, 8 Hz), 9.0 (1H, s), 7.8–6.8 (42H, m), 5.9 (1H, dd, 8 Hz, 5 Hz), 5.3 (1H, d, 5 Hz), 4.2 (2H, bs), 3.5 (2H, bs), 2.5 (3H, s), 2.3 (3H, s), 2.2 (3H, s).

EXAMPLE 71

Preparation of (6R,7R)-7-[2-(2-amino-4-thiazolyl)-2-[Z-(3,4-diacetoxybenzoyl)oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid (Compound 27)

The product obtained in Example 70 (3.2 g) was dissolved in 20 ml of dichloroethane. Then 1.7 ml of anisole, 3.3 ml of trifluoroacetic acid and two drops of water were dropwise added to the solution in this order by under ice cooling, and the resulting red solution was stirred at room temperature for three hours. After concentrating under reduced pressure, the residue was subjected to crystallization with 40 ml of ether, affording 2.2 g of the objective compound as yellow crystals.

IR (KBr, cm$^{-1}$): 1773, 1764, 1597, 1509, 1281, 1262, 1207, 1164.

NMR (DMSO-d$_6$, δ): 10.3 (1H, d, 8 Hz), 7.9 (2H, m), 7.6–7.1 (5H, m), 6.0 (1H, dd, 8 Hz, 5 Hz), 5.3 (1H, d, 5 Hz), 4.5 (2H, bs), 3.8 (2H, ABq), 2.6 (3H, s), 2.3 (3H, s), 2.2 (3H, s)

EXAMPLE 72

Preparation of (6R,7R)-7-[2-(2-amino-4-thiazolyl)-2-(Z-methoxyimino)acetamido]-3-[(2-carboxy-5-methyl-s-triazolo[1,5-a]pyrimidin-7-yl)-thiomethyl]-8-oxo-5-thia-1-azabicyclo[4.2.0]oct-2-ene-2-carboxylic acid (Compound 2)

(Step 1)

Preparation of (6R,7R)-3-[(2-carboxy-5-methyl-striazolo[1,5-a]pyrimidin-7-yl)thiomethyl]-7-[2(2-chloroacetamido-4-thiazolyl)-2-(Z-methoxyimino)acetamido]-8-oxo-5-thia-1-azabicyclo[4.2.0]oct-2-ene-2-carboxylic acid Triethylamine (0.69 g) was added to a solution of 2-(2-chloroacetamido-4-thiazolyl)-2-(Z-methoxyimino)acetic acid (1.5 g) in 10 ml of dichloromethane, and 1.2 g of phosphorous pentachloride was then added by drops at 0° C. over a period of ten minutes. After stirring the mixture at 0° C. for ten minutes and then at room temperature for one hour, dichloromethane was removed by distillation under reduced pressure, the residue was washed twice with 5 ml of n-hexane to remove excess phosphorus pentachloride, the brown residue was dissolved in 10 ml of tetrahydrofuran, and the phosphorus pentachloride still left was removed by filtration. This acid chloride solution in tetrahydrofuran was added dropwise under ice cooling over a period of 5 minutes to the solution of the product obtained in Example 14 (2.2 g) and bis(trimethylsilyl)acetamide (3.1 g) in 50 ml of dry dichloromethane, and the mixture was stirred at room temperature for two hours. After removing the solvent by distillation under reduced pressure, the brown residue was added to a mixture of 25 ml of ethyl acetate and 10 ml of water, and the pH was adjusted to 7.5 with sodium bicarbonate, followed by washing with ethyl acetate. The aqueous layer was collected, its pH was lowered to 2.0 with 1N hydrochloric acid, the crystals thus formed were collected by filtration, washed twice with 10 ml of water and then once with 5 ml of 50% aqueous acetone, and thoroughly dried, giving 1.8 g of the objective compound as brown crystals.

IR (KBr, cm$-1$): 1770, 1690, 1600, 1550, 1500, 1040.

NMR (DMSO-d$_6$,δ): 9.5 (1H, s), 8.1 (1H, d, 8 Hz), 7.4 (1H, s), 6.8 (1H, s), 4.7 (2H, s), 3.8 (3H, s), 2.5 (3H, s).

(Step 2)

Preparation of (6R,7R)-7-[2-(2-amino-4-thiazol yl)-2-(Z-methoxyimino)acetamido]-3-[(2-carboxy-5-methyl-s-triazolo [1,5-a]pyrimidin-7-yl)thio-methyl]-8-oxo-5-thia-1-azabicyclo[4.2.0]oct-2-ene-2-carboxylic acid.

The product obtained in Step 1 (1.8 g) was dissolved in 30 ml of dimethylacetamide, 0.5 g of thiourea was added to this solution at room temperature in small portions over a period of ten minutes, and the mixture was stirred at room temperature for an additional nine hours. After concentration of the reaction mixture under reduced pressure, 80 ml of ethyl acetate and 200 ml of water were added to the brown residue, the pH was adjusted to 7.8 with sodium bicarbonate, and the aqueous layer was washed with ethyl acetate until no thiourea could be detected in the aqueous layer. The pH of aqueous layer was lowered to 3.5, the crystals thus formed were collected by filtration, washed twice with 20 ml of water and then once with 5 ml of 50% aqueous acetone, and dried, giving 0.9 g of the objective compound as colorless crystals.

IR (KBr, cm$^{-1}$): 1770, 1625, 1510, 1040. NMR (DMSO-d$_6$,δ): 9.6 (1H, d, 8 Hz), 7.4 (1H, s), 6.7 (1H, s), 3.8 (3H, s), 2.6 (3H, s).

These analytical results are in exact agreement with those obtained in Example 7.

Example 73

Preparation of (6R,7R)-7-[2-(2-triphenylmethyl-amino-4-thiazolyl)-2-[Z-(3,4,5-triacetoxybenzo-yl)oxyimino]acetamido]-3-[(2-diphenylmethyloxy-carbonyl-5-methyl-s-triazolo [1,5-a]pyrimidin-7-yl)thiomethyl]-8-oxo-5-thia-1-azabicyclo[4.2.0]-oct-2-ene-2-carboxylic acid diphenylmethyl ester.

Potassium carbonate (0.28 g) was added all at once to an ice-cooled solution of the product obtained in Example 17 (2.0 g) in 50 ml of anhydrous dichloromethane. A solution of 0.65 g of 3,4,5-triacetoxybenzoyl chloride in 30 ml of dichloromethane was added dropwise over a period of 5 minutes, and the mixture was stirred under ice cooling for 15 minutes. After filtering off the insoluble matters, the solvent was removed by distillation under reduced pressure, and the residue was treated with ether. The formed crystals were washed twice with ether, giving 2.3 g of the objective compound as pale yellow crystals.

IR (KBr, cm$^{-1}$): 1783, 1750, 1595, 1508, 1323, 1183, 700.

NMR (DMSO-d$_6$,δ): 10.1 (1H, d, 8 Hz), 9.3 (1H, bs), 7.8–6.8 (4lH, m), 5.9 (1H, dd, 8 Hz, 5 Hz), 5.3 (1H, d, 5 Hz), 4.3 (2H, bs), 3.6 (2H, bs), 2.5 (3H, s), 2.3 (6H, s), 2.2 (3H, s).

EXAMPLE 74

Preparation of (6R,7R)-7-[2-(2-amino-4-thiazol-yl)-2-[Z-(3,4,5-triacetoxybenzoyl)oxyimino]acet-amido ]-3-[(2-carboxy-5-methyl-s-triazolo[1,5-a]-pyrimidin-7-yl) thiomethyl]-8-oxo-5-thia-1-aza-bicyclo [4.2.0]oct-2-ene-2-carboxylic acid.

(Compound 13)

The product obtained in Example 73 (1.7 g) was dissolved in 15 ml of dichloroethane. Then 0.8 ml of anisole, 1.6 ml of trifluoroacetic acid and two drops of water were added dropwise to the solution in this order under ice cooling, and the resulting red solution was stirred at room temperature for three hours. After concentrating under reduced pressure, the residue was subjected to crystallization with 40 ml of ether, affording 0.9 g of the objective compound as yellow crystals.

IR (KBr, cm$^{-1}$): 1779, 1775, 1597, 1509, 1324, 1190, 1055.

NMR (DMSO-d$_6$,δ): 10.1 (1H, d, 8 Hz), 7.8 (2H, s), 7.4 (1H, s), 7.2 (1H, s), 5.9 (1H, dd, 8 Hz, 5 Hz), 5.2 (1H, d, 5 Hz), 4.5 (2H, bs), 3.7 (2H, ABq), 2.6 (3H, s), 2.4 (3H, s), 2.3 (6H, s).

Typical compounds of this invention are summarized below in Tables 4-through 4-f.

TABLE 4-a

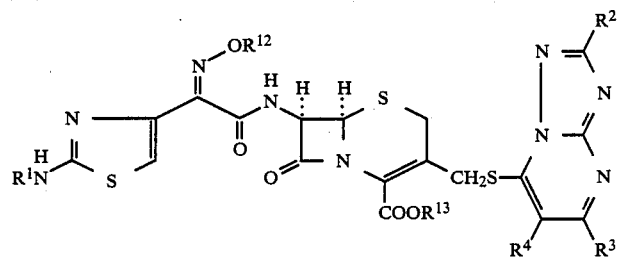

| Example No. (Compound No.) | R$^1$ | R$^2$ | R$^3$ | R$^4$ | R$^{12}$ | R$^{13}$ |
|---|---|---|---|---|---|---|
| 8 (1) | H | H | CH$_3$ | H | CH$_3$ | H |
| 7 (2) | H | COOH | CH$_3$ | H | CH$_3$ | H |
| 9 (3) | H | H | H | COOH | CH$_3$ | H |
| 11 (4) | H | CH$_2$COOH | CH$_3$ | H | CH$_3$ | H |
| 10 (5) | H | H | CH$_2$COOH | H | CH$_3$ | H |
| 12 (6) | H | H | COOH | H | CH$_3$ | H |
| 13 (7) | H | COOH | H | COOH | CH$_3$ | H |
| 18 (8) | H | COOH | CH$_3$ | H | H | H |
| 20 (9) | H | COOH | CH$_3$ | H | CO—furyl(O) | H |
| 22 (10) | H | COOH | CH$_3$ | H | CO—thienyl(S) | H |
| 24 (11) | H | COOH | CH$_3$ | H | CO—pyridyl(N) | H |
| 26 (12) | H | COOH | CH$_3$ | H | CO—benzodioxolyl | H |
| 32 | H | COOH | CH$_3$ | H | COCH$_2$SCH$_2$CN | H |

TABLE 4-a-continued

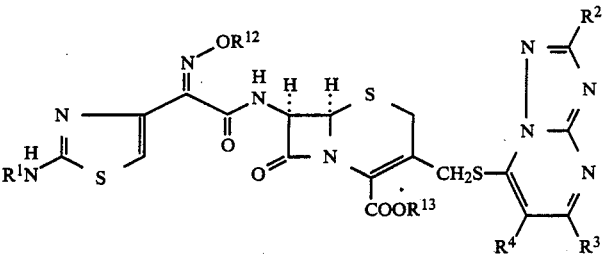

| Example No. (Compound No.) | R¹ | R² | R³ | R⁴ | R¹² | R¹³ |
|---|---|---|---|---|---|---|
| 34 | H | COOH | CH₃ | H | COCH₂—(2-thienyl) | H |
| 36 | H | COOH | CH₃ | H | CO—CH=CH—(2-furyl) | H |
| 63 (25) | H | COOH | CH₃ | H | CO—phenyl | H |
| 67 (26) | H | COOH | CH₃ | H | CO—(2-pyrrolyl) | H |
| 37 | H | COOH | CH(CH₃)₂ | H | CH₃ | H |
| 38 (14) | H | COOH | H | H | CH₃ | H |
| 39 | H | COOH | CH₃ | CH₃ | CH₃ | H |
| 40 | H | CH₃ | COOH | H | CH₃ | H |
| 41 | H | CONHNH₂ | CH₃ | H | CH₃ | H |
| 42 (15) | H | COOH | OH | H | CH₃ | H |
| 46 (16) | H | H | OCH₃ | H | CH₃ | H |
| 44 (17) | H | NH₂ | CH₃ | H | CH₃ | H |
| 45 (18) | H | SO₃H | CH₃ | H | CH₃ | H |
| 43 | H | H | Cl | H | CH₃ | H |
| 71 (27) | H | COOH | CH₃ | H | CO—(3,4-diacetoxyphenyl) | H |
| 74 (13) | H | COOH | CH₃ | H | CO—(2,3,4-triacetoxyphenyl) | H |

TABLE 4-b

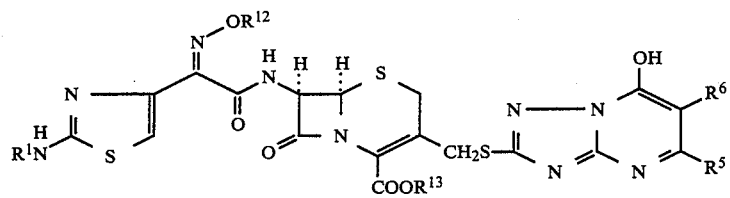

| Example No. (Compound No) | $R^1$ | $R^5$ | $R^6$ | $R^{12}$ | $R^{13}$ |
|---|---|---|---|---|---|
| 47 | H | $CH_3$ | H | $CH_3$ | H |
| 49 (19) | H | H | COOH | $CH_3$ | H |
| 48 | H | H | $COOC_2H_5$ | $CH_3$ | H |
| 50 | H | H | CON⟨piperidine⟩ | $CH_3$ | H |

TABLE 4-c

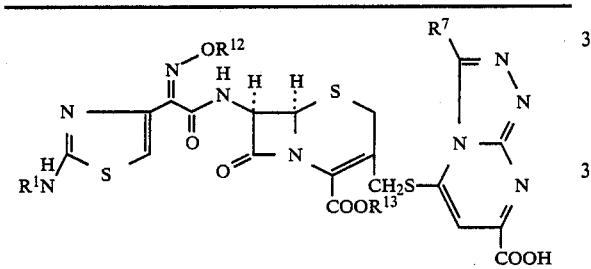

| Example No. (Compound No.) | $R^1$ | $R^7$ | $R^{12}$ | $R^{13}$ |
|---|---|---|---|---|
| 51 | H | H | $CH_3$ | H |
| 52 (20) | H | $CH_3$ | $CH_3$ | H |

TABLE 4-d

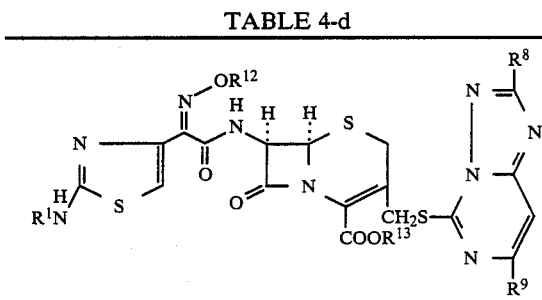

| Example No. (Compound No.) | $R^1$ | $R^8$ | $R^9$ | $R^{12}$ | $R^{13}$ |
|---|---|---|---|---|---|
| 54 | H | H | COOH | $CH_3$ | H |
| 55 (22) | H | H | $NH_2$ | $CH_3$ | H |
| 56 | H | H | $CH_3$ | $CH_3$ | H |
| 57 | H | COOH | $CH_3$ | $CH_3$ | H |

TABLE 4-e

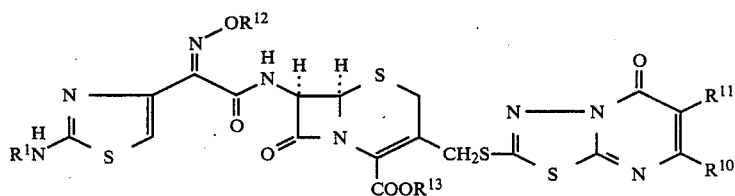

| Example No. (Compound No.) | $R^1$ | $R^{10}$ | $R^{11}$ | $R^{12}$ | $R^{13}$ |
|---|---|---|---|---|---|
| 59 (24) | H | $CH_3$ | H | $CH_3$ | H |
| 60 | H | H | COOH | $CH_3$ | H |

EXAMPLE NO. 53
(Compound No. 21)

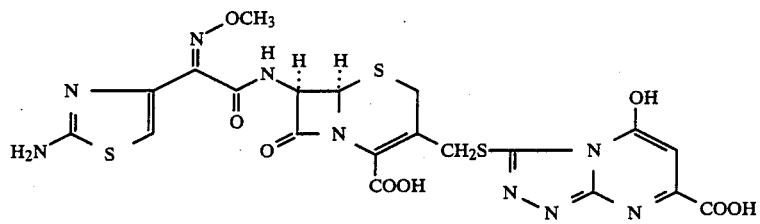

EXAMPLE NO. 58
(Compound No. 23)

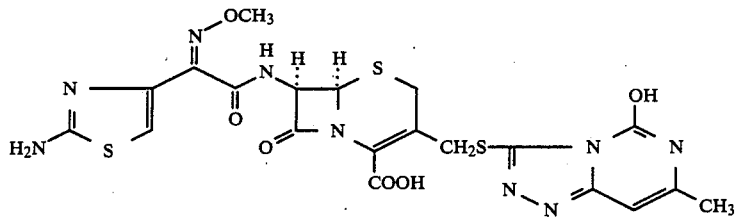

TABLE 4-f

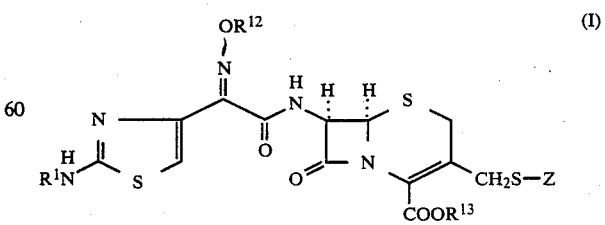

| Example No. (Compound No.) | $R^1$ | $R^{12}$ | $R^{14}$ |
|---|---|---|---|
| 29 | $(C_6H_5)_3C$ | CO—⟨furan⟩ | H |
| 27 | $(C_6H_5)_3C$ | CO—⟨benzodioxole⟩ | H |
| 64 | $(C_6H_5)_3C$ | CO—⟨phenyl⟩ | H |

The following examples detail typical pharmaceutical preparations containing the cephalosporin derivatives of the present invention. These examples are not intended to limit the types of compounds to be used, but the methods are applicable to all the compounds of this invention.

EXAMPLE A
(Method of manufacturing freeze-dried parenteral injections)

(6R,7R)-7-[2-(2-amino-4-thiazolyl)-2-(Z-methoxyimino)acetamido]-3-[(2-carboxy-5-methyl-s-triazolo[1,5-a]pyrimidin-7-yl)thiomethyl-8-oxo-5-thia-1-azabicyclo[4.2.0]oct-2-ene-2-carboxylic acid (1.1 g) was dissolved in 22 ml of sterile water containing an equivalent amount of sodium bicarbonate, and 2 ml each of this solution was poured into 5-ml ampoules, freeze dried and sealed by ordinary methods to produce freeze dried preparation for parenteral injections.

EXAMPLE B
(Method of manufacturing tablets for oral administration)

Granules were prepared by ordinary method using 250 mg of (6R,7R)-7-[2-(2-amino-4-thiazolyl) -2-[Z-(3,4-diacetoxybenzoyl)oxyimino)acetamido]-3-[ (2-carboxy-5-methyl-s-triazolo[1,5-a]pyrimidin-7-yl)thiomethyl]-8-oxo-5-thia-1-azabicyclo[4.2.0]oct-2-ene-2carboxylic acid, 100 mg of lactose, 30 mg of starch and 10 mg of polyvinyl pyrrolidone. Starch (30 mg) and magnesium stearate (5 mg) were further added to the granules, and the resulting mixture was compressed into tablets, each piece weighing 425 mg.

EXAMPLE C
(Method of manufacturing gelatin capsules for oral administration)

(6R,7R)-7-[2-(2-amino-4-thiazolyl)-2-(Z-(2-furancarbonyl)oxyimino)acetamido]-3-[(2-carboxy-5-methyl-s-triazolo [1,5-a]pyrimidin-7-yl)thiomethyl]-8-oxo-5-thia-1-azabicyclo [4.2.0]oct-2-ene-2-carboxylic acid (250 mg), water-soluble polyvinyl pyrrolidone (15 mg), mannitol (15 mg), talc (15 mg) and magnesium stearate (5 mg) were uniformly mixed, giving gelatin capsules, each piece weighing 300 mg.

What is claimed is:
1. A compound of the formula (I):

and salts, hydrates and hydrates of salts of said cephalosporin compound; wherein $R^1$ represents a hydrogen atom or an amino-protecting group; Z represents:

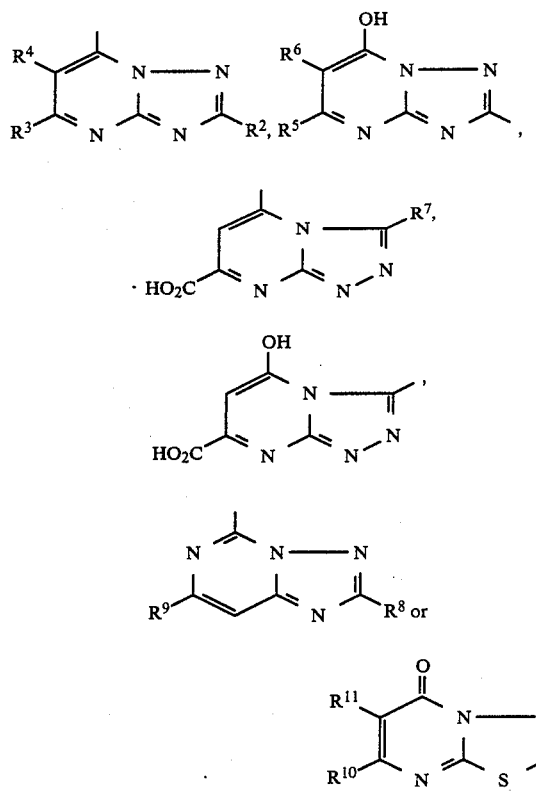

wherein $R^2$ represents a hydrogen atom, a methyl group, an amino group, a cyano group, a hydroxysulfonyl group, a carboxyl group, a carboxymethyl group, a protected carboxyl group, a protected carboxymethyl group, a methoxycarbonyl group or a hydrazino carbonyl group; $R^3$ represents a hydrogen atom, an alkyl group having 1 to 3 carbon atoms, a hydroxy group, a methoxy group, a carboxyl group, a carboxymethyl group or a chlorine atom; $R^4$ represents a hydrogen atom, a methyl group or a carboxyl group; $R^5$ represents a hydrogen atom or a methyl group; $R^6$ represents a hydrogen atom, a carboxyl group, an ethoxycarbonyl group or a piperidinocarbonyl group; $R^7$ represents a hydrogen atom or a methyl group; $R^8$ represents a hydrogen atom or a carboxyl group; $R^9$ represents a methyl group, an amino group or a carboxyl group; $R^{10}$ represents a hydrogen atom or a methyl group; $R^{11}$ represents a hydrogen atom or a carboxyl group; $R^{12}$ represents a hydrogen atom, a methyl group, a hydroxyl-protecting group, a cyanomethyl-thioacetyl group a monocyclic carbocyclic aromatic acyl group which may be substituted by protected or non-protected hydroxy groups or a mono- or dicyclic heterocyclic aromatic acyl group; $R^{13}$ represents a hydrogen atom or a carboxyl-protecting group; and a wavy line represents a bond of anti-form or of syn-form.

2. A compound as claimed in claim 1 wherein said wavy line represents a bond of syn-form.

3. A compound as claimed in claim 1 which is represented by the formula (Ia):

4. A compound as claimed in claim 3 wherein $R^2$ and $R^4$ each represent a hydrogen atom and $R^3$ represents a methyl group.

5. A compound as claimed in claim 3 wherein $R^2$ represents a carboxyl group, $R^3$ represents a methyl group and $R^4$ represents a hydrogen atom.

6. A cephalosporin compound as claimed in claim 3 wherein $R^2$ and $R^3$ each represent a hydrogen atom and $R^4$ represents a carboxyl group.

7. A compound as claimed in claim 3 wherein $R^2$ represents a carboxymethyl group, $R^3$ represents a methyl group and $R^4$ represents a hydrogen atom.

8. A compound as claimed in claim 3 wherein $R^2$ and $R^4$ each represent a hydrogen atom and $R^3$ represents a carboxymethyl group.

9. A compound as claimed in claim 3 wherein $R^2$ and $R^4$ each represent a hydrogen atom and $R^3$ represents a carboxyl group.

10. A compound as claimed in claim 3 wherein $R^2$ and $R^4$ each represent a carboxyl group and $R^3$ represents a hydrogen atom.

11. A compound as claimed in claim 3 wherein $R^2$ represents a carboxyl group, $R^3$ represents an isopropyl group and $R^4$ represents a hydrogen atom.

12. A compound as claimed in claim 3 wherein $R^2$ represents a carboxyl group, and $R^3$ and $R^4$ each represent a hydrogen atom.

13. A compound as claimed in claim 3 wherein $R^2$ represents a carboxyl group, and $R^3$ and $R^4$ each represent a methyl group.

14. A compound as claimed in claim 3 wherein $R^2$ represents a methyl group, $R^3$ represents a carboxyl group and $R^4$ represents a hydrogen atom.

15. A compound as claimed in claim 3 wherein $R^2$ represents a methoxycarbonyl group, $R^3$ represents a methyl group and $R^4$ represents a hydrogen atom.

16. A compound as claimed in claim 3 wherein $R^2$ represents a hydrazino carbonyl group, $R^3$ represents a methyl group and $R^4$ represents a hydrogen atom.

17. A compound as claimed in claim 3 wherein $R^2$ represents a carboxyl group, $R^3$ represents a hydroxy group and $R^4$ represents a hydrogen atom.

18. A compound as claimed in claim 3 wherein $R^2$ and $R^4$ each represent a hydrogen atom and $R^3$ represents a methoxy group.

19. A compound as claimed in claim 3 wherein $R^2$ represents an amino group, $R^3$ represents a methyl group and $R^4$ represents a hydrogen atom.

20. A compound as claimed in claim 3 wherein $R^2$ represents a hydroxysulfonyl group, $R^3$ represents a methyl group and $R^4$ represents a hydrogen atom.

21. A compound as claimed in claim 3 wherein $R^2$ and $R^4$ each represent a hydrogen atom and $R^3$ represents a chlorine atom.

22. A compound as claimed in claim 1 which is represented by the formula (Ib):

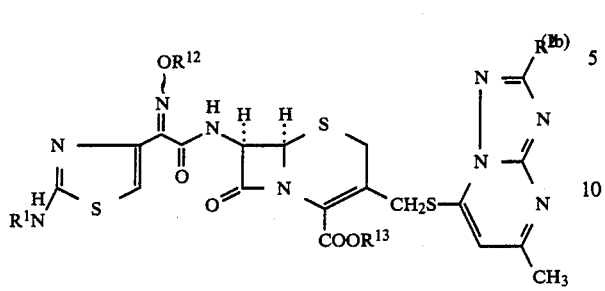

23. A compound as claimed in claim 22 wherein $R^{12}$ represents a hydrogen atom.
24. A compound as claimed in claim 22 wherein $R^{12}$ represents a benzoyl group.
25. A compound as claimed in claim 22 wherein $R^{12}$ represents a 2-furancarbonyl group.
26. A compound as claimed in claim 22 wherein $R^{12}$ represents a 2-thiophenecarbonyl group.
27. A compound as claimed in claim 22 wherein $R^{12}$ represents a 3-pyridinecarbonyl group.
28. A compound as claimed in claim 22 wherein $R^{12}$ represents a 2-pyrrolecarbonyl group.
29. A compound as claimed in claim 22 wherein $R^{12}$ represents a 3,4-methylenedioxybenzoyl group.
30. A compound as claimed in claim 22 wherein $R^{12}$ represents a cyanomethylthioacetyl group.
31. A compound as claimed in claim 22 wherein $R^{12}$ represents a 3,4-diacetoxybenzoyl group.
32. A compound as claimed in claim 22 wherein $R^{12}$ represents a 3,4,5-triacetoxybenzoyl group.
33. A compound as claimed in claim 1 which is represented by the formula (Ic):

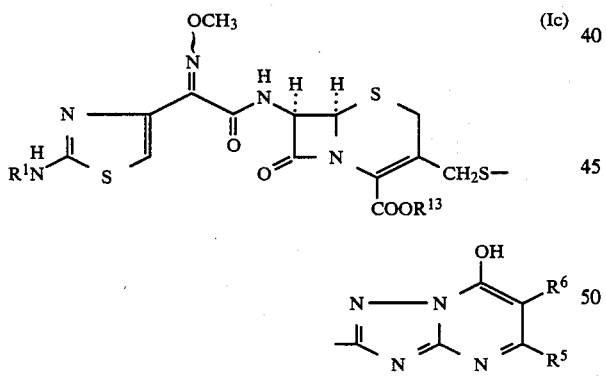

34. A compound as claimed in claim 33 wherein $R^5$ represents a methyl group and $R^6$ represents a hydrogen atom.
35. A compound as claimed in claim 33 wherein $R^5$ represents a hydrogen atom and $R^6$ represents a carboxyl group.
36. A compound as claimed in claim 33 wherein $R^5$ represents a hydrogen atom and $R^6$ represents an ethoxycarbonyl group.
37. A compound as claimed in claim 33 wherein $R^5$ represents a hydrogen atom and $R^6$ represents a piperidinocarbonyl group.
38. A compound as claimed in claim 1 which is represented by the formula (Id):

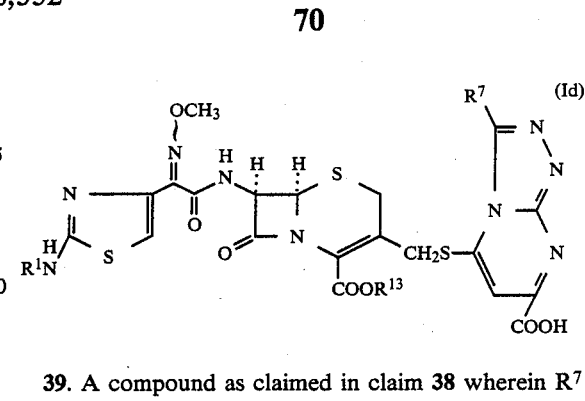

39. A compound as claimed in claim 38 wherein $R^7$ represents a hydrogen atom.
40. A compound as claimed in claim 38 wherein $R^7$ represents a methyl group.
41. A compound as claimed in claim 1 which is represented by the formula (Ie):

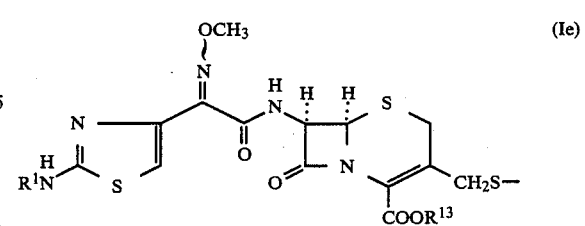

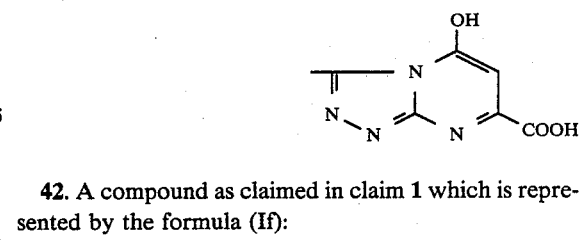

42. A compound as claimed in claim 1 which is represented by the formula (If):

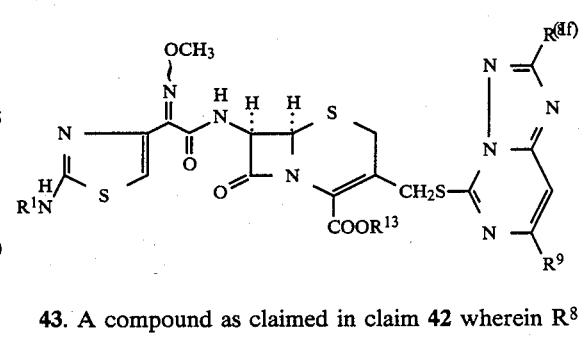

43. A compound as claimed in claim 42 wherein $R^8$ represents a hydrogen atom and $R^9$ represents a carboxyl group.
44. A compound as claimed in claim 42 wherein $R^8$ represents a hydrogen atom and $R^9$ represents an amino group.
45. A compound as claimed in claim 42 wherein $R^8$ represents a hydrogen atom and $R^9$ represents a methyl group.
46. A compound as claimed in claim 42 wherein $R^8$ represents a carboxyl group and $R^9$ represents a methyl group.
47. A compound as claimed in claim 1 which is represented by the formula (Ih):

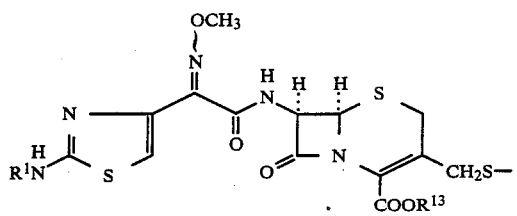

(Ih)

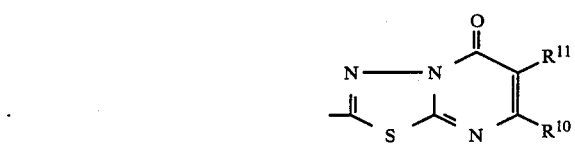

48. A compound as claimed in claim 47 wherein $R^{10}$ represents a methyl group and $R^{11}$ represents a hydrogen atom.

49. A compound as claimed in claim 47 wherein $R^{10}$ represents a hydrogen atom and $R^{11}$ represents a carboxyl group.

50. A compound as claimed in claim 1 which is at least one of (6R,7R)-7-[2-(2-amino-4-thiazolyl)-2-(Z-methoxyimino)acetamido]-3-[(5-methyl-s-triazolo[1,5-a]pyrimidin-7-yl)-thiomethyl]8-oxo-5-thia-1-aza-bicyclo [4.2.0]oct-2-ene-2-carboxylic acid and salts, hydrates and hydrates of salts of said cephalosporin compound.

51. A compound as claimed in claim 1 which is at least one of (6R,7R) -7-[2-(2-amino-4-thiazolyl)-2-(Z--methoxyimino)acetamido]3-[(2-carboxy-5-methyl-s-triazolo[1,5-a]pyrimidin-7-yl)thiomethyl]8-oxo-5-thia-1-aza-bicyclo-[4.2.0]oct-2-ene-2-carboxylic acid and salts, hydrates and hydrates of salts of said cephalosporin compound.

52. A compound as claimed in claim 1 which is at least one of (6R,7R)-7-[2-(2-amino-4-thiazolyl)-2-(Z-methoxyimino)acetamido]-3-[(6-carboxy-s-triazolo[1,5-a]pyrimidin-7-yl)thiomethyl]8-oxo-5-thia-1-azabicyclo [4.2.0]oct-2-ene-2-carboxylic acid and salts, hydrates and hydrates of salts of said cephalosporin compound.

53. A compound as claimed in claim 1 which is at least one of (6R,7R) -7-[2-(2-amino-4-thiazolyl)-2-(Z-methoxyimino)acetamido]3-[(2-carboxymethyl-5-methyl-s-triazolo-[1,5-a]pyrimidin-7-yl)thiomethyl]8-oxo-5-thia-1-azabicyclo [4.2.0]oct-2-ene-2-carboxylic acid and salts, hydrates and hydrates of salts of said cephalosporin compound.

54. A compound as claimed in claim 1 which is at least one of (6R,7R)-7-[2-(2-amino-4-thiazolyl)-2-(Z-methoxyimino)acetamido]-3-[(5-carboxymethyl-s-triazolo[1,5-a]pyrimidin-7-yl)thiomethyl]-8-oxo-5-thia-1-azabicyclo [4.2.0]oct-2-ene-2-carboxylic acid and salts, hydrates and hydrates of salts of said cephalosporin compound.

55. A compound as claimed in claim 1 which is at least one of (6R,7R) -7-[2-(2-amino-4-thiazolyl)-2-(Z-methoxyimino)acetamido]3-[(5-carboxy-s-triazolo[1,5-a]pyrimidin-7-yl)thiomethyl]8-oxo-5-thia-1-azabicyclo [4.2.0]oct-2-ene-2-carboxylic acid and salts, hydrates and hydrates of salts of said cephalosporin compound.

56. A compound as claimed in claim 1 which is at least one of (6R,7R) -7-[2-(2-amino-4-thiazolyl)-2-(Z-methoxyimino)acetamido]3-[(2,6-dicarboxy-s-triazolo[1,5-a]pyrimidin-7-yl)thiomethyl]8-oxo-5-thia-1-azabicyclo[4.2.0]oct-2-ene-2-carboxylic acid and salts, hydrates and hydrates of salts of said cephalosporin compound.

57. A compound as claimed in claim 1 which is at least one of (6R,7R) -7-[2-(2-amino-4-thiazolyl)-2-(Z-hydroxyimino)acetamido]3-[(2-carboxy-5-methyl-s-triazolo[1,5-a]pyrimidin-7-yl)thiomethyl]8-oxo-5-thia-1-azabicyclo-[4.2.0]oct-2-ene-2-carboxylic acid and salts, hydrates and hydrates of salts of said cephalosporin compound.

58. A compound as claimed in claim 1 which is at least one of (6R,7R) -7-[2-(2-amino-4-thiazolyl)-2-(Z-b-enzoyloxyimino)acetamido]3-[(2-carboxy-5-methyl-s-triazolo[1,5-a]pyrimidin-7-yl)thiomethyl]-8-oxo-5-thia1-azabicyclo-[4.2.0]oct-2-ene-2-carboxylic acid and salts, hydrates and hydrates of salts of said cephalosporin compound.

59. A compound as claimed in claim 1 which is at least one of (6R,7R) -7-[2-(2-amino-4-thiazolyl)-2-[Z-(2-furancarbonyl)oxyimino]acetamido]-3 -[(2-carboxy-5-methyl-s-triazolo- [1,5-a]pyrimidin-7-yl)thiomethyl]-8 -oxo-5-thia-1-azabicyclo [4.2.0]oct-2-ene-2-carboxylic acid and salts, hydrates and hydrates of salts of said cephalosporin compound.

60. A compound as claimed in claim 1 which is at least one of (6R,7R) -7-[2-(2-amino-4-thiazolyl)-2-[Z-(2-thiophenecarbonyl)-oxyimino]acetamido]-3-[(2-carboxy-5-methyl-s-triazolo[1,5-a]pyrimidin-7-yl)thiomethyl]-8 -oxo-5-thia-1-azabicyclo[4.2.0]oct-2-ene-2-carboxylic acid and salts, hydrates and hydrates of salts of said cephalosporin compound.

61. A compound as claimed in claim 1 which is at least one of (6R,7R) -7-[2-(2-amino-4-thiazolyl)-2-[Z-(3-pyridinecarbonyl)-oxyimino]acetamido]-3-[(2-carboxy-5-methyl-s-triazolo[1,5-a]pyrimidon-7-yl)thiomethyl]-8 -oxo-5-thia-1-azabicyclo[4.2.0]oct-2-ene-2-carboxylic acid and salts, hydrates and hydrates of salts of said cephalosporin compound.

62. A compound as claimed in claim 1 which is at least one of (6R,7R) -7-[2-(2-amino-4-thiazolyl)-2-[Z-(2-pyrrolecarbonyl)oxyimino]acetamido]-3-[(2-carboxy-5-methyl-s-triazolo-[1,5-a]pyrimidin-7-yl)thiomethyl]-8 -oxo-5-thia-1-azabicyclo oct-2-ene-2-carboxylic acid and salts, hydrates and hydrates of salts of said cephalosporin compound.

63. A compound as claimed in claim 1 which is at least one of (6R,7R) -7-[2-(2amino-4-thiazolyl)-2-[Z-(3,-4-methylenedioxy-benzoly)oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid and salts, hydrates and hydrates of salts of said cephalosporin compound.

64. A compound as claimed in claim 1 which is at least one of (6R,7R) -7-[2-(2-amino-4-thiazolyl)-2-(Z-cyanomethylthioacetyl-oxyimino)acetamido]-3-[(2-carboxy-5-methyl-s-triazolo[1,5-a]pyrimidin-7-yl)thiomethyl]-8 -oxo-5-thia-1-azabicyclo[4.2.0]oct-2-ene-2-carboxylic acid and salts, hydrates and hydrates of salts of said cephalosporin compound.

65. A compound as claimed in claim 1 which is at least one of (6R,7R) -7-[2-(2-amino-4-thiazolyl)-2-[Z-(3,4-diacetoxybenzoyl-oxyimino]acetamido]-3-[(2-carboxy-5-methyl-s-triazolo[1,5a]pyrimidin-7-yl)thiomethyl]-8 -oxo-5-thia-1-azabicyclo[4.2.0]oct-2-ene-2-carboxylic acid and salts, hydrates and hydrates of salts of said cephalosporin compound.

66. A compound as claimed in claim 1 which is at least one of (6R,7R) -7-[2-(2-amino-4-thiazolyl)-2-[Z-(3,4,5-triacetoxybenzoyl)oxyimino]acetamido]-3 -[(2- carboxy-5-methyl-s-triazolo[1,5-a]pyrimidin-7-yl)thiomethyl]-8-oxo-5-thia-1-azabicyclo[4.2.0]oct-2-ene-2-carboxylic acid and salts, hydrates and hydrates of salts of said cephalosporin compound.

67. A compound as claimed in claim 1 which is at least one of (6R,7R) -7-[2-(2-amino-4-thiazolyl)-2-(Z-methoxyimino)acetamido]-3-[(2-carboxy-5-isopropyl-s-triazolo[1,5-a]-pyrimidin-7-yl)thiomethyl]-8-oxo-5-thia-1-azabicyclo-[4.2.0]oct-2-ene-2-carboxylic acid and salts, hydrates and hydrates of salts of said cephalosporin compound.

68. A compound as claimed in claim 1 which is at least one of (6R,7R) -7-[2-(2-amino-4-thiazolyl)-2-(Z-methoxyimino)acetamido]-3-[(2-carboxy-s-triazolo[1,5-a]pyrimidin-7-yl)thiomethyl]-8-oxo-5-thia-1-azabicyclo[4.2.0]oct-2-ene-2-carboxylic acid and salts, hydrates and hydrates of salts of said cephalosporin compound.

69. A compound as claimed in claim 1 which is at least one of (6R,7R) -7-[2-(2-amino-4-thiazolyl)-2-(Z-methoxyimino)acetamido]-3-[(2-carboxy-5,6-dimethyl-s-triazolo[1,5-a]-pyrimidin-7-yl)thiomethyl]-8-oxo-5-thia-1-azabicyclo-[4.2.0]oct-2-ene-2-carboxylic acid and salts, hydrates and hydrates of salts of said cephalosporin compound.

70. A compound as claimed in claim 1 which is at least one of (6R,7R) -7-[2-(2-amino-4-thiazolyl)-2-(Z--methoxyimino)acetamido]-3-[(5-carboxy-2-methyl-s-triazolo[1,5-a]-pyrimidin-7-yl)thiomethyl]-8-oxo-5-thia-1-azabicyclo[4.2.0]oct-2-ene-2-carboxylic acid and salts, hydrates and hydrates of salts of said cephalosporin compound.

71. A compound as claimed in claim 1 which is at least one of (6R,7R) -7-[2-(2-amino-4-thiazolyl)-2-(Z-methoxyimino)acetamido]-3 -[2-methoxycarbonyl-5-methyl-s-triazolo-[1,5-a]pyrimidin-7-yl)thiomethyl] -8-oxo-5-thia-1-azabicyclo[4.2.0]oct-2-ene-2-carboxylic acid and salts, hydrates and hydrates of salts of said cephalosporin compound.

72. A compound as claimed in claim 1 which is at least one of (6R,7R) -7-[2-(2-amino-4-thiazolyl)-2-(Z-methoxyimino)acetamido]-3-[(2hydrazinocarbonyl-5-methyl-s-triazolo-[1,5-a]pyrimidin-7-yl)thiomethyl]-8-oxo-5 -thia-1-azabicyclo[4.2.0]oct-2-ene-carboxylic acid and salts, hydrates and hydrates of salts of said cephalosporin compound.

73. A compound as claimed in claim 1 which is at least one of (6R,7R) -7-[2-(2-amino-4-thiazolyl)-2-(Z-methoxyimino)actamido]-3-[(2-carboxy-5-hydroxy-s-triazolo[1,5-a]pyrimidin-7-yl)thiomethyl]-8-oxo-5-thia-1azabicyclo-[4.2.0 oct-2-ene-2-carboxylic acid and salts, hydrates and hydrates of salts of said cephalosporin compound.

74. A compound as claimed in claim 1 which is at least one of (6R,7R) -7-[2-(2-amino-4-thiazolyl)-2-(Z-methoxyimino)acetamido]-3-[(5-methoxy-s-triazolo[1,5-a]pyrimidin-7yl)thiomethyl]-8-oxo-5-thia-1-azabicyclo[4.2.0]oct-2-ene-2-carboxylic acid and salts, hydrates and hydrates of salts of said cephalosporin compound.

75. A compound as claimed in claim 1 which is at least one of (6R,7R) -7-[2-(2-amino-4-thiazolyl)-2-(Z--methoxyimino)acetamido]-3-[(2-amino-5-methyl-s-triazolo[1,5-a]pyrimidin-7-yl)thiomethyl]-8-oxo-5-thia-1-azabicyclo-[4.2.0]oct-2-ene-2-carboxylic acid and salts, hydrates and hydrates of salts of said cephalosporin compound.

76. A compound as claimed in claim 1 which is at least one of (6R,7R) -7-[2-(2-amino-4-thiazolyl)-2-(-Z-methoxyimino)acetamido]-3-[(2-cyano-5-methyl-s-triazolo[1,5-a]pyrimidin-7-yl)thiomethyl]-8-oxo-5-thia-1-azabicyclo-[4.2.0]oct-2-ene-2-carboxylic acid and salts, hydrates and hydrates of salts of said cephalosporin compound.

77. A pharmaceutical composition as claimed in claim 1 which is at least one of (6R,7R) -7-[2-(2amino-4-thiazolyl)-2-(Z-methoxyimino)acetamido]-3-[(2-hydroxysulfonyl-5-methyl-s-triazolo-[1,5-pyrimidin-7-yl)thiomethyl]-8-oxo-5-thia-1-azabicyclo[4.2.0]oct-2-ene-2-carboxylic acid and salts, hydrates and hydrates of salts of said cephalosporin compound.

78. A compound as claimed in claim 1 which is at least one of (6R,7R) -7-[2-(2-amino-4-thiazolyl)-2-(Z-methoxyimino)acetamido]-3-[(5-chloro-s-triazolo[1,5-a]pyrimidin-7-yl)-thiomethyl]-8-oxo-5-thia-1-azabicyclo[4.2.0]oct-2-ene-2-carboxylic acid and salts, hydrates and hydrates of salts of said cephalosporin compound.

79. A compound as claimed in claimed in claim 1 which is at least one of (6R,7R) -7-[2-(2-amino-4-thiazolyl)-2-(Z-methoxyimino)acetamido]-3-[(7-hydroxy-5-methyl-s-triazolo[1,5-a]pyrimidin-2-yl)thiomethyl]-8-oxo-5-thia-1-azabicyclo-[4.2.0]oct-2-ene-2-carboxylic acid and salts, hydrates and hydrates of salts of said cephalosporin compound.

80. A compound as claimed in claim 1 which is at least one of (6R,7R) -7-[2-(2-amino-4-thiazolyl)-2-(Z-methoxyimino)acetamido]-3 -[(6-carboxy-7-hydroxy-s-triazolo[1,5,-a]pyrimidin-2-yl)thiomethyl] -8-oxo-5-thia-1-azabicyclo-[4.2.0]oct-2-ene-2-carboxylic acid and salts, hydrates and hydrates of salts of said cephalosporin compound.

81. A compound as claimed in claim 1 which is at least one of (6R,7R) -7-[2-(2-amino-4-thiazolyl)-2-(Z-methoxyimino)acetamido]-3-[(6-ethoxycarbonyl-7-hydroxy-s-triazolo-[1,5-a]pyrimidin-2-yl]-8-oxo-5 -thia-1-azabicyclo[4.2.0]oct-2-ene-2-carboxylic acid and salts, hydrates and hydrates of salts of said cephalosporin compound.

82. A compound as claimed in claim 1 which is at least one of (6R,7R) -7-[2-(2-amino-4-thiazolyl)-2-(Z-methoxyimino)acetamido]-3 -[7-hydroxy-6-piperidinocarbonyl-s-triazolo [1,5,-a]pyrimidin-2-yl)thiomethyl]-8-oxo-5-thia-1-azabicyclo[4.2.0]oct-2-ene-2-carboxylic acid and salts, hydrates and hydrates of salts of said cephalosporin compound.

83. A compound as claimed in claim 1 which is at least one of (6R,7R) -7-[2-(2-amino-4-thiazolyl)-2-(Z-methoxyimino)acetamido]-3-[(7-carboxy-s-triazolo[4,3-a]pyrimidin-5-thiomethyl]-8-oxo-5-thia-1azabicyclo[4.2.0]oct-2-ene-2-carboxylic acid and salts, hydrates and hydrates of salts of said cephalosporin compound.

84. A compound as claimed in claim 1 which is at least one of (6R,7R) -7-[2-(2-amino-4-thiazolyl)-2-(Z-methoxyimino)acetamido]-3-[(7-carboxy-3-methyl-s-traizolo[4,3,-a]pyrimidin-5-yl)thiomethyl]-8-oxo-5-thia-1-azabicyclo-[4.2.0]oct-2-ene-2-carboxylic acid and salts, hydrates and hydrates of salts of said cephalosporin compound.

85. A compound as claimed in claim 1 which is at least one of (6R,7R) -7-[2-(2-amino-4-thiazolyl)-2-(Z--methoxyimino)acetamido]-3-[(7-carboxy-5-hydroxy-s-triazolo[4.2.0]-pyrimidin-3-yl)thiomethyl]-8-oxo-5-thia-1-azabicyclo-[4.2.0]oct-2-ene-2-carboxylic acid and salts, hydrates and hydrates of salts of said cephalosporin compound.

86. A compound as claimed in claim 1 which is at least one of (6R,7R) -7-[2-(2-amino-4-thiazolyl)-2-(Z-methoxyimino)acetamido]-3-[(7-carboxy-s-triazolo[1,5- c]pyrimidin-5-yl)thiomethyl]-8-oxo-5-thia-1-azabicyclo[4.2.0]oct-2-ene-2-carboxylic acid and salts, hydrates and hydrates of salts of said cephalosporin compound.

87. A compound as claimed in claim 1 which is at least one of (6R,7R) -7-[2-(2-amino-4-thiazolyl)-2-(Z-methoxyimino)acetamido]-3-[(7-amino-s-triazolo [1,5-c]pyrimidin-5yl)-thiomethyl]-8-oxo-5-thia-1-azabicyclo[4.2.0]oct-2-ene-2-carboxylic acid and salts, hydrates and hydrates of salts of said cephalosporin compound.

88. A compound as claimed in claim 1 which is at least one of (6R,7R) -7-[2-(2-amino-4-thiazolyl)-2-(Z-methoxyimino)acetamido]-3-[(7-methyl-s-triazolo[1,5-c]pyrimidin-5-yl)-thiomethyl]-8-oxo-5-thia-1-azabicyclo[4.2.0]oct-2-ene-2-carboxylic acid and salts, hydrates and hydrates of salts of said cephalosporin compound.

89. A compound as claimed in claim 1 which is at least one of (6R,7R) -7-[2-(2-amino-4-thiazolyl)-2-(Z-methoxyimino)acetamido]-3-[(2-carboxy-7-methyl-s-triazolo[1,5,-c] pyrimidin-5-yl)thiomethyl]-8-oxo-5-thia-1-azabicyclo-[4.2.0]oct-2-ene-2-carboxylic acid and salts, hydrates and hydrates of salts of said cephalosporin compound.

90. A compound as claimed in claim 1 which at least one of (6R,7R) -7-[2-(2-amino-4-thiazolyl)-2-(Z-methoxyimino)acetamido]-3-[(7-methyl-5-oxo-5H-1,3,4-thiadiazolo-[3,2-a]pyrimidin-2-yl)thiomethyl]-8-oxo-5-thia-1-azabicyclo[4.2.0]oct -2-ene-2-carbosylic acid and salts, hydrates and hydrates of salts of said cephalosporin compound.

91. A compound as claimed in claim 1 which is at least one of (6R,7R) -7-[2-(2-amino-4-thiazolyl) -2-(Z-methoxyimino)acetamido]-3-[(6-carboxy-5-oxo-5H-1,3,4-thiadiazolo-[3,2,-a]pyrimidin-2-yl)thiomethyl]-8-oxo-5-thia-1-azabicyclo[4.2.0]oct-2-ene-2-carboxylic acid and salts, hydrates and hydrates of salts of said cephalosporin compound.

92. An antibiotic composition comprising a mixture of two or more compounds of claim 1 and salts, hydrates and hydrates of salts of said cephalosporin compound and a pharmaceutically acceptable carrier.

93. An antibiotic composition comprising a pharmaceutically effective amount of a compound of claim 1 or salts, hydrates and hydrates of salts of said cephalosporin compound and a pharmaceutically acceptable carrier.

94. A method of treating infectious diseases comprising administering an infectious disease treating effective amount of the antibiotic composition of claim 93 to a patient infected by an infectious disease.

* * * * *